United States Patent
Halfbrodt et al.

(10) Patent No.: US 7,329,679 B2
(45) Date of Patent: Feb. 12, 2008

(54) 1,2 DIARYLBENZIMIDAZOLES AND THEIR PHARMACEUTICAL USE

(75) Inventors: Wolfgang Halfbrodt, Berlin (DE); Joachim Kuhnke, Postdam (DE); Ursula Moenning, Woltersdorf (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 11/299,135

(22) Filed: Dec. 8, 2005

(65) Prior Publication Data

US 2006/0094770 A1    May 4, 2006

Related U.S. Application Data

(62) Division of application No. 09/759,360, filed on Jan. 16, 2001.

(60) Provisional application No. 60/178,324, filed on Jan. 27, 2000.

(51) Int. Cl.
*A61K 31/44* (2006.01)
*A61K 31/415* (2006.01)

(52) U.S. Cl. ...................... 514/357; 514/397

(58) Field of Classification Search ............... 514/357, 514/397
See application file for complete search history.

(56) References Cited

FOREIGN PATENT DOCUMENTS

| | | |
|---|---|---|
| EP | 0 104 727 A1 | 4/1984 |
| EP | 0 528 164 A2 | 2/1993 |
| EP | 0 531 883 A1 | 3/1993 |
| EP | 0 520 200 A2 | 12/1993 |
| EP | 0 694 535 | 1/1996 |
| GB | 1174493 | 12/1969 |
| WO | WO95/07263 | 3/1995 |
| WO | WO97/12613 | 4/1997 |
| WO | WO97/33873 | 9/1997 |

OTHER PUBLICATIONS

McGeer et. al., "The Possible role of complement activation in Alzheimer disease", Trends in Molecular Medicine, vol. 8, No. 11, Nov. 2002.*
Nakamura, "Regulating Factors for Microglial Activation", Biol. Pharm. Bull. 25(8)945-953 (2002).*
Hcaplus 127:5020.*
Thomas et al., "Minocycline: Neuroprotective Mechanisms in Parkinson's Disease", Current Pharmaceutical Design, 2004, 679-686.
Hcaplus 2005:20310 Lott et al.
Hcplus 125:300996.
Hcplus 124:289536, Burns et al.
Hcplus 122:236400.
Hcplus 132:206042.

* cited by examiner

*Primary Examiner*—Janet L. Andres
*Assistant Examiner*—Binta Robinson
(74) *Attorney, Agent, or Firm*—Millen, White, Zelano & Branigan, P.C.

(57) ABSTRACT

Benzimidazoles of general formula I

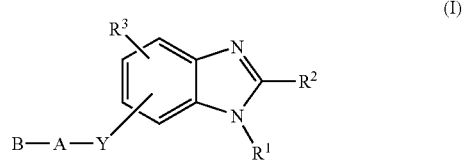

and the use of benzimidazole derivatives for the production of pharmaceutical agents for treatment and prophylaxis of diseases that are associated with a microglia activation are described.

32 Claims, No Drawings

1,2 DIARYLBENZIMIDAZOLES AND THEIR PHARMACEUTICAL USE

This application is a division of copending application U.S. Ser. No. 09/759,360, filed Jan. 16, 2001, which claims priority to U.S. Provisional application Ser. 60/178,324, filed Jan. 27, 2000, the entire disclosures of which are incorporated herein by reference.

Benefit is claimed of the filing date of Jan. 27, 2000 of Provisional application 60/178,324, whose entire disclosure is incorporated by reference herein.

The invention relates to new benzimidazole derivatives and the use of benzimidazole derivatives for the production of pharmaceutical agents for treatment and prophylaxis of diseases that are associated with a microglia activation.

Almost all degenerative diseases of the central nervous system are connected to chronic inflammation. A central step of the inflammation process is the activation of mononuclear phagocyte cells, the microglia. This is carried out in, e.g., Alzheimer's disease by senile plaques, in Creutzfeldt-Jacob disease by a prion protein and in ischemic stroke by dead cells. The microglia can remain for a prolonged period in the activated state, in which they produce and secrete various inflammation factors, e.g., reactive oxygen/nitrogen intermediate products, proteases, cytokines, complement factors and neurotoxins. The latter in turn produce neuronal dysfunction and degeneration.

For a possible treatment of neuroinflammation, to date non-steroidal antiinflammatory agents (COX II inhibitors) (McGeer, P. L.; Roger, Neurology 42, 447-449 (1992), Rogers, J.; Kirby, L. C.; Hempleman, S. R.; Berry, D. L.; McGeer, P. L.; Kaszniak, A. W.; Zalinski, J.; Cofield, M.; Mansukhani, L.; Wilson, P.; Kogan, F. Neurology 43, 1609-1611 (1993), Andersen, K.; Launer, L. J.; Ott, A.; Hoes, A. W.; Breteler, M. M. B.; Hofman, A. Neurology 45, 1441-1445 (1995), Breitner, J. C. S.; Gau, B. A.; Welsh, K. A.; Plassman, B. L.; McDonald, W. M.; Helms, M. J.; Anthony, J. C. Neurology 44, 227-232 (1994), The Canadian Study of Health and Aging, Neurology 44, 2073-2079 (1994)), cytokine modulators (McGeer, P. L.; McGeer, E. G. Brain Res. Rev 21:195-218 (1995), McGeer, E. G.; McGeer, P. L., CNS Drugs 7, 214-228 (1997), Barone, F. C. and Feuerstein, G. Z., J. Cerebral Blood Flow and Metabolism 19, 819-834 (1999) and complement-cascade-inhibitors (Chen., S.; Frederickson, R. C. A., and Brunden, K. R., Neurobiol. Aging (1996), McGeer, E. G.; McGeer, P. L., Drugs 55: 739-746 (1998)) have been described. These substances inhibit the synthesis or the action of individual inflammation factors. It would be desirable, however, to have substances that inhibit an earlier step in the inflammation process and thus prevent the development or action of many inflammation factors.

The problem was solved by preparation of benzimidazole derivatives of general formula I, their tautomeric or isomeric forms or salts

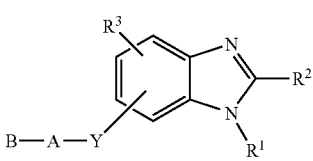

(I)

in which $R^1$ means a monocyclic or bicyclic $C_{6-12}$ aryl group or a monocyclic or bicyclic 5- to 10-membered heteroaryl group with 1-4 heteroatoms selected from the group that consists of N, S or O, whereby the mentioned aryl or heteroaryl group can be substituted with up to three of the following substituents, independently of one another:

F, Cl, Br, I, $C(NH)NH_2$, $C(NH)NHR^4$, $C(NH)NR^4R^{4'}$, $C(NR^4)NH_2$, $C(NR^4)NHR^{4'}$, $C(NR^4)NR^4R^{4'}$, XOH, $XOR^4$, $XOCOR^4$, $XOCONHR^4$, $XOCOOR^4$, $XCOR^4$, $XC(NOH)R^4$, $XC(NOR^4)R^{4'}$, $XC(NO(COR^4))R^{4'}$ XCN, XCOOH, $XCOOR^4$, $XCONH_2$, $XCONR^4R^{4'}$, $XCONHR^4$, XCONHOH, XCONHOR$^4$, $XCOSR^4$ $XSR^4$, $XSOR^4$, $XSO_2R^4$, $SO_2NH_2$, $SO_2NHR^4$, $SO_2NR^4R^{4'}$, $NO_2$, $XNH_2$, $XNHR^4$, $XNR^4R^{4'}$, $XNHSO_2R^4$, $XN(SO_2R^4)SO_2R^{4'}$, $XNR^4SO_2R^{4'}$, $XNHCOR^4$, $XNHCOOR^4$, XNHCONHR$^4$, tetrahydro-2,5-dioxopyrrol-1-yl, 2,5-dihydro-2,5-dioxopyrrol-1-yl, 2,7-dihydro-2,7-dioxoisoindol-1-yl, $R^4$, whereby two substituents at $R^1$, if they are in ortho-position to one another, can be linked to one another in such a way that they jointly form methanediylbisoxy, ethane-1,2-diylbisoxy, propane-1,3-diyl, butane-1,4-diyl, $R^2$ means a monocyclic or bicyclic $C_{6-10}$ aryl group or a monocyclic or bicyclic 5- to 10-membered heteroaryl group with 1-4 heteroatoms selected from the group that consists of N, S or O, whereby the mentioned aryl or heteroaryl group can be substituted with up to three of the following substituents, independently of one another:

F, Cl, Br, I, XOH, $XOR^4$, $XOCOR^4$, $XOCONHR^4$, $XOCOOR^4$, $XCOR^4$, $XC(NOH)R^4$, $XC(NOR^4)R^{4'}$, $XC(NO(COR^4))R^{4'}$, XCOOH, $XCOOR^4$, $XCONH_2$, $XCONHR^4$, $XCONR^4R^{4'}$, XCONHOH, XCONHOR$^4$, $XCOSR^4$, $XSR^4$, $XSOR^4$, $XSO_2R^4$, $SO_2NH_2$, $SO_2NHR^4$, $SO_2NR^4R^{4'}$, $NO_2$, $XNHR^4$, $XNR^4R^{4'}$, $XNHSO_2R^4$, $XN(SO_2R^4)SO_2R^{4'}$, $XNR^4SO_2R^{4'}$, tetrahydro-2,5-dioxopyrrol-1-yl, 2,5-dihydro-2,5-dioxopyrrol-1-yl, 2,7-dihydro-2,7-dioxoisoindol-1-yl, $R^4$, whereby two substituents at $R^2$, if they are in ortho-position to one another, can be linked to one another in such a way that they jointly form methanediylbisoxy, ethane-1,2-diylbisoxy, propane-1,3-diyl, butane-1,4-diyl, $R^3$ means one or two substituents, which form, independently of one another:

hydrogen, F, Cl, Br, I, XOH, $XOR^4$, $XOCOR^4$, $XOCONHR^4$, $XOCOOR^4$, $XCOR^4$, $XC(NOH)R^4$, $XC(NOR^4)R^{4'}$, $XC(NO(COR^4))R^{4'}$, XCN, XCOOH, $XCOOR^4$, $XCONH_2$, $XCONHR^4$, $XCONR^4R^{4'}$, XCONHOH, XCONHOR$^4$, $XCOSR^4$, $XSR^4$, $XSOR^4$, $XSO_2R^4$, $SO_2NH_2$, $SO_2NHR^4$, $SO_2NR^4R^{4'}$, $NO_2$, $XNH_2$, $XNHR^4$, $XNR^4R^{4'}$, $XNHSO_2R^4$, $XNR^4SO_2R^{4'}$, $XN(SO_2R^4)(SO_2R^4)$, $XNHCOR^4$, $XNHCOOR^4$, XNHCONHR$^4$, tetrahydro-2,5-dioxopyrrol-1-yl, 2,5-dihydro-2,5-dioxopyrrol-1-yl, 2,7-dihydro-2,7-dioxoisoindol-1-yl, or $R^3$ can be $R^4$, whereby two substituents at $R^3$, if they are in ortho-position to one another, can be linked to one another in such a way that they jointly form methanediylbisoxy, ethane-1,2-diylbisoxy, propane-1,3-diyl, butane-1,4-diyl, $R^4$ and $R^{4'}$, independently of one another, mean $C_{1-4}$ perfluoroalkyl, $C_{1-6}$ alkyl, $C_{2-6}$ alkenyl, $C_{2-6}$ alkinyl, $C_{3-7}$ cycloalkyl, ($C_{1-3}$ alkyl-$C_{3-7}$ cycloalkyl), $C_{1-3}$ alkyl-$C_{6-10}$ aryl, $C_{1-3}$ alkyl-5 to 10-membered heteroaryl; with 1-4 N, S or O atoms, $C_{6-10}$ aryl or 5- to 10-membered heteroaryl with 1-4 N, S or O atoms, whereby the aryl and heteroaryl groups can be substituted with one or two substituents from the group that consists of F, Cl, Br, $CH_3$, $C_2H_5$, $NO_2$, $OCH_3$, $OC_2H_5$, $CF_3$, $C_2F_5$ or else can carry an annelated methanediylbisoxy group or ethane-1,2-diylbisoxy group, and in addition in a 5-membered cycloalkyl ring, a ring member can be an N or an O, and in a 6- or 7-membered cycloalkyl ring, one or two ring members can be N and/or O, whereby ring nitrogens optionally can be substituted with $C_{1-3}$ alkyl or $C_{1-3}$ alkanoyl, $R^5$ and $R^{5'}$, independently of one another, mean $C_{1-6}$ alkyl, $C_{2-6}$ alkenyl, $C_{2-6}$ alkinyl, whereby a carbon atom can be exchanged for O, S, SO, $SO_2$, NH, $NC_{1-3}$ alkyl or $NC_{1-3}$ alkanoyl, $C_{3-7}$ cycloalkyl-$C_{0-3}$ alkyl, whereby in a 5-membered cycloalkyl ring, a ring member can be an N or an O and in a 6- or 7-membered cycloalkyl ring, one or two ring members can be N and/or O, whereby ring nitrogens optionally can be substituted with $C_{1-3}$ alkyl or $C_{1-3}$ alkanoyl, $C_{6-10}$ aryl or 5- to 10-membered heteroaryl with 1-4 heteroatoms from N, S, and O, whereby the mentioned alkyl, alkenyl and alkinyl chains can be substituted with one of the previously mentioned cycloalkyls, aryls or heteroaryls, whereby all previously mentioned alkyl and cycloalkyl radicals with up to two substituents consisting of $CF_3$, $C_2F_5$, OH, $OC_{1-3}$ alkyl, NH2, $NHC_{1-3}$ alkyl, $NHC_{1-3}$ alkanoyl, $N(C_{1-3}$ alkyl$)_2$, $N(C_{1-3}$ alkyl$)$ $(C_{1-3}$ alkanoyl$)$, COOH, $CONH_2$, $COOC_{1-3}$ alkyl and all previously mentioned aryl and heteroaryl groups can be substituted with one or two substituents from the group that consists of F, Cl, Br, $CH_3$, $C_2H_5$, $NO_2$, $OCH_3$, $OC_2H_5$, $CF_3$, $C_2F_5$ or else can carry an annelated methanediylbisoxy, ethane-1,2-diylbisoxy group, or $R^5$ and $R^{5'}$ together with the nitrogen atom form a 5- to 7-membered heterocyclic compound, which can contain another oxygen, nitrogen or sulfur atom and can be substituted with $C_{1-4}$ alkyl, $C_{1-4}$ alkoxy-$C_{0-2}$ alkyl, $C_{1-4}$ alkoxy-carbonyl, aminocarbonyl or phenyl, A means $C_{1-10}$ alkanediyl, $C_{2-10}$ alkenediyl, $C_{2-10}$ alkinediyl, ($C_{0-5}$ alkanediyl-$C_{3-7}$ cycloalkanediyl-$C_{0-5}$ alkanediyl), whereby in a 5-membered cycloalkyl ring, a ring member can be an N or an O, and in a 6- or 7-membered cycloalkyl ring, one or two ring members can be N and/or O, whereby ring nitrogens optionally can be substituted with $C_{1-3}$ alkyl or $C_{1-3}$ alkanoyl, whereby in the above-mentioned aliphatic chains, a carbon atom or two carbon atoms can be exchanged for O, NH, $NC_{1-3}$ alkyl, $NC_{1-3}$ alkanoyl, and whereby alkyl or cycloalkyl groups can be substituted with up to two substituents consisting of =O, OH, $OC_{1-3}$ alkyl, NH2, $NHC_{1-3}$ alkyl, $NHC_{1-3}$ alkanoyl, $N(C_{1-3}$ alkyl$)_2$, $N(C_{1-3}$ alkyl$)(C_{1-3}$ alkanoyl$)$, B means COOH, $COOR^5$, $CONH_2$, $CONHNH_2$, $CONHR^5$, $CONR^5R^{5'}$, CONHOH, $CONHOR^5$, $SO_3H$, $SO_2NH_2$, $SO_2NHR^5$, $SO_2NR^5R^{5'}$, $PO_3H$, PO(OH)(OR$^5$), PO(OR$^5$)(OR$^{5'}$), PO(OH)(NHR$^5$), PO(NHR$^5$)(NHR$^5$), tetrazolyl, in each case bonded to a carbon atom of group A, or the entire group Y-A-B $N(SO_2R^4)$ $(SO_2R^{4'})$ or $NHSO_2R^4$, X means a bond, $CH_2$, $(CH_2)_2$, $CH(CH_3)$, $(CH_2)_3$, $CH(CH_2CH_3)$, $CH(CH_3)CH_2$, $CH_2CH(CH_3)$, Y means O, NH, $NR^4$, $NCOR^4$, $NSO_2R^4$, with the proviso, if Y means NH, $NR^4$, $NCOR^4$ or $NSO_2R^4$, and a) the substituent $R^2$ contains a nitrogen-containing, saturated heterocyclic compound, this heterocyclic compound is not substituted in the imine nitrogen with H, methyl, ethyl, propyl or isopropyl, or b) in optionally present groups $XNHR^4$ or $XNR^4R^{4'}$ of the substituent $R^2$, $R^4$ and/or $R^{4'}$ does not mean $C_{1-4}$ alkyl, then B does not mean COOH, $SO_3H$, $PO_3H_2$ or tetrazolyl at the same time, and $R^1$ and $R^2$, independently of one another, mean $C_{5-6}$ heteroaryl or phenyl, if the latter, independently of one another, are unsubstituted, or are substituted simply with $C_{1-6}$ alkyl, $C_{1-4}$ perfluoroalkyl, $OC_{1-6}$ alkyl, $OC_{1-4}$ perfluoroalkyl, COOH, $COOC_{1-6}$ alkyl, $COC_{1-6}$ alkyl, $CONH_2$, $CONHR^4$, $NO_2$, $NH_2$, $NHCOR^4$, $NHSO_2R^4$, or with 1 or 2 halogen atoms from the group that consists of F, Cl, Br, and I, and whereby the following compounds are excluded:

[(1,2-Diphenyl-1H-benzimidazol-6-yl)oxy]acetic acid methyl ester,

5-[(1,2-diphenyl-1H-benzimidazol-6-yl)oxy]pentanoic acid methyl ester,

4-[(1,2-diphenyl-1H-benzimidazol-6-yl)oxy]butanoic acid ethyl ester,

5-[[1-(4-nitrophenyl)-2-phenyl-1H-benzimidazol-6-yl]oxy]-pentanoic acid methyl ester, 6-[[1-(4-nitrophenyl)-2-phenyl-1H-benzimidazol-6-yl]oxy] hexanoic acid methyl ester, 5-[[1-(4-aminophenyl)-2-phenyl-1H-benzimidazol-6-yl] oxy]pentanoic acid methyl ester, 5-[[1-[4-[[(4-chlorophenyl)sulfonyl]amino]phenyl]-2-phenyl-1H-benzimidazol-6-yl]oxy]pentanoic acid methyl ester, 5-[[1-[4-[(acetyl)amino]phenyl]-2-phenyl-1H-benzimidazol-6-yl]oxy]pentanoic acid methyl ester 5-[[1-(3-nitrophenyl)-2-phenyl-1H-benzimidazol-6-yl]oxy] pentanoic acid methyl ester, 6-[[1-(3-nitrophenyl)-2-phenyl-1H-benzimidazol-6-yl]oxy] hexanoic acid methyl ester, 5-[[1-(3-aminophenyl)-2-phenyl-1H-benzimidazol-6-yl] oxy]pentanoic acid methyl ester, 5-[[1-[3-[[(4-chlorophenyl)sulfonyl]amino]phenyl]-2-phenyl-1H-benzimidazol-6-yl]oxy]pentanoic acid methyl ester, 5-[[1-[3-[(acetyl)amino]phenyl]-2-phenyl-1H-benzimidazol-6-yl]oxy]pentanoic acid methyl ester.

The physiologically compatible salts can be formed with inorganic and organic acids, such as, for example, oxalic acid, lactic acid, citric acid, fumaric acid, acetic acid, maleic acid, tartaric acid, phosphoric acid, HCl, HBr, sulfuric acid, p-toluenesulfonic acid, and methanesulfonic acid.

For salt formation of acid groups, inorganic or organic bases are also suitable that are known for the formation of physiologically compatible salts, such as, for example, alkali hydroxides, sodium and potassium hydroxide, alkaline-earth hydroxides such as calcium hydroxide, ammonia, amines such as ethanolamine, diethanolamine, triethanolamine, N-methylglucamine, tris-(hydroxymethyl)-methylamine.

An "aryl group" is defined in particular as an optionally substituted phenyl group or biphenyl, naphthyl, indane or fluorenyl.

A heteroaryl group is built up of 5-10 skeleton atoms and can contain 1-4 heteroatoms. Heteroatoms are oxygen (O), nitrogen (N) and sulfur (S). Examples of a monocyclic heteroaryl group axe pyrrolyl, thienyl, furanyl, imidazolyl, thiazolyl, isothiazolyl, oxazolyl, isoxazolyl, pyrazolyl, furazanyl, pyridyl, pyrimidinyl, pyrazinyl and pyridazinyl. Examples of a bicyclic heteroaryl group are thienoimidazolyl, indolyl, isoindolyl, benzothiophenyl, benzofuranyl, benzimidazolyl, indazolyl, imidazopyridinyl, purinyl, quinolyl, isoquinolyl, phthalazinyl, quinazolinyl, quinaxolinyl, cinnolinyl, naphthyridinyl and pteridinyl. If the aryl groups or heteroaryl groups are part of $R^1$, the binding to N of the benzimidazole is carried out via a carbon atom.

Alkyl groups can be straight-chain or branched. Examples are methyl, ethyl, propyl, isopropyl, n-butyl, sec-butyl, tert-butyl, n-pentyl, sec-pentyl, tert-pentyl, neopentyl, n-hexyl, sec-hexyl, heptyl, octyl, nonyl, and hexyl.

Perfluorinated alkyls are preferably $CF_3$ and $C_2F_5$.

Alkenyl groups can be straight-chain or branched. For example, the following radicals can be mentioned: vinyl, 2-propenyl, 1-propenyl, 2-butenyl, 1-butenyl, 1-methyl-1-propenyl, 2-methyl-2-propenyl, 3-methyl-2-propenyl.

Alkinyl groups can be straight-chain or branched. Examples of this are: ethinyl, 1-propinyl, 2-propinyl, 1-butinyl, and 2-butinyl.

Cycloalkyl groups are defined respectively as cyclopropyl, cyclobutyl, cyclopentyl, cyclohexyl or cycloheptyl.

As a saturated heterocyclic compound or as a cycloalkyl with 1 or more heteroatoms, there can be mentioned, for example: piperidine, pyrrolidine, tetrahydrofuran, morpholine, piperazine, hexahydroazepine as well as 2,6-dimethylmorpholine, N-phenylpiperazine, methoxymethylpyrrolidine, whereby the linkage with a carbon that is adjacent to the ring can be carried out with optionally present ring nitrogens.

As alkanes, alkenes and alkines for A, there can be mentioned, for example:

straight-chain or branched alkylene with 1-8 C atoms, such as: methylene, ethylene, propylene, butylene, pentylene, etc., 1-methylethylene, 1-ethylethylene, 1-methylpropylene, 2-methylpropylene, 1-methylbutylene, 2-methylbutylene, 1-ethylbutylene, 2-ethylbutylene, 1-methylpentylene, 2-methylpentylene, 3-methylpentylene, etc.

Straight-chain or branched alkenylene and alkinylene with 2-8 C atoms are alkenylene groups or alkinylene groups with double and triple bonds in all possible positions as well as with all possible methyl or ethyl substitutions. In these radicals, in each case one or two C atoms can be exchanged for O, NH, $NC_{1-3}$ alkyl or N—$C_{1-3}$ alkanoyl, whereby the exchanged group is separated from Y by at least 2 C atoms.

If two radicals are in ortho-position, they can form a common ring with the adjacent aromatic compounds. Compounds in which N, O or S atoms are bonded to olefinic or acetylenic multiple bonds or in which several N, O, S or halogen atoms are bonded to the same aliphatic carbon atom or in which N-, O- or S atoms are bonded directly to one another, are excluded, if these linkages are not explicitly defined, for example, in the functional groups or in heteroaromatic compounds that are mentioned in the claim.

Preferred are the benzimidazoles in which:

$R^1$ means a monocyclic or bicyclic $C_{6-12}$ aryl group or a monocyclic or bicyclic 5- to 10-membered heteroaryl group with 1-2 heteroatoms selected from the group that consists of N, S or O, whereby the mentioned aryl or heteroaryl group can be substituted with up to three of the following substituents, independently of one another:

F, Cl, Br, XOH, $XOR^4$, $XOCOR^4$, $XOCONHR^4$, $XOCOOR^4$, $XCOR^4$, XCN, XCOOH, $XCOOR^4$, $XCONH_2$, $XCONR^4R^{4'}$, $XCONHR^4$, XCONHOH, $XCONHOR^4$, $XCOSR^4$, $XSR^4$, $NO_2$, $XNHR^4$, $XNR^4R^{4'}$, $R^4$, whereby two substituents at $R^1$, if they are in ortho-position to one another, can be linked to one another in such a way that they jointly form methanediylbisoxy, ethane-1,2-diylbisoxy, propane-1,3-diyl, butane-1,4-diyl.

Preferred are also benzimidazoles, in which $R^2$ means a monocyclic or bicyclic $C_{6-10}$ aryl group or a monocyclic or bicyclic 5- to 10-membered heteroaryl group with 1-2 heteroatoms selected from the group that consists of N, S or O, whereby the mentioned aryl or heteroaryl group can be substituted with up to three of the following substituents, independently of one another:

F, Cl, Br, XOH, $XOR^4$, $XOCOR^4$, $XOCONHR^4$, $XOCOOR^4$, $XCOR^4$, $XC(NOH)R^4$, $XC(NOR^4)R^{4'}$, $XC(NO(COR^4))R^{4'}$, XCOOH, $XCOOR^4$, $XCONH_2$, $XCONHR^4$, $XCONR^4R^{4'}$, XCONHOH, $XCONHOR^4$, $XCOSR^4$, $XSR^4$, $XSOR^4$, $XSO_2R^4$, $SO_2NH_2$, $SO_2NHR^4$, $SO_2NR^4R^{4'}$, $NO_2$, $XNHR^4$, $XNR^4R^{4'}$, $XNHSO_2R^4$, $XN(SO_2R^4)SO_2R^{4'}$, $XNR^4SO_2R^{4'}$, $R^4$, whereby two substituents at $R^2$, if they are in ortho-position to one another, can be linked to one another in such a way that they jointly form methanediylbisoxy, ethane-1,2-diylbisoxy, propane-1,3-diyl, butane-1,4-diyl.

Also preferred are benzimidazoles of general formula I, in which $R^3$ means one or two substituents, which, independently of one another, can be:

hydrogen, F, Cl, Br, XOH, $XOR^4$, $XOCOR^4$, $XOCONHR^4$, $XOCOOR^4$, $XCOR^4$, $XC(NOH)R^4$, $XC(NOR^4)R^{4'}$, $XC(NO(COR^4))R^{4'}$, XCN, $XSR^4$, $XSOR^4$, $XSO_2R^4$, $SO_2NH_2$, $SO_2NHR^4$, $SO_2NR^4R^{4'}$, $NO_2$, $XNH_2$, $XNHR^4$, $XNR^4N^{4'}$, $XNHSO_2R^4$, $XNR^4SO_2R^{4'}$, $XN(SO_2R^4)SO_2R^{4'}$, $XNHCOR^4$, $XNHCOOR^4$, $XNHCONHR^4$, or $R^4$, whereby two substituents $R^3$, if they are in ortho-position to one another, can be linked to one another in such a way that they jointly form methanediylbisoxy, ethane-1,2-diylbisoxy, propane-1,3-diyl, or butane-1,4-diyl.

Preferred are also benzimidazoles of general formula I, in which $R^4$ and $R^{4'}$, independently of one another, mean $CF_3$, $C_2F_5$, $C_{1-4}$ alkyl, $C_{2-4}$ alkenyl, $C_{2-4}$ alkinyl, $C_{3-6}$ cycloalkyl, ($C_{1-3}$ alkyl-$C_{3-6}$ cycloalkyl), phenyl or 5- to 6-membered heteroaryl with 1-2 N, S or O atoms, whereby the phenyl and heteroaryl groups can be substituted with one or two substituents from the group that consists of F, Cl, Br, $CH_3$, $C_2H_5$, $OCH_3$, $OC_2H_5$, $CF_3$, $C_2F_5$, and in addition in a 5-membered cycloalkyl ring, a ring member can be an N or an O, and in a 6-membered cycloalkyl ring, one or two ring members can be N and/or O, whereby ring nitrogens optionally can be substituted with $C_{1-3}$ alkyl or $C_{1-3}$ alkanoyl.

Also preferred are benzimidazoles of general formula I, in which $R^5$ and $R^{5'}$, independently of one another, can be $C_{1-6}$ alkyl, whereby a carbon atom can be exchanged for O, NH, $NC_{1-3}$ alkyl, $NC_{1-3}$ alkanoyl, $C_{3-7}$ cycloalkyl-$C_{0-3}$ alkyl, whereby in a 5-membered cycloalkyl ring, a ring member can be an N or an O, and in a 6- or 7-membered cycloalkyl ring, one or two ring members can be N and/or O, whereby ring nitrogens optionally can be substituted with $C_{1-3}$ alkyl or $C_{1-3}$ alkanoyl, whereby the mentioned $C_{1-6}$ alkyl part can be substituted with one of the previously mentioned cycloalkyls or else a 5- to 6-membered heteroaromatic compound with 1-2 heteroatoms, selected from N, S or O, whereby all previously mentioned alkyl and cycloalkyl parts can be substituted with up to two substituents that consist of $CF_3$, OH, $OC_{1-3}$ alkyl, and the previously mentioned heteroaryl groups with one or two substituents that consist of F, Cl, CF$_3$, CH$_3$, C$_2$H$_5$, OCH$_3$, OC$_2$H$_5$ or R$^5$ and R$^{5'}$ together with the nitrogen atom form a 5- to 7-membered heterocyclic compound, which can contain another oxygen, nitrogen or sulfur atom and can be substituted with C$_{1-4}$ alkyl, C$_{1-4}$ alkoxy-C$_{0-2}$ alkyl, C$_{1-4}$ alkoxy-carbonyl, aminocarbonyl or phenyl.

Preferred are also benzimidazoles of general formulae I, in which

A means C$_{1-10}$ alkanediyl, C$_{2-10}$ alkenediyl, C$_{2-10}$ alkinediyl, (C$_{0-5}$ alkanediyl-C$_{3-7}$ cycloalkanediyl-C$_{0-5}$ alkanediyl), whereby in a 5-membered cycloalkyl ring, a ring member can be an N or an O, or in a 6- or 7-membered cycloalkyl ring, one or two ring members can be N and/or O, whereby ring nitrogens optionally can be substituted with C$_{1-3}$ alkyl or C$_{1-3}$ alkanoyl, whereby in the above-mentioned aliphatic chains, a carbon atom or two carbon atoms can be exchanged for O, NH, NC$_{1-3}$ alkyl, or NC$_{1-3}$ alkanoyl.

Also preferred are benzimidazoles of general formula I, in which

B means COOH, COOR$^5$, CONH$_2$, CONHR$^5$, CONR$^5$R$^{5'}$, CONHOH, CONHOR$^5$ or tetrazolyl, in each case bonded to a carbon atom of group A.

B in the meaning of COOR$^5$, CONH$_2$, CONHR$^5$, CONR$^5$ or R$^{5'}$ is especially preferred.

Preferred are also benzimidazoles of general formula I, in which

X means a bond or methylene.

Preferred are also benzimidazoles of general formula I, in which

Y means O.

In particular, R$^1$ and R$^2$, independently of one another, mean phenyl or 5- to 6-membered heteroaryl, with 1-2 heteroatoms such as N, O or S atoms, which can be substituted with F, Cl, Br, cyano, C$_{1-4}$ alkyl, C$_{1-4}$ alkoxy, methylenedioxy, C$_{1-4}$ alkylthio, NO$_2$, CF$_3$, NH$_2$, NH (C$_{1-3}$ alkyl), N(C$_{1-3}$ alkyl)$_2$.

The meaning of H, F, Cl, OH, C$_{1-4}$ alkoxy, C$_{1-4}$ alkyl, NO$_2$, NH$_2$, NH—C$_{1-4}$ alkanoyl NH—SO$_2$-benzyl or NH—SO$_2$-phenyl, whereby the phenyl radical can be substituted with F, Cl, BR, C$_{1-4}$ alkyl, C$_{1-4}$ alkoxy, CF$_3$ or acetylamino, is especially preferred for R$^3$.

Especially preferred are the following benzimidazoles:

[(1,2-Diphenyl-1H-benzimidazol-6-yl)oxy]acetic acid isopropyl ester
3-[(1,2-diphenyl-1H-benzimidazol-6-yl)oxy]propanoic acid methyl ester
2-[(1,2-diphenyl-1H-benzimidazol-6-yl)oxy]propanoic acid methyl ester
4-[(1,2-diphenyl-1H-benzimidazol-6-yl)oxy]butanoic acid isopropyl ester
5-[(1,2-diphenyl-1H-benzimidazol-6-yl)oxy]pentanoic acid isopropyl ester
6-[(1,2-diphenyl-1H-benzimidazol-6-yl)oxy]hexanoic acid methyl ester
6-[(1,2-diphenyl-1H-benzimidazol-6-yl)oxy]hexanoic acid isopropyl ester
6-[(1,2-diphenyl-1H-benzimidazol-6-yl)oxy]hexanamide
N-methoxy-6-[(1,2-diphenyl-1H-benzimidazol-6-yl)oxy]hexanamide
N-(phenylmethoxy)-6-[(1,2-diphenyl-1H-benzimidazol-6-yl)oxy]hexanamide
N-hydroxy-6-[(1,2-diphenyl-1H-benzimidazol-6-yl)oxy]hexanamide
7-[(1,2-diphenyl-1H-benzimidazol-6-yl)oxy]heptanoic acid methyl ester
6-[[1-(3-nitrophenyl)-2-phenyl-1H-benzimidazol-6-yl]oxy]hexanoic acid isopropyl ester
6-[[2-phenyl-1-[3-(trifluoromethyl)phenyl]-1H-benzimidazol-6-yl]oxy]hexanoic acid methyl ester
6-[[2-phenyl-1-[3-(trifluoromethyl)phenyl]-1H-benzimidazol-6-yl]oxy]hexanoic acid isopropyl ester
6-[[1-(3-cyanophenyl)-2-phenyl-1H-benzimidazol-6-yl]oxy]hexanoic acid methyl ester
6-[[1-(3-cyanophenyl)-2-phenyl-1H-benzimidazol-6-yl]oxy]hexanoic acid isopropyl ester
6-[[1-(3-cyanophenyl)-2-phenyl-1H-benzimidazol-6-yl]oxy]hexanoic acid
6-[[1-(4-cyanophenyl)-2-phenyl-1H-benzimidazol-6-yl]oxy]hexanoic acid methyl ester
6-[[1-(4-cyanophenyl)-2-phenyl-1H-benzimidazol-6-yl]oxy]hexanoic acid isopropyl ester
6-[[1-(3-chlorophenyl)-2-phenyl-1H-benzimidazol-6-yl]oxy]hexanoic acid methyl ester
6-[[1-(3-chlorophenyl)-2-phenyl-1H-benzimidazol-6-yl]oxy]hexanoic acid isopropyl ester
6-[[1-(4-chlorophenyl)-2-phenyl-1H-benzimidazol-6-yl]oxy]hexanoic acid methyl ester
6-[[1-(4-chlorophenyl)-2-phenyl-1H-benzimidazol-6-yl]oxy]hexanoic acid isopropyl ester
6-[[1-(3-methylphenyl)-2-phenyl-1H-benzimidazol-6-yl]oxy]hexanoic acid methyl ester
6-[[1-(3-methylphenyl)-2-phenyl-1H-benzimidazol-6-yl]oxy]hexanoic acid isopropyl ester
6-[[1-(4-methylphenyl)-2-phenyl-1H-benzimidazol-6-yl]oxy]hexanoic acid methyl ester
6-[[1-(4-methylphenyl)-2-phenyl-1H-benzimidazol-6-yl]oxy]hexanoic acid isopropyl ester
6-[[1-(3,4-dimethylphenyl)-2-phenyl-1H-benzimidazol-6-yl]oxy]hexanoic acid methyl ester
6-[[1-(3,5-dimethylphenyl)-2-phenyl-1H-benzimidazol-6-yl]oxy]hexanoic acid methyl ester
6-[[1-(3,5-dimethylphenyl)-2-phenyl-1H-benzimidazol-6-yl]oxy]hexanoic acid isopropyl ester
6-[[1-(3-methoxyphenyl)-2-phenyl-1H-benzimidazol-6-yl]oxy]hexanoic acid methyl ester
6-[[1-(4-methoxyphenyl)-2-phenyl-1H-benzimidazol-6-yl]oxy]hexanoic acid methyl ester
6-[[1-(3,4-dimethoxyphenyl)-2-phenyl-1H-benzimidazol-6-yl]oxy]hexanoic acid methyl ester
6-[[1-[3,4-(methylenedioxy)phenyl]-2-phenyl-1H-benzimidazol-6-yl]oxy]hexanoic acid methyl ester
6-[[1-[3,4-(methylenedioxy)phenyl]-2-phenyl-1H-benzimidazol-6-yl]oxy]hexanoic acid
6-[[2-phenyl-1-(3,4,5-trimethoxyphenyl)-1H-benzimidazol-6-yl]oxy]hexanoic acid methyl ester
6-[[2-phenyl-1-(3,4,5-trimethoxyphenyl)-1H-benzimidazol-6-yl]oxy]hexanoic acid
6-[[2-phenyl-1-(3,4,5-trimethoxyphenyl)-1H-benzimidazol-6-yl]oxy]hexanoic acid isopropyl ester
6-[[1-[4-(N,N-dimethylamino)phenyl]-2-phenyl-1H-benzimidazol-6-yl]oxy]hexanoic acid methyl ester
6-[[1-[4-(N,N-dimethylamino)phenyl]-2-phenyl-1H-benzimidazol-6-yl]oxy]hexanoic acid
6-[[1-phenyl-2-[3-(trifluoromethyl)phenyl]-1H-benzimidazol-6-yl]oxy]hexanoic acid isopropyl ester
6-[[2-(3-chlorophenyl)-1-phenyl-1H-benzimidazol-6-yl]oxy]hexanoic acid methyl ester
6-[[2-(3-chlorophenyl)-1-phenyl-1H-benzimidazol-6-yl]oxy]hexanoic acid isopropyl ester 6-[[2-(4-chlorophenyl)-1-phenyl-1H-benzimidazol-6-yl] oxy]hexanoic acid methyl ester
6-[[2-(4-chlorophenyl)-1-phenyl-1H-benzimidazol-6-yl] oxy]hexanoic acid isopropyl ester
6-[[2-(4-methylphenyl)-1-phenyl-1H-benzimidazol-6-yl] oxy]hexanoic acid methyl ester
6-[[2-(4-methylphenyl)-1-phenyl-1H-benzimidazol-6-yl] oxy]hexanoic acid isopropyl ester
6-[[1-phenyl-2-(4-pyridinyl)-1H-benzimidazol-6-yl]oxy] hexanoic acid methyl ester
6-[(1,2-diphenyl-5-nitro-1H-benzimidazol-6-yl)oxy]hexanoic acid methyl ester
6-[(1,2-diphenyl-5-nitro-1H-benzimidazol-6-yl)oxy]hexanoic acid isopropyl ester
6-[[5-[[(4-bromophenyl)sulfonyl]amino]-1,2-diphenyl-1H-benzimidazol-6-yl]oxy]hexanoic acid isopropyl ester
6-[[5-[[(4-chlorophenyl)sulfonyl]amino]-1,2-diphenyl-1H-benzimidazol-6-yl]oxy]hexanoic acid methyl ester
6-[[5-[[(4-chlorophenyl)sulfonyl]amino]-1,2-diphenyl-1H-benzimidazol-6-yl]oxy]hexanoic acid isopropyl ester
6-[[1,2-diphenyl-5-[[(3-methylphenyl)sulfonyl]amino]-1H-benzimidazol-6-yl]oxy]hexanoic acid isopropyl ester
6-[[1,2-diphenyl-5-[[(4-methylphenyl)sulfonyl]amino]-1H-benzimidazol-6-yl]oxy]hexanoic acid isopropyl ester
6-[[1,2-diphenyl-5-[[(4-methoxyphenyl)sulfonyl]amino]-1H-benzimidazol-6-yl]oxy]hexanoic acid isopropyl ester
6-[[1,2-diphenyl-5-[[[(4-trifluoromethyl)phenyl]sulfonyl] amino]-1H-benzimidazol-6-yl]oxy]hexanoic acid isopropyl ester
6-[[5-[[[4-(acetylamino)phenyl]sulfonyl]amino]-1,2-diphenyl-1H-benzimidazol-6-yl]oxy]-hexanoic acid isopropyl ester
6-[[5-[[bis(3-chlorophenyl)sulfonyl]amino]-1,2-diphenyl-1H-benzimidazol-6-yl]oxy]hexanoic acid isopropyl ester
6-[[1,2-diphenyl-5-[(propylsulfonyl)amino]-1H-benzimidazol-6-yl]oxy]hexanoic acid isopropyl ester
6-[[5-[(benzylsulfonyl)amino]-1,2-diphenyl-1H-benzimidazol-6-yl]oxy]hexanoic acid isopropyl ester
2-[2-[(1,2-diphenyl-1H-benzimidazol-6-yl)oxy]ethoxy]acetic acid methyl ester
3-[2-[(1,2-diphenyl-1H-benzimidazol-6-yl)oxy]ethoxy]propanoic acid methyl ester
6-[[1-(3-nitrophenyl)-2-phenyl-1H-benzimidazol-6-yl]oxy] hexanoic acid ethyl ester
6-[[4-acetyl-1-(4-methylphenyl)-2-phenyl-1H-benzimidazol-6-yl]oxy]hexanoic acid methyl ester
6-[[1-(4-methylphenyl)-2-phenyl-1H-benzimidazol-5-yl] oxy]hexanoic acid methyl ester
6-[[2-phenyl-1-[4-(thiomethyl)phenyl]-1H-benzimidazol-5-yl]oxy]hexanoic acid methyl ester
6-[[2-phenyl-1-[4-(thiomethyl)phenyl]-1H-benzimidazol-6-yl]oxy]hexanoic acid methyl ester
6-[[2-phenyl-1-(3-thienyl)-1H-benzimidazol-5-yl]oxy]hexanoic acid methyl ester
6-[[2-phenyl-1-(3-thienyl)-1H-benzimidazol-6-yl]oxy]hexanoic acid methyl ester
4-[(1,2-diphenyl-1H-benzimidazol-6-yl)oxy]butanoic acid methyl ester
N-(phenylmethoxy)-6-[[2-phenyl-1-(3,4,5-trimethoxyphenyl)-1H-benzimidazol-6-yl]oxy]-hexanamide
N,N-dimethyl-6-[(1,2-diphenyl-1H-benzimidazol-6-yl)oxy] hexanamide
N-isopropyl-6-[(1,2-diphenyl-1H-benzimidazol-6-yl)oxy] hexanamide
6-[(1,2-diphenyl-1H-benzimidazol-6-yl)oxy]-1-pyrrolidin-1-ylhexan-1-one 5-[[5-[[(4-chlorophenyl)sulfonyl]amino]-1,2-diphenyl-1H-benzimidazol-6-yl]oxy]pentanoic acid methyl ester
6-[[5-[[(4-chlorophenyl)sulfonyl]amino]-1-(4-methylphenyl)-2-phenyl-1H-benzimidazol-6-yl]oxy]hexanoic acid methyl ester
6-[[5-[[(4-chlorophenyl)sulfonyl]amino]-1-(4-methoxyphenyl)-2-phenyl-1H-benzimidazol-6-yl]oxy]hexanoic acid methyl ester
6-[[4-(acetyloxy)-1-(4-methylphenyl)-2-phenyl-1H-benzimidazol-6-yl]oxy]hexanoic acid methyl ester
6-[[4-hydroxy-1-(4-methylphenyl)-2-phenyl-1H-benzimidazol-6-yl]oxy]hexanoic acid methyl ester
6-[[4-hydroxy-1-(4-methylphenyl)-2-phenyl-1H-benzimidazol-6-yl]oxy]hexanoic acid
-6-[[7-methyl-1-(4-methylphenyl)-2-phenyl-1H-benzimidazol-6-yl]oxy]hexanoic acid methyl ester
6-[[2-phenyl-1-(3-pyridyl)-1H-benzimidazol-5-yl]oxy]hexanoic acid methyl ester
6-[[2-phenyl-1-(3-pyridyl)-1H-benzimidazol-6-yl]oxy]hexanoic acid methyl ester
6-[[2-phenyl-1-(4-pyridyl)-1H-benzimidazol-6-yl]oxy]hexanoic acid methyl ester
6-[[2-(4-fluoro-phenyl)-1-phenyl-1H-benzimidazol-6-yl] oxy]hexanoic acid methyl ester
6-[[2-(4-methoxyphenyl)-1-phenyl-1H-benzimidazol-6-yl] oxy]-hexanoic acid methyl ester
6-[[2-(4-bromophenyl)-1-phenyl-1H-benzimidazol-6-yl] oxy]hexanoic acid methyl ester
6-[[2-[4-(trifluoromethyl)phenyl]-1-phenyl-1H-benzimidazol-6-yl]oxy]hexanoic acid methyl ester
6-[[1-phenyl-2-(benzothien-2-yl)-1H-benzimidazol-6-yl] oxy]hexanoic acid methyl ester
6-[[1-phenyl-2-(benzothien-2-yl)-1H-benzimidazol-6-yl] oxy]hexanoic acid
6-[[5-hydroxy-1-(4-methylphenyl)-2-phenyl-1H-benzimidazol-6-yl]oxy]hexanoic acid isopropyl ester
6-[[5-hydroxy-1-(4-methylphenyl)-2-phenyl-1H-benzimidazol-6-yl]oxy]hexanoic acid
6-[[5-methoxy-1-(4-methylphenyl)-2-phenyl-1H-benzimidazol-6-yl]oxy]hexanoic acid isopropyl ester
6-[[5-hydroxy-1-(4-methylphenyl)-2-phenyl-1H-benzimidazol-6-yl]oxy]hexanoic acid methyl ester
6-[[5-methoxy-1-(4-methylphenyl)-2-phenyl-1H-benzimidazol-6-yl]oxy]hexanoic acid methyl ester
6-[[5-[[(4-chlorophenyl)sulfonyl]amino]-1-(3,4-dimethylphenyl)-2-phenyl-1H-benzimidazol-6-yl]oxy]hexanoic acid methyl ester benzimidazol-6-yl]oxy]hexanoic acid methyl ester
6-[[5-[[(4-chlorophenyl)sulfonyl]amino]-2-(4-fluorophenyl)-1-(4-methoxyphenyl)-1H-benzimidazol-6-yl]oxy] hexanoic acid methyl ester
6-[[5-[[(4-chlorophenyl)sulfonyl]amino]-1-(4-methoxyphenyl)-2-(4-methoxyphenyl)-1H-benzimidazol-6-yl]oxy] hexanoic acid methyl ester
4-[[5-[[(4-chlorophenyl)sulfonyl]amino]-1-(4-methoxyphenyl)-2-phenyl-1H-benzimidazol-6-yl]oxy]butanoic acid methyl ester
5-[[5-[[(4-chlorophenyl)sulfonyl]amino]-1-(4-methoxyphenyl)-2-phenyl-1H-benzimidazol-6-yl]oxy]pentanoic acid methyl ester
5-[[5-[[(4-chlorophenyl)sulfonyl]amino]-1,2-diphenyl-1H-benzimidazol-6-yl]oxy]pentanoic acid methyl ester
6-[[5-[[(4-(trifluoromethyl)phenyl)sulfonyl]amino]-1-(4-methoxyphenyl)-2-phenyl-1H-benzimidazol-6-yl]oxy] hexanoic acid methyl ester 6-[[5-[[(4-chlorophenyl)sulfonyl]methylamino]-1-(4-methoxyphenyl)-2-phenyl-1H-benzimidazol-6-yl]oxy]hexanoic acid methyl ester
6-[[1-(indan-5-yl)-2-phenyl-1H-benzimidazol-6-yl]oxy] hexanoic acid methyl ester
6-[[1-(indan-5-yl)-2-phenyl-1H-benzimidazol-6-yl]oxy] hexanoic acid
6-[[1-(3-fluorophenyl)-2-phenyl-1H-benzimidazol-6-yl]oxy]hexanoic acid methyl ester
6-[[2-(4-nitrophenyl)-1-phenyl-1H-benzimidazol-6-yl]oxy] hexanoic acid methyl ester
6-[[1-phenyl-2-(3-pyridinyl)-1H-benzimidazol-6-yl]oxy] hexanoic acid methyl ester
N-(cyclopropylmethoxy)-6-[(1,2-diphenyl-1H-benzimidazol-6-yl)oxy]hexanamide
N-isobutoxy-6-[(1,2-diphenyl-1H-benzimidazol-6-yl)oxy] hexanamide
N-(cyclopropylmethoxy)-6-[2-phenyl-1-(3,4,5-trimethoxyphenyl)-1H-benzimidazol-6-yl)oxy]-hexanamide
N-isobutoxy-6-[2-phenyl-1-(3,4,5-trimethoxyphenyl)-1H-benzimidazol-6-yl)oxy]hexanamide
N-(2-methoxyethyl)-6-[(1,2-diphenyl-1H-benzimidazol-6-yl)oxy]hexanamide
N-(3-methoxypropyl)-6-[(1,2-diphenyl-1H-benzimidazol-6-yl)oxy]hexanamide
N-isobutyl-6-[(1,2-diphenyl-1H-benzimidazol-6-yl)oxy] hexanamide
6-[(1,2-diphenyl-1H-benzimidazol-6-yl)oxy]-1-morpholin-1-ylhexan-1-one
N,N-di(-2-methoxyethyl)-6-[(1,2-diphenyl-1H-benzimidazol-6-yl)oxy]hexanamide
N-isopentyl-6-[(1,2-diphenyl-1H-benzimidazol-6-yl)oxy] hexanamide
N-(pyridin-2-yl)-6-[(1,2-diphenyl-1H-benzimidazol-6-yl)oxy]hexanamide
N-(pyridin-3-yl)-6-[(1,2-diphenyl-1H-benzimidazol-6-yl)oxy]hexanamide
N-isopropyl-6-[[1-(3,4-dimethylphenyl)-2-phenyl-1H-benzimidazol-6-yl]oxy]hexanamide
N,N-dimethyl-6-[[1-(3,4-dimethylphenyl)-2-phenyl-1H-benzimidazol-6-yl]oxy]hexanamide
N,N-diethyl-6-[[1-(3,4-dimethylphenyl)-2-phenyl-1H-benzimidazol-6-yl]oxy]hexanamide
N-isobutyl-6-[[1-(3,4-dimethylphenyl)-2-phenyl-1H-benzimidazol-6-yl]oxy]hexanamide
N-cyclopropyl-6-[[1-(3,4-dimethylphenyl)-2-phenyl-1H-benzimidazol-6-yl]oxy]hexanamide
N-cyclobutyl-6-[[1-(3,4-dimethylphenyl)-2-phenyl-1H-benzimidazol-6-yl]oxy]hexanamide
N-tert-butyl-6-[[1-(3,4-dimethylphenyl)-2-phenyl-1H-benzimidazol-6-yl]oxy]hexanamide
(R)-6-[[1-(3,4-dimethylphenyl)-2-phenyl-1H-benzimidazol-6-yl]oxy]1-(2-methoxymethyl)-pyrrolidin-1-ylhexan-1-one
N-(3-imidazol-1-yl-propyl)-6-[[1-(3,4-dimethylphenyl)-2-phenyl-1H-benzimidazol-6-yl]oxy]hexanamide
N-(2-pyridin-2-ylethyl)-6-[[1-(3,4-dimethylphenyl)-2-phenyl-1H-benzimidazol-6-yl]oxy]hexanamide
N-(3-methoxypropyl)-6-[[1-(indan-5-yl)-2-phenyl-1H-benzimidazol-6-yl]oxy]heptanamide
6-[[1-(4-methylphenyl)-2-(3-pyridyl)-1H-benzimidazol-6-yl]oxy]hexanoic acid methyl ester
6-[[1-(4-methylphenyl)-2-(4-pyridyl)-1H-benzimidazol-6-yl]oxy]hexanoic acid methyl ester
6-[[1-(4-methylphenyl)-2-(2-thienyl)-1H-benzimidazol-6-yl]oxy]hexanoic acid methyl ester
6-[[1-(4-methylphenyl)-2-(3-thienyl)-1H-benzimidazol-6-yl]oxy]hexanoic acid methyl ester
6-[[2-(3-indolyl)-1-(4-methylphenyl)-1H-benzimidazol-6-yl]oxy]hexanoic acid methyl ester
6-[[1-(4-methylphenyl)-2-(2-furyl)-1H-benzimidazol-6-yl] oxy]hexanoic acid methyl ester
6-[[1-(4-methylphenyl)-2-(3-furyl)-1H-benzimidazol-6-yl] oxy]hexanoic acid methyl ester
6-[[1-(4-methylphenyl)-2-(5-methyl-2-thienyl) 1H benzimidazol-6-yl]oxy]hexanoic acid methyl ester
6-[[1-(4-methylphenyl)-2-(3-methyl-2-thienyl)-1H-benzimidazol-6-yl]oxy]hexanoic acid methyl ester.

The benzimidazole derivatives according to the invention inhibit the activation of microglia and can therefore be used for the production of a pharmaceutical agent for treatment or prevention of diseases that are associated with microglia. Microglia are defined here as the macrophages of the brain.

This action is surprising since to date benzimidazole derivatives had been described only for the treatment of thromboses and arteriosclerosis (EP0531883, WO98/07263, EP0104727, WO97/12613), cystitis (WO97/33873) and diseases that are linked to a β-amyloid peptide (U.S. Pat. No. 5,552,426) and increased activation of Ca-channels (EP520200), but an effect on microglia is not known.

The invention also relates to the use of a benzimidazole of general formula II

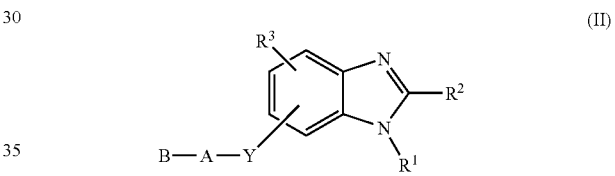

(II)

in which
  $R^1$ means a monocyclic or bicyclic $C_{6-12}$ aryl group or a monocyclic or bicyclic 5- to 10-membered heteroaryl group with 1-4 heteroatoms selected from the group that consists of N, S or O, whereby the mentioned aryl or heteroaryl group can be substituted with up to three of the following substituents, independently of one another:
    F, Cl, Br, I, C(NH)NH$_2$, C(NH)NHR$^4$, C(NH)NR$^4$R$^{4'}$, C(NR$^4$)NH$_2$, C(NR$^4$)NHR$^{4'}$, C(NR$^4$)NR$^4$R$^{4'}$, XOH, XOR$^4$, XOCOR$^4$, XOCONHR$^4$, XOCOOR$^4$, XOCR$^4$, XC(NOH)R$^4$, XC(NOR$^4$)R$^{4'}$, XC(NO(COR$^4$))R$^{4'}$, XCN, XCOOH, XCOOR$^4$, XCONH$_2$, XCONR$^4$R$^{4'}$, XCONHR$^4$, XCONHOH, XCONHOR$^4$, XCOSR$^4$, XSR$^4$, XSOR$^4$, XSO$_2$R$^4$, SO$_2$NH$_2$, SO$_2$NHR$^4$, SO$_2$NR$^4$R$^{4'}$, NO$_2$, XNH$_2$, XNHR$^4$, XNR$^4$R$^{4'}$, XNHSO$_2$R$^4$, XN(SO$_2$R$^4$)(SO$_2$R$^{4'}$), XNR$^4$SO$_2$R$^{4'}$, XNHCOR$^4$, XNHCOOR$^4$, XNHCONHR$^4$, tetrahydro-2,5-dioxopyrrol-1-yl, 2,5-dihydro-2,5-dioxopyrrol-1-yl, 2,7-dihydro-2,7-dioxoisoindol-1-yl, R$^4$, whereby two substituents at R$^1$, if they are in ortho-position to one another, can be linked to one another in such a way that they jointly form methanediylbisoxy, ethane-1,2-diylbisoxy, propane-1,3-diyl, butane-1,4-diyl,
  $R^2$ means a monocyclic or bicyclic $C_{6-10}$ aryl group or a monocyclic or bicyclic 5- to 10-membered heteroaryl group with 1-4 heteroatoms selected from the group that consists of N, S or O, whereby the mentioned aryl or heteroaryl group can be substituted with up to three of the following substituents, independently of one another:

F, Cl, Br, I, C(NH)NH$_2$, C(NH)NHR$^4$, C(NH)NR$^4$R$^{4'}$, C(NR$^4$)NH$_2$, C(NR$^4$)NHR$^{4'}$, C(NR$^4$)NR$^4$R$^{4'}$, XOH, XOR$^4$, XOCOR$^4$, XOCONHR$^4$, XOCOOR$^4$, XCOR$^4$, XC(NOH)R$^4$, XC(NOR$^4$)R$^{4'}$, XC(NO(COR$^4$))R$^{4'}$, XCN, XCOOH, XCOOR$^4$, XCONH$_2$, XCONR$^4$R$^{4'}$, XCONHR$^4$, XCONHOH, XCONHOR$^4$, XCOSR$^4$, XSR$^4$, XSOR$^4$, XSO$_2$R$^4$, SO$_2$NH$_2$, SO$_2$NHR$^4$, SO$_2$NR$^4$R$^{4'}$, NO$_2$, XNH$_2$, XNHR$^4$, XNR$^4$R$^{4'}$, XNHSO$_2$R$^4$, XN(SO$_2$R$^4$)(SO$_2$R$^{4'}$), XNR$^4$SO$_2$R$^{4'}$, XNHCOR$^4$, XNHCOOR$^4$, XNHCONHR$^4$, tetrahydro-2,5-dioxopyrrol-1-yl, 2,5-dihydro-2,5-dioxopyrrol-1-yl, 2,7-dihydro-2,7-dioxoisoindol-1-yl, R$^4$, whereby two substituents at R$^2$, if they are in ortho-position to one another, can be linked to one another in such a way that they jointly form methanediylbisoxy, ethane-1,2-diylbisoxy, propane-1,3-diyl, butane-1,4-diyl, R$^3$ stands for one or two substituents, that mean, independently of one another:
hydrogen, F, Cl, Br, I, XOH, XOR$^4$, XOCOR$^4$, XOCONHR$^4$, XOCOOR$^4$, XCOR$^4$, XC(NOH)R$^4$, XC(NOR$^4$)R$^{4'}$, XC(NO(COR$^4$))R$^{4'}$, XCN, XCOOH, XCOOR$^4$, XCONH$_2$, XCONHR$^4$, XCONR$^4$R$^{4'}$, XCONHOH, XCONHOR$^4$, XCOSR$^4$, XSR$^4$, XSOR$^4$, XSO$_2$R$^4$, SO$_2$NH$_2$, SO$_2$NHR$^4$, SO$_2$NR$^4$R$^{4'}$, NO$_2$, XNH$_2$, XNHR$^4$, XNR$^4$R$^{4'}$, XNHSO$_2$R$^4$, XNR$^4$SO$_2$R$^{4'}$, XN(SO$_2$R$^4$)(SO$_2$R$^{4'}$), XNHCOR$^4$, XNHCOOR$^4$, XNHCONHR$^4$, tetrahydro-2,5-dioxopyrrol-1-yl, 2,5-dihydro-2,5-dioxopyrrol-1-yl, 2,7-dihydro-2,7-dioxoisoindol-1-yl, R$^4$, whereby two substituents R$^3$, if they are in ortho-position to one another, can be linked to one another in such a way that they jointly form methanediylbisoxy, ethane-1,2-diylbisoxy, propane-1,3-diyl, butane-1,4-diyl, R$^4$ and R$^{4'}$, independently of one another, mean C$_{1-4}$ perfluoroalky, C$_{1-6}$ alkyl, C$_{2-6}$ alkenyl, C$_{2-6}$ alkinyl, C$_{3-7}$ cycloalkyl, (C$_{1-3}$ alkyl-C$_{3-7}$ cycloalkyl), C$_{1-3}$ alkyl-C$_{6-10}$ aryl, C$_{1-3}$ alkyl 5- to 10-membered heteroaryl with 1-4 N, S or O atoms heteroaryl, C$_{6-10}$ aryl or 5- to 10-membered heteroaryl with 1-4 N, S or O atoms, whereby the C$_{6-10}$ aryl and heteroaryl groups can be substituted with one or two substituents from the group that consists of F, Cl, Br, CH$_3$, C$_2$H$_5$, NO$_2$, OCH$_3$, OC$_2$H$_5$, CF$_3$, C$_2$F$_5$ or else can carry an annelated methanediylbisoxy group or ethane-1,2-diylbisoxy group, whereby in a 5-membered cycloalkyl ring, a ring member can be an N or an O, and in a 6- or 7-membered cycloalkyl ring, one or two ring members can be N or O, whereby ring nitrogens optionally can be substituted with C$_{1-3}$ alkyl or C$_{1-3}$ alkanoyl, R$^5$ and R$^{5'}$, independently of one another, mean hydrogen, C$_{1-6}$ alkyl, C$_{2-6}$ alkenyl, C$_{2-6}$ alkinyl, whereby a carbon atom can be exchanged for O, S, SO, SO$_2$, NH, NC$_{1-3}$ alkyl or NC$_{1-3}$ alkanoyl, C$_{3-7}$ cycloalkyl-C$_{0-3}$ alkyl, whereby in a 5-membered cycloalkyl ring, a ring member can be an N or an O and in a 6- or 7-membered cycloalkyl ring, one or two ring members can be N and/or O, whereby ring nitrogens optionally can be substituted with C$_{1-3}$ alkyl or C$_{1-3}$ alkanoyl, C$_{6-10}$ aryl or 5- to 10-membered heteroaryl with 1-4 heteroatoms from N, S, and O, whereby the mentioned alkyl, alkenyl, and alkinyl chains can be substituted with one of the previously mentioned cycloalkyls, aryls or heteroaryls, whereby all previously mentioned alkyl and cycloalkyl radicals with up to two substituents consisting of CF$_3$, C$_2$F$_5$, OH, OC$_{1-3}$ alkyl, NH2, NHC$_{1-3}$ alkyl, NHC$_{1-3}$ alkanoyl, N(C$_{1-3}$ alkyl)$_2$N(C$_{1-3}$ alkyl) (C$_{1-3}$ alkanoyl), COOH, CONH$_2$, COOC$_{1-3}$ alkyl and all previously mentioned aryl and heteroaryl groups can be substituted with one or two substituents from the group that consists of F, Cl, Br, CH$_3$, C$_2$H$_5$, NO$_2$, OCH$_3$, OC$_2$H$_5$, CF$_3$, C$_2$F$_5$ or else can carry an annelated methanediylbisoxy, ethane-1,2-diylbisoxy group, or R$^5$ and R$^{5'}$ together with the nitrogen atom form a 5- to 7-membered heterocyclic compound, which can contain another oxygen, nitrogen or sulfur atom and can be substituted with C$_{1-4}$ alkyl, C$_{1-4}$ alkoxy-C$_{0-2}$ alkyl, C$_{1-4}$ alkoxy-carbonyl, aminocarbonyl or phenyl, A means C$_{1-10}$ alkanediyl, C$_{2-10}$ alkenediyl, C$_{2-10}$ alkinediyl, (C$_{0-5}$ alkanediyl-C$_{3-7}$ cycloalkanediyl-C$_{0-5}$ alkanediyl), (C$_{0-5}$ alkanediylarylene-C$_{0-5}$ alkanediyl), (C$_{0-5}$ alkanediyl-heteroarylene-C$_{0-5}$ alkanediyl), whereby the aryl and heteroaryl groups can be substituted with one or two substituents that consist of F, Cl, Br, CH$_3$, C$_2$H$_5$, NO$_2$, OCH$_3$, OC$_2$H$_5$, CF$_3$, C$_2$F$_5$, whereby in a 5-membered cycloalkyl ring, a ring member can be an N or an O, and in a 6- or 7-membered cycloalkyl ring, one or two ring members can be N and/or O, whereby ring nitrogens optionally can be substituted with C$_{1-3}$ alkyl or C$_{1-3}$ alkanoyl, whereby in the mentioned aliphatic chains, a carbon atom or two carbon atoms can be exchanged for O, NH, NR$^4$, NCOR$^4$, NSO$_2$R$^4$, and whereby alkyl or cycloalkyl groups can be substituted with up to two substituents consisting of F, OH, OR$^4$, OCOR$^4$, =O, NH$_2$, NR$^4$R$^{4'}$, NHCOR$^4$, NHCOOR$^4$, NHCONHR$^4$, NHSO$_2$R$^4$SH, SR$^4$, B means hydrogen, OH, OCOR$^5$, OCONHR$^5$, OCOOR$^5$, COR$^5$, C(NOH)R$^5$, C(NOR$^5$)R$^{5'}$, C(NO(COR$^5$))R$^{5'}$, COOH, COOR$^5$, CONH$_2$, CONHNH$_2$, CONHR$^5$, CONR$^5$R$^{5'}$, CONHOH, CONHOR$^5$, SO$_3$H, SO$_2$NH$_2$, SO$_2$NHR$^5$, SO$_2$NR$^5$R$^{5'}$, PO$_3$H, PO(OH)(OR$^5$), PO(OR$^5$)(OR$^{5'}$), PO(OH)(NHR$^5$), PO(NHR$^5$)(NHR$^{5'}$), tetrazolyl, respectively bonded to a carbon atom of group A, or the entire group Y-A-B N(SO$_2$R$^4$)(SO$_2$R$^4$) or NHSO$_2$R$^4$, X means a bond, CH$_2$, (CH$_2$)$_2$, CH(CH$_3$), (CH$_2$)$_3$, CH(CH$_2$CH$_3$), CH(CH$_3$)CH$_2$, CH$_2$CH(CH$_3$), Y means a bond, O, S, SO, SO$_2$, NH, NR$^4$, NCOR$^4$, NSO$_2$R$^4$, for the production of a pharmaceutical agent for treating or preventing diseases that are associated with a microglia activation.

In addition to the new compounds of general formula I, general formula II also comprises known compounds (EP 0 531 883, DE 4330959). The compounds of general formula II according to the invention inhibit the activation of the microglia activation. This action is also new for the known compounds.

Preferred is the use of compounds of general formula II, whereby

R$^1$ means a monocyclic or bicyclic aryl group or a monocyclic or bicyclic 5- to 10-membered heteroaryl group with 1-2 heteroatoms selected from the group that consists of N, S or O, whereby the mentioned aryl or heteroaryl group can be substituted with up to three of the following substituents, independently of one another:

F, Cl, Br, XOH, XOR$^4$, XOCOR$^4$, XOCONHR$^4$, XOCOOR$^4$, XCOR$^4$, XCN, XCOOH, XCOOR$^4$, XCONH$_2$, XCONR$^4$R$^{4'}$, XCONHR$^4$, XCONHOH, XCONHOR$^4$, XCOSR$^4$, XSR$^4$, NO$_2$, XNHR$^4$,

XNR$^4$R$^{4'}$, R$^4$, whereby two substituents at R$^1$, if they are in ortho-position to one another, can be linked to one another in such a way that they jointly form methanediylbisoxy, ethane-1,2-diylbisoxy, propane-1,3-diyl, butane-1,4-diyl.

Also preferred is the use of compounds of general formula II, whereby

R$^2$ means a monocyclic or bicyclic aryl group or a monocyclic or bicyclic 5- to 10-membered heteroaryl group with 1-2 heteroatoms selected from the group that consists of N, S or O, whereby the mentioned aryl group or heteroaryl group can be substituted with up to three of the following substituents, independently of one another:

F, Cl, Br, XOH, XOR$^4$, XOCOR$^4$, XOCONHR$^4$, XOCOOR$^4$, XCOR$^4$, XC(NOH)R$^4$, XC(NOR$^4$)R$^{4'}$, XC(NO(COR$^4$))R$^{4'}$, XCN, XCOOH, XCOOR$^4$, XCONH$_2$, XCONR$^4$R$^{4'}$, XCONHR$^4$, XCONHOH, XCONHOR$^4$, XCOSR$^4$, XSR$^4$, XSOR$^4$, XSO$_2$R$^4$, SO$_2$NH$_2$, SO$_2$NHR$^4$, SO$_2$NR$^4$R$^{4'}$, NO$_2$, XNH$_2$, XNHR$^4$, XNR$^4$R$^{4'}$, XNHSO$_2$R$^4$, XN(SO$_2$R$^4$)(SO$_2$R$^{4'}$), XNR$^4$SO$_2$R$^{4'}$, XNHCOR$^4$, XNHCOOR$^4$, XNHCONHR$^4$, R$^4$, whereby two substituents at R$^2$, if they are in ortho-position to one another, can be linked to one another in such a way that they jointly form methanediylbisoxy, ethane-1,2-diylbisoxy, propane-1,3-diyl, butane-1,4-diyl.

Also preferred is the use of compounds of general formula II, whereby

R$^3$ stands for one or two substituents, which independently of one another, mean:

hydrogen, F, Cl, Br, XOH, XOR$^4$, XOCOR$^4$, XOCONHR$^4$, XOCOOR$^4$, XCOR$^4$, XC(NOH)R$^4$, XC(NOR$^4$)R$^{4'}$, XC(NO(COR$^4$))R$^{4'}$, XCN, XSR$^4$, XSOR$^4$, XSO$_2$R$^4$, SO$_2$NH$_2$, SO$_2$NHR$^4$, SO$_2$NR$^4$R$^{4'}$, NO$_2$, XNH$_2$, XNHR$^4$, XNR$^4$R$^{4'}$, XNHSO$_2$R$^4$, XNR$^4$SO$_2$R$^{4'}$, XN(SO$_2$R$^4$)(SO$_2$R$^{4'}$), XNHCOR$^4$, XNHCOOR$^4$, XNHCONHR$^4$, or R$^4$, whereby two substituents R$^3$, if they are in ortho-position to one another, can be linked to one another in such a way that they jointly form methanediylbisoxy, ethane-1,2-diylbisoxy, propane-1,3-diyl, butane-1,4-diyl.

Also preferred is the use of compounds of general formula II whereby

R$^4$ and R$^{4'}$, independently of one another, mean CF$_3$, C$_2$F$_5$, C$_{1-4}$ alkyl, C$_{2-4}$ alkenyl, C$_{2-4}$ alkinyl, C$_{3-6}$ cycloalkyl, (C$_{1-3}$ alkyl-C$_{3-6}$ cycloalkyl), C$_{1-3}$ alkylaryl, C$_{1-3}$ alkylheteroaryl, monocyclic aryl or 5- to 6-membered heteroaryl with 1-2 N, S or O atoms, whereby the aryl and heteroaryl groups can be substituted with one or two substituents from the group that consists of F, Cl, Br, CH$_3$, C$_2$H$_5$, OCH$_3$, OC$_2$H$_5$, CF$_3$, C$_2$F$_5$ or else can carry an annelated methanediylbisoxy or ethane-1,2-diylbisoxy group, and in addition in a 5-membered cycloalkyl ring, a ring member can be an N or an O, and in a 6-membered cycloalkyl ring, one or two ring members can be N and/or O, whereby ring nitrogens optionally can be substituted with C$_{1-3}$ alkyl or C$_{1-3}$ alkanoyl.

Also preferred is the use of compounds of general formula II, in which

R$^5$ and R$^{5'}$, independently of one another, can be C$_{1-6}$ alkyl, whereby a carbon atom can be exchanged for O, NH, NC$_{1-3}$ alkyl, NC$_{1-3}$ alkanoyl, C$_{3-7}$ cycloalkyl-C$_{0-3}$ alkyl, whereby in a 5-membered cycloalkyl ring, a ring member can be an N or an O, and in a 6- or 7-membered cycloalkyl ring, one or two ring members can be N and/or O, whereby ring nitrogens optionally can be substituted with C$_{1-3}$ alkyl or C$_{1-3}$ alkanoyl, whereby the mentioned C$_{1-6}$ alkyl part can be substituted with one of the previously mentioned cycloalkyls or else a 5- to 6-membered heteroaromatic compound with 1-2 heteroatoms, selected from the group that consists of N, S or O, whereby all previously mentioned alkyl and cycloalkyl parts can be substituted with up to two substituents that consist of CF$_3$, OH, OC$_{1-3}$ alkyl, and the previously mentioned heteroaryl groups can be substituted with one or two substituents that consist of F, Cl, CF$_3$, CH$_3$, C$_2$H$_5$, OCH$_3$, OC$_2$H$_5$, or R$^5$ and R$^{5'}$ together with the nitrogen atom form a 5- to 7-membered heterocyclic compound, which can contain another oxygen, nitrogen or sulfur atom and can be substituted with C$_{1-4}$ alkyl, C$_{1-4}$ alkoxy-C$_{0-2}$ alkyl, C$_{1-4}$ alkoxy-carbonyl, aminocarbonyl or phenyl.

Also preferred is the use of compounds of general formula II, whereby

A means C$_{1-10}$ alkanediyl, C$_{2-10}$ alkenediyl, C$_{2-10}$ alkinediyl, (C$_{0-5}$ alkanediyl-C$_{3-7}$ cycloalkanediyl-C$_{0-5}$ alkanediyl), or (C$_{0-5}$ alkanediyl-heteroarylene-C$_{0-5}$ alkanediyl), whereby an optionally present heteroaryl group can be substituted with one or two substituents that consist of F, Cl, Br, CH$_3$, C$_2$H$_5$, NO$_2$, OCH$_3$, OC$_2$H$_5$, CF$_3$, C$_2$F$_5$, and in addition in a 5-membered cycloalkyl ring, a ring member can be an N or an O, and in a 6- or 7-membered cycloalkyl ring, one or two ring members can be N and/or O, whereby ring nitrogens optionally can be substituted with C$_{1-3}$ alkyl or C$_{1-3}$ alkanoyl, whereby in an aliphatic chain, a carbon atom or two carbon atoms can be exchanged for O, NH, NC$_{1-3}$ alkyl, NC$_{1-3}$ alkanoyl, NSO$_2$C$_{1-3}$ alkyl, and whereby alkyl or cycloalkyl parts can be substituted with up to two F atoms or one of the substituents that consists of OH, OC$_{1-3}$ alkyl, OC$_{1-3}$ alkanoyl, =O, NH$_2$, NHC$_{1-3}$ alkyl, N(C$_{1-3}$ alkyl), NHC$_{1-3}$ alkanoyl, N(C$_{1-3}$ alkyl)(C$_{1-3}$ alkanoyl), NHCOOC$_{1-3}$ alkyl, NHCONHC$_{1-3}$ alkyl, NHSO$_2$C$_{1-3}$ alkyl, SH, SC$_{1-3}$ alkyl.

Also preferred is the use of the compounds of general formula II, whereby

B means hydrogen, OH, OCOR$^5$, OCONHR$^5$, OCOOR$^5$, COOH, COOR$^5$, CONH$_2$, CONHR$^5$, CONR$^5$R$^{5'}$, CONHOH, CONHOR$^5$, or tetrazolyl, in each case bonded to a carbon atom of group A.

Also preferred is the use of compounds of general formula II, whereby

X means a bond or CH$_2$.

Also preferred is the use of compounds of general formula II, whereby

Y means a bond, O, S, NH, NR$^4$, NCOR$^4$ or NSO$_2$R$^4$.

Example 307 describes how the inhibition of the microglia activation can be measured. In this case, the activation of the microglia can be carried out by various stimuli, such as, e.g., Aβ-peptide (β-amyloid, Araujo, D. M. and Cotman, C. M. Brain Res. 569, 141-145 (1992)), prion protein, cytokines or by cell fragments (Combs, C. K. et al. (1999) J. Neurosci., 19, 928-939, Wood, P. L. (1998) Neuroinflammation: Mechanisms and Management, Humana Press). For example, the compound of Example 49, 6-[[1-(4-methylphenyl)-2-phenyl-1H-benzimidazol-6-yl]oxy]hexanoic acid isopropyl ester indicates an inhibition of IC$_{50}$=0.75 μm.

The stimulation with the Aβ-peptide corresponds to the pathophysiological situation in Alzheimer's disease. In this test, the substances according to the invention showed inhibition of microglia activation in the case of stimulation with the Aβ-peptide. The inhibition of the microglia activation by the substances according to the invention results in a strong reduction of the cytokine production and secretion, e.g., of Il1β and TNFα (measured by ELISA and mRNA expression analysis) and in a reduced secretion of reactive oxygen/nitrogen intermediate products. Several inflammation factors are thus equally inhibited.

The in vivo action of the substances according to the invention was shown in an MCAO model in rats. This model simulates the state of a stroke. The substances according to the invention reduce the microglia activation, which occurs in the case of active brain lesions in the brains of animals.

The invention also relates to the use of the compounds of general formula I and of general formula II according to the invention for the production of a pharmaceutical agent for treating or preventing diseases that are associated with a microglia activation. Examples of such diseases are AIDS dementia, amyotrophic lateral sclerosis, Creutzfeldt-Jacob disease, Down's syndrome, diffuse Lewy body's disease, Huntington's disease, leukoencephalopathy, multiple sclerosis, Parkinson's disease, Pick's disease, Alzheimer's disease, stroke, temporary lobe epilepsy and tumors.

The invention also relates to pharmaceutical agents that contain one or more compounds of general formula I according to the invention and one or more vehicles. The pharmaceutical agents or compositions of the invention are produced in a way that is known per se with the commonly used solid or liquid vehicles or diluents and the commonly used pharmaceutical and technical adjuvants corresponding to the desired type of administration with a suitable dosage. The preferred preparations consist of a form for dispensing that is suitable for oral, enteral or parenteral administration. Such forms for dispensing are, for example, tablets, film tablets, coated tablets, pills, capsules, powders or depot forms as well as suppositories. Corresponding tablets can be obtained, for example, by mixing active ingredient with known adjuvants, for example inert diluents such as dextrose, sugar, sorbitol, mannitol, polyvinylpyrrolidone, explosives such as corn starch or alginic acid, binders such as starch or gelatin, lubricants such as carboxypolymethylene, carboxy methyl cellulose, cellulose acetate phthalate or polyvinyl acetate. The tablets can also consist of several layers.

Coated tablets can be produced accordingly by coating cores that are produced analogously to the tablets with agents that are commonly used in coated tablet coatings, for example polyvinylpyrrolidone or shellac, gum arabic, talc, titanium oxide or sugar. In this case, the shell of the coated tablet can also consist of several layers, whereby the adjuvants that are mentioned above in the case of the tablets can be used. Capsules that contain active ingredients can also be produced, for example, by the active ingredient being mixed with an inert vehicle such as lactose or sorbitol and encapsulated in gelatin capsules.

The substances according to the invention can also be used in suitable solutions such as, for example, physiological common salt solution, as infusion or injection solutions.

For parenteral administration, in particular oily solutions, such as, for example, solutions in sesame oil, castor oil and cottonseed oil, are suitable. To increase solubility, solubilizers can be added, such as, for example, benzyl benzoate or benzyl alcohol.

It is also possible to incorporate the substances according to the invention in a transdermal system and to administer them transdermally.

The dosage of the substances of general formula I and of general formula II according to the invention is determined by the attending physician and depends on, i.a., the substance that is administered, the method of administration, the disease that is to be treated and the severity of the disease. The daily dose is no more than 1000 mg, preferably no more than 100 mg, whereby the dose can be given as a single dose to be administered once or divided into 2 or more daily doses.

The compounds of formula I can be present as tautomers, stereoisomers or geometric isomers. The invention also comprises all possible isomers, such as E- and Z-isomers, S- and R-enantiomers, diastereomers, racemates and mixtures thereof including the tautomeric compounds.

The isomer mixtures can be separated into enantiomers or E/Z isomers according to commonly used methods, such as, for example, crystallization, chromatography or salt formation.

The production of the compounds according to the invention is carried out analogously to known processes that are described in, for example, EP 531 883. If the production of the starting compounds is not described, the starting compounds are known and are commercially available or their production is carried out analogously to the processes described here. Below, the production of some precursors, intermediate products and products is described by way of example.

In the production of the substances according to the invention, for example, the following processes are used:

General Operating Instructions 1:

Reduction Nitro Groups, Hydrogenation of Olefinic Double Bonds and Hydrogenolytic Cleavage of Benzyl Ethers The compound that is to be reduced is dissolved in ethyl acetate, tetrahydrofuran, methanol or ethanol or mixtures of the solvent, and it is hydrogenated to 2-5% (relative to the nitro compound) palladium on carbon (10%) at normal pressure. After hydrogen absorption has ended, it is suctioned off, the residue is washed with ethyl acetate or methanol or ethanol, and the filtrate is concentrated by evaporation in a vacuum. The crude product is reacted generally without further purification.

General Operating Instructions 2:

Reduction Nitro Groups 9.2 g of iron(II) sulfate is introduced into 30 ml of water and 9 ml of ammonia solution. A solution of 3.6 mmol of the nitro compound in 100 ml of ethanol is added in drops to it, and the suspension is stirred intensively for 1 hour at 70° C. Then, it is allowed to settle, solid is filtered out, the filtrate is concentrated by evaporation to a large extent, mixed with water and extracted three times with ethyl acetate. The combined extracts are dried on sodium sulfate and concentrated by evaporation in a vacuum. The amino compound is further processed as a crude product.

General Operating Instructions 3:

Cyclization to Benzimidazoles with Orthoesters 10 mmol of a 1,2-diaminobenzene derivative is dissolved in 25 ml of ethanol. 47 ml of an 0.8 M ethereal HCl solution is added in drops to it, it is stirred for 30 minutes and then evaporated to the dry state in a vacuum. The residue is taken up in 230 ml of methanol and mixed with 6 ml of trimethyl orthobenzoate or the corresponding amount of another orthoester. It is refluxed for 2-8 hours, poured onto saturated sodium bicarbonate solution after cooling, extracted three times with ethyl acetate, the combined extracts are dried on sodium sulfate and concentrated by evaporation in a vacuum. The residue is purified by crystallization or column chromatography on silica gel.

General Operating Instructions 4:

Cyclization to Benzimidazoles with Imino Ester Hydrochlorides 1.2 mmol of a 1,2-diaminobenzene derivative is dissolved in 5 ml of tetrahydrofuran, mixed with 1.5 mmol of a benzimidate hydrochloride, and the mixture is stirred for 15 hours. The batch is mixed with saturated sodium bicarbonate solution, diluted with water and extracted three times with ethyl acetate. The combined organic phases are washed three times with 1N aqueous hydrochloric acid and once with saturated sodium chloride solution, dried on sodium sulfate, filtered on one frit with silica gel, and the solution is evaporated to the dry state. The product crystallizes from diisopropyl ether.

General Operating Instructions 5:

Cyclization to Benzimidazoles Via Carboxylic Acid Anilides 4.7 mmol of a 1,2-diaminobenzene derivative is dissolved in 20 ml of dichloromethane, mixed with 14 mmol of triethylamine and mixed slowly with 6 mmol of carboxylic acid chloride, and the mixture is stirred for 15 hours. The batch is mixed with saturated sodium bicarbonate solution, diluted with water and extracted twice with dichloromethane. The combined organic phases are washed with water and with saturated sodium chloride solution, dried on sodium sulfate and concentrated by evaporation in a vacuum. The remaining crude carboxylic acid anilide is taken up in a 9:1 mixture that consists of methanol and concentrated hydrochloric acid and refluxed for 1 hour. The reaction mixture is slowly introduced into saturated sodium bicarbonate solution after cooling, diluted with water and extracted three times with dichloromethane. The combined organic phases are washed with saturated sodium chloride solution, dried on sodium sulfate and concentrated by evaporation in a vacuum. The residue is purified, if necessary, by crystallization or column chromatography on silica gel.

General Operating Instructions 6:

Ether Cleavage with Hydrobromic Acid 5 g of arylmethylether is mixed with 160 ml of 48% aqueous HBr and refluxed for 1-5 hours. After cooling, it is filtered. The residue is taken up in ethyl acetate, and it is extracted three times with saturated sodium bicarbonate solution. After drying on sodium sulfate, it is concentrated by evaporation in a vacuum. The residue is purified, if necessary, by crystallization or column chromatography on-silica gel.

General Operating Instructions 7:

Ether Cleavage with Boron Tribromide 1.86 mmol of aryl methyl ether is dissolved in 18 ml of dichloromethane and mixed slowly at −35° C. with 7.4 ml of a 1 M solution of boron tribromide in dichloromethane. It is left for 12-15 hours at −30° C., then mixed with saturated sodium bicarbonate solution, extracted three times with dichloromethane, the combined extracts are dried on sodium sulfate and concentrated by evaporation in a vacuum. The residue is purified, if necessary, by column chromatography on silica gel.

General Operating Instructions 8:

Akylation of Hydroxybenzimidazole Derivatives and Phenol Derivatives with Alkyl Halides A solution of 1.85 mmol of the hydroxybenzimidazole derivative in 12 ml of N,N-dimethylformamide is mixed with 1.85 mmol of cesium carbonate, and 2.24 mmol of alkyl bromide or alkyl iodide. When alkyl bromides are used, optionally 1.85 mmol of sodium iodide is added. It is stirred for 12-96 hours, then poured onto water, taken up with ethyl acetate, the organic phase is washed four times with water, dried on sodium sulfate and concentrated by evaporation in a vacuum.

As an alternative to this aqueous working up, the reaction mixture can be mixed with dichloromethane, separated from the precipitating salts by filtration and the filtrate concentrated by evaporation in a vacuum.

Independently of the working-up method, the residue is purified by crystallization or column chromatography on silica gel.

General Operating Instructions 9:

Saponification of Carboxylic Acid Alkyl Esters 0.77 mmol of the carboxylic acid alkyl ester is dissolved in 5 ml of methanol and 5 ml of tetrahydrofuran, and it is mixed with 5 ml of a 0.5N aqueous lithium or sodium hydroxide solution. After 2-12 hours of stirring, it is concentrated by evaporation in a vacuum to a very large extent, neutralized by the addition of aqueous hydrochloric acid and extracted with ethyl acetate. It is dried on sodium sulfate and concentrated by evaporation in a vacuum. The residue is purified, if necessary, by column chromatography on silica gel.

General Operating Instructions 10:

Esterification of Carboxylic Acids 0.2 mmol of carboxylic acid is dissolved in 1 ml of primary or secondary alcohol, mixed with two drops of concentrated sulfuric acid and stirred for 12 hours at 60° C. The batch is then mixed with saturated potassium bicarbonate solution, diluted with water and extracted three times with ethyl acetate. After the combined extracts are washed with saturated sodium chloride solution and dried on sodium sulfate, it is concentrated by evaporation in a vacuum, and the residue is crystallized from diisopropyl ether.

General Operating Instructions 11:

Reduction of Carboxylic Acid Alkyl Esters with Lithium Aluminum Hydride 0.15 mmol of carboxylic acid ester is dissolved in tetrahydrofuran and mixed with 0.09 mmol of lithium aluminum hydride. It is allowed to stir for 1-48 hours, mixed with water and extracted three times with dichloromethane. After the combined organic phases are dried on sodium sulfate, it is concentrated by evaporation in a vacuum. The residue is purified, if necessary, by crystallization or by column chromatography on silica gel.

General Operating Instructions 12:

Wittig Reaction of Benzimidazole Carbaldehydes with (ω-Carboxyalkyl)Triphenylphosphonium Bromides and Esterification with Methanol 2 mmol of the (ω-carboxyalkyl)triphenylphosphonium bromide is mixed in 2.5 ml of dimethyl sulfoxide and 2.5 ml of tetrahydrofuran at 0° C. with 4 mmol of potassium-tert-butylate, and it is stirred for 30 minutes at T>10° C. Then, a solution of 0.67 mmol of the aldehyde in 2 ml of tetrahydrofuran is added, and it is stirred for 3 hours at 20° C. The batch is then mixed with saturated ammonium chloride solution, diluted with water and extracted three times with ethyl acetate. After the combined organic phases are dried on sodium sulfate, it is concentrated by evaporation in a vacuum. The residue is dissolved in 15 ml of methanol, mixed with two drops of concentrated sulfuric acid and allowed to stand for 48-72 hours. After concentration by evaporation in a vacuum, the residue is purified by column chromatography on silica gel.

General Operating Instructions 13:

Reaction of Aminobenzimidazoles with Alkyl- and Arylsulfonic Acid Halides

47 μmol of aminobenzimidazole derivative is dissolved in 0.5 ml of dichloromethane, mixed with 51 μmol of triethylamine and 51 μmol of alkyl- or arylsulfonic acid halide, and the reaction mixture is stirred for 2-15 hours. For working-up, saturated sodium bicarbonate solution is added, extracted three times with dichloromethane, the combined organic phases are washed with water, dried on sodium sulfate and concentrated by evaporation in a vacuum. The residue is purified by crystallization or by column chromatography on silica gel.

General Operating Instructions 14:

Copper-Mediated O- or N-Arylation of Benzimidazoles 5 mmol of an N-unsubstituted benzimidazole derivative or an N-aryl-substituted hydroxybenzimidazole derivative is dissolved in 20 ml of dichloromethane. 10 mmol of an arylboronic acid, 5 mmol of anhydrous copper(II) acetate, 10 mmol of pyridine or triethylamine and about 2.5 g of molecular sieve (4) are added, stirred for 48-72 hours in a moisture-free environment, then silica gel is added, it is evaporated to the dry state in a vacuum, and the remaining powder is purified by chromatography on silica gel. Regioisomeric N-arylation products are separated, if necessary, using HPLC.

General Operating Instructions 15:

Base-Catalyzed N-Substitution of Benzimidazoles 5 mmol of an N-unsubstituted benzimidazole derivative is dissolved in 20 ml of dimethylacetamide. 25 mmol of sodium hydride and 20 mmol of an electron-free aryl or heteroaryl halide are added and refluxed for 48-72 hours in a moisture-free environment, then silica gel is added, it is evaporated to the dry state in a vacuum, and the remaining powder is purified by chromatography on silica gel. Regioisomeric N-arylation products are separated, if necessary, using HPLC.

General Operating Instructions 16:

Cyclization to Benzimidazoles with Aldehydes 1 mmol of a 1,2-diaminobenzene derivative is dissolved in 3 ml of nitrobenzene. 1 mmol of an aryl- or heteroaryl aldehyde is added to this. It is heated for 2-6 hours to 150° C. and allowed to cool. The residue is directly purified by column chromatography on silica gel without further working-up.

General Operating Instructions 17:

Conversion of Carboxylic Acids into Carboxylic Acid Amides 0.25 mmol of a carboxylic acid is dissolved in 3 ml of N,N-dimethylformamide, mixed with 0.38 mmol of a primary or secondary amine, 0.5 mmol of triethylamine and 0.25 mmol of diphenylphosphorylazide, and the mixture is stirred for 2 days. For working-up, water is added, it is extracted three times with ethyl acetate, the combined organic phases are washed with water, dried on sodium sulfate and concentrated by evaporation in a vacuum. The residue is purified by column chromatography on silica gel.

General Operating Instructions 18:

Conversion of Carboxylic Acid Esters into Carboxylic Acid Amides 0.36 mmol of an amine is dissolved in 3 ml of toluene and mixed drop by drop with 0.18 ml of a 2 M solution of trimethylaluminum in toluene while being cooled in an ice bath. It is mixed with a solution that consists of 0.33 mmol of the carboxylic acid methyl ester in 3 ml of toluene and stirred for 2-8 hours at 95° C. For working-up, water is added after cooling, extracted three times with ethyl acetate, the combined organic phases are washed with saturated sodium chloride solution, dried on sodium sulfate and concentrated by evaporation in a vacuum. The residue is purified by column chromatography on silica gel.

EXAMPLE 1

[(1,2-Diphenyl-1H-benzimidazol-6-yl)oxy]acetic acid isopropyl ester was obtained by reaction of 1,2-diphenyl-6-hydroxy-1H-benzimidazole (Benincori, T.; Sannicolo, F.; J. Heterocycl. Chem.; 25; 1988; 1029-1033) with bromoacetic acid isopropyl ester according to general operating instructions 8.

Flash point 137-138° C.

EXAMPLE 2

[(1,2-Diphenyl-1H-benzimidazol-6-yl)oxy]ethan-1-ol was obtained by reaction of [(1,2-diphenyl-1H-benzimidazol-6-yl)oxy]acetic acid methyl ester (DE 4330959) according to general operating instructions 11.

$^1$H-NMR (D$_6$-DMSO): δ=3.72 ppm t (J=7.5 Hz, 2H); 4.02 t (J=7.5 Hz, 2H); 6.72 d (J=2 Hz, 1H); 7.10 dd (J=8, 2 Hz, 1H); 7.38-7.68 m (10H); 7.76 d (J=8 Hz, 1H).

EXAMPLE 3

3-[(1,2-Diphenyl-1H-benzimidazol-6-yl)oxy]propan-1-ol 0.5 g of 1,2-diphenyl-6-hydroxy-1H-benzimidazole was reacted according to general operating instructions 8 with 3-(bromopropoxy)-tert-butyldimethylsilane. After chromatography on silica gel, it was taken up in 2.5 ml of methanol, 0.4 ml of concentrated-hydrochloric acid was added, and it was allowed to stir for 2 hours at 20° C. It was poured onto saturated aqueous sodium bicarbonate solution, extracted three times with ethyl acetate, the combined extracts were washed with saturated aqueous sodium chloride solution, dried on sodium sulfate and concentrated by evaporation in a vacuum.

Flash point 191-193° C.

EXAMPLE 4

3-[(1,2-Diphenyl-1H-benzimidazol-6-yl)oxy]propanoic acid 100 mg of 3-[(1,2-diphenyl-1H-benzimidazol-6-yl)oxy]propan-1-ol was introduced into 2.5 ml of acetone and mixed at −15° C. with 0.15 ml of a solution of Jones reagent (produced from 0.27 g of chromium(VI) oxide, 1 ml of water and 0.23 ml of concentrated sulfuric acid). After 3.5 hours of stirring at −15° C., it was quenched with the addition of isopropanol. It was diluted with water, extracted three times with dichloromethane, the combined organic phases were dried on sodium sulfate and concentrated by evaporation in a vacuum. The residue was purified by chromatography on silica gel.

$^1$H-NMR (D$_6$-DMSO): δ=2.60 ppm t (J=7.5 Hz, 2H), 4.15 t (J=7.5 Hz, 2H); 6.64 d (J=2 Hz, 1H); 6.95 dd (J=8, 2 Hz, 1H); 7.30-7.61 m (10H); 7.69 d (J=8 Hz, 1H).

EXAMPLE 5

3-[(1,2-Diphenyl-1H-benzimidazol-6-yl)oxy]propanoic acid methyl ester 45 mg of 3-[(1,2-diphenyl-1H-benzimidazol-6-yl)oxy]propanoic acid was dissolved in 0.5 ml of N,N-dimethylformamide and mixed with 41 mg of cesium carbonate and 10 μl of methyl iodide. It was allowed to stir for 2 days, diluted with dichloromethane, filtered, the filtrate was concentrated by evaporation in a vacuum, and the residue was chromatographed on silica gel.

Flash point 120-121° C.

EXAMPLE 6

2-[(1,2-Diphenyl-1H-benzimidazol-6-yl)oxy]propanoic acid methyl ester was obtained by reaction of 1,2-diphenyl-6-hydroxy-1H-benzimidazole with 2-bromopropanoic acid methyl ester according to general operating instructions 8.

Flash point 132-135° C.

EXAMPLE 7

4-[(1,2-Diphenyl-1H-benzimidazol-6-yl)oxy]butanoic acid isopropyl ester was obtained by reaction of 1,2-diphenyl-6-hydroxy-1H-benzimidazole with 4-bromobutanoic acid isopropyl ester according to general operating instructions 8.

Flash point 89-91° C.

EXAMPLE 8

4-[(1,2-Diphenyl-1H-benzimidazol-6-yl)oxy]butan-1-ol was obtained by reaction of 4-[(1,2-diphenyl-1H-benzimidazol-6-yl)oxy]butanoic acid methyl ester according to general operating instructions 11.

Flash point 159-160° C.

EXAMPLE 9

Acetic acid-[4-[(1,2-diphenyl-1H-benzimidazol-6-yl)oxy]but-1-yl]ester 50 mg of 4-[(1,2-diphenyl-1H-benzimidazol-6-yl)oxy]butan-1-ol was dissolved in 1 ml of dichloromethane, mixed with 0.34 ml of pyridine and 20 μl of acetyl chloride and stirred for 15 hours. It was mixed with saturated sodium bicarbonate solution, diluted with water, extracted twice with dichloromethane, the combined organic phases were washed with saturated sodium chloride solution, dried on sodium sulfate and concentrated by evaporation in a vacuum. The residue was purified using thick-layer chromatography.

Flash point 68-69° C.

EXAMPLE 10

Pivalic acid-[4-[(1,2-diphenyl-1H-benzimidazol-6-yl)oxy]but-1-yl]-ester was produced analogously to the instructions, indicated in Example 9, from 50 mg of 4-[(1,2-diphenyl-1H-benzimidazol-6-yl)oxy]butan-1-ol, 0.34 ml of pyridine and 22 μl of trimethylacetic acid chloride.

Flash point 104-106° C.

EXAMPLE 11

4-[(1,2-Diphenyl-1H-benzimidazol-6-yl)oxy]butyl-N-methylcarbamate 100 mg of 4-[(1,2-diphenyl-1H-benzimidazol-6-yl)oxy]butan-1-ol was dissolved in 4 ml of dichloromethane, mixed with 0.1 ml of triethylamine and 20 mg of methyl isocyanate and stirred for 15 hours. Another 0.1 ml of triethylamine and 20 mg of methyl isocyanate were added, allowed to stir for 20 hours, and then concentrated by evaporation in a vacuum. The residue was purified using chromatography on silica gel.

Flash point 124-126° C.

EXAMPLE 12

5-[(1,2-Diphenyl-1H-benzimidazol-6-yl)oxy]pentanoic acid isopropyl ester 994 was obtained by reaction of 1,2-diphenyl-6-hydroxy-1H-benzimidazole with 5-bromopentanoic acid isopropyl ester according to general operating instructions 8.

Flash point 91-92° C.

EXAMPLE 13

6-[(1,2-Diphenyl-1H-benzimidazol-6-yl)oxy]hexanoic acid methyl ester was obtained by reaction of 1,2-diphenyl-6-hydroxy-1H-benzimidazole with 6-bromohexanoic acid methyl ester according to general operating instructions 8.

$^1$H-NMR (CDCl$_3$): δ=1.44-1.56 m (2H); 1.64-1.85 m (4H); 2.33 t (J=7.5 Hz, 2H); 3.66 s (3H); 3.93 t (J=7.5 Hz, 2H); 6.70 d (J=2 Hz, 1H); 6.96 dd (J=8, 2 Hz, 1H); 7.22-7.38 m (5H); 7.43-7.58 m (5H); 7.76 d (J=8 Hz, 1H).

EXAMPLE 14

6-[(1,2-Diphenyl-1H-benzimidazol-6-yl)oxy]hexanoic acid isopropyl ester was obtained by reaction of 1,2-diphenyl-6-hydroxy-1H-benzimidazole with 6-bromohexanoic acid isopropyl ester according to general operating instructions 8.

$^1$H-NMR (CDCl$_3$): δ=1.22 ppm d (J=7.5 Hz, 6H); 1.43-1.56 m (2H); 1.62-1.87 m (4H); 2.30 t (J=7.5 Hz, 2H); 3.93 t (J=7.5 Hz, 2H), 5.01 sp (J=7.5 Hz, 1H); 6.69 d (J=2 Hz,

EXAMPLE 15

6-[(1,2-Diphenyl-1H-benzimidazol-6-yl)oxy]hexanoic acid was obtained by reaction of 6-[(1,2-diphenyl-1H-benzimidazol-6-yl)oxy]hexanoic acid methyl ester according to general operating instructions 9.

$^1$H-NMR (D$_6$-DMSO): δ=1.35-1.49 ppm m (2H); 1.50-1.63 m (2H); 1.65-1.77 m (2H); 2.23 t (J=7.5 Hz, 2H); 3.92 t (J=7.5 Hz, 2H); 6.62 d (J=2 Hz, 1H); 6.95 dd (J=10, 2 Hz, 1H); 7.30-7.62 m (10H); 7.68 d (J=10 Hz, 1H).

EXAMPLE 16

6-[(1,2-Diphenyl-1H-benzimidazol-6-yl)oxy]hexan-1-ol was obtained by reaction of 6-[(1,2-diphenyl-1H-benzimidazol-6-yl)oxy]hexanoic acid methyl-ester according to general operating instructions 11.

$^1$H-NMR (CDCl$_3$): δ=1.35-1.85 ppm m (8H); 3.67 t (J=7.5 Hz, 2H); 3.98 t (J=7.5 Hz, 2H); 6.70 d (J=2 Hz, 1H); 6.98 dd (J=8.2 Hz, 1H); 7.24-7.38 m (5H); 7.45-7.58 m (5H); 7.75 d (J=8 Hz, 1H).

EXAMPLE 17

6-[(1,2-Diphenyl-1H-benzimidazol-6-yl)oxy]hexanamide a) 6-[(1,2-Diphenyl-1H-benzimidazol-6-yl)oxy]hexanonitrile was obtained by reaction of 1,2-diphenyl-6-hydroxy-1H-benzimidazole with 6-bromohexanonitrile according to general operating instructions 8.

Flash point 108-112° C.

6-[(1,2-Diphenyl-1H-benzimidazol-6-yl)oxy]hexanamide 18 mg of potassium carbonate and 40 µl of 30% hydrogen peroxide solution were added to a solution of 50 mg of 6-[(1,2-diphenyl-1H-benzimidazol-6-yl)oxy]hexanonitrile in 1 ml of methanol, and it was allowed to stir for 24 hours. Then, ice-cold aqueous sodium thiosulfate solution was stirred in and extracted three times with ethyl acetate. After drying on sodium sulfate, it was concentrated by evaporation in a vacuum, and the residue was chromatographed on silica gel.

$^1$H-NMR (CDCl$_3$): δ=1.48-1.60 ppm m (2H); 1.65-1.87 m (4H); 2.25 t (J=7.5 Hz, 2H); 3.94 t (J=7.5 Hz, 2H); 5.30-5.53 broad (2H), 6.68 d (J=2 Hz, 1H); 6.95 dd (J=8, 2 Hz, 1H); 7.23-7.38 m (5H); 7.42-7.58 m (5H), 7.75 d (J=8 Hz, 1H).

EXAMPLE 18

N-Methoxy-6-[(1,2-diphenyl-1H-benzimidazol-6-yl)oxy]hexanoic acid amide 100 mg of 6-[(1,2-diphenyl-1H-benzimidazol-6-yl)oxy]hexanoic acid was dissolved in 2 ml of tetrahydrofuran, mixed with 39 mg of carbonyldiimidazole, stirred for 30 minutes at 20° C. and then refluxed for 30 minutes. At 20° C., 21 mg of O-methylhydroxyaminohydrochloride was then added, and it was allowed to stir for 18 hours. The reaction mixture was diluted with ethyl acetate and washed with 2N aqueous hydrochloric acid and saturated potassium bicarbonate solution. After drying on sodium sulfate, it was concentrated by evaporation in a vacuum, and the residue was chromatographed on silica gel.

Flash point 144-145° C.

EXAMPLE 19

N-(Phenylmethoxy)-6-[(1,2-diphenyl-1H-benzimidazol-6-yl)oxy]hexanamide was obtained by reaction of 6-[(1,2-diphenyl-1H-benzimidazol-6-yl)oxy]hexanoic acid with O-benzylhydroxylaminohydrochloride according to the general operating instructions that are indicated in Example 18.

Flash point 144° C.

EXAMPLE 20

N-Hydroxy-6-[(1,2-diphenyl-1H-benzimidazol-6-yl)oxy]hexanamide 23 mg of N-(phenylmethoxy)-6-[(1,2-diphenyl-1H-benzimidazol-6-yl)oxy]hexanamide was dissolved in 4 ml of ethanol, mixed with 15 mg of palladium on carbon (10%) and stirred under a hydrogen atmosphere for 3 hours. After catalyst was separated out, it was concentrated by evaporation in a vacuum, and the residue was crystallized from diethyl ether.

Flash point 83-85° C.

EXAMPLE 21

7-[(1,2-Diphenyl-1H-benzimidazol-6-yl)oxy]heptanoic acid methyl ester was obtained by reaction of 1,2-diphenyl-6-hydroxy-1H-benzithidazole with 7-bromoheptanoic acid methyl ester according to general operating instructions 8.

Flash point 77-80° C.

EXAMPLE 22

7-[(1,2-Diphenyl-1H-benzimidazol-6-yl)oxy]heptanoic acid was obtained by reaction of 7-[(1,2-diphenyl-1H-benzimidazol-6-yl)oxy]heptanoic acid methyl ester according to general operating instructions 9.

Flash point 142-145° C.

EXAMPLE 23

7-[(1,2-Diphenyl-3H-benzimidazol-6-yl)oxy]heptanoic acid isopropyl ester was obtained by reaction of 7-[(1,2-diphenyl-1H-benzimidazol-6-yl)oxy]heptanoic acid with isopropanol according to general operating instructions 10.

Flash point 98-100° C.

EXAMPLE 24

6-[[1-(3-Nitrophenyl)-2-phenyl-1H-benzimidazol-6-yl]oxy]hexanoic acid isopropyl ester was obtained by reaction of 6-hydroxy-1-(3-nitrophenyl)-2-phenyl-1H-benzimidazole (DE 4330959) with 6-bromohexanoic acid isopropyl ester according to general operating instructions 8.

Flash point 111-113° C.

EXAMPLE 25

6-[[2-Phenyl-1-[3-(trifluoromethyl)phenyl]-1H-benzimidazol-6-yl]oxy]hexanoic acid methyl ester a) (5-Methoxy-2-nitrophenyl)[(3-trifluoromethyl)phenyl]amine 2 g of 3-fluoro-4-nitroanisole and 16 ml of 3-(trifluoromethyl)aniline were stirred for 72 hours at 140° C. The batch was then diluted with ethyl acetate, washed ten times with 4N aqueous hydrochloric acid and once with saturated sodium chloride solution, dried on sodium sulfate, concentrated by evaporation in a vacuum, and the residue was chromatographed on silica gel.

$^1$H-NMR (CDCl$_3$): δ=3.78 ppm s (3H); 6.42 dd (J=8.2 Hz, 1H); 6.60 d (J=2 Hz, 1H); 7.45-7.60 m (4H); 8.22 d (J=8 Hz, 1H); 9.78 s (broad)(1H).

b) 6-Methoxy-2-phenyl-1-[(3-trifluoromethyl)phenyl]-1H-benzimidazole was obtained by hydrogenation of (5-methoxy-2-nitrophenyl)[(3-trifluoromethyl)phenyl]amine according to general operating instructions 1 and subsequent cyclization with triethyl orthobenzoate according to general operating instructions 3.

Flash point 135-137° C.

c) 6-Hydroxy-2-phenyl-1-[(3-trifluoromethyl)phenyl]-1H-benzimidazole was obtained by reaction of 6-methoxy-2-phenyl-1-[(3-trifluoromethyl)phenyl]-1H-benzimidazole according to general operating instructions 6.

$^1$H-NMR (D$_6$-DMSO): δ=6.56 ppm d (J=2 Hz, 1H); 6.82 dd (J=8, 2 Hz, 1H); 7.32-7.50 m (5H); 7.60 d (J=8 Hz, 1H); 7.70-7.95 m (4H); 9.48 s (broad)(1H).

6-[[2-Phenyl-1-[3-(trifluoromethyl)phenyl]-1H-benzimidazol-6-yl]oxy]hexanoic acid methyl ester was obtained by reaction of 6-hydroxy-2-phenyl-1-[(3-trifluoromethyl)phenyl]-1H-benzimidazole with 6-bromohexanoic acid methyl ester according to general operating instructions 8.

Flash point 106-108° C.

EXAMPLE 26

6-[[2-Phenyl-1-[3-(trifluoromethyl)phenyl]-1H-benzimidazol-6-yl]oxy]hexanoic acid-isopropylester was obtained by reaction of 6-hydroxy-2-phenyl-1[(3-trifluoromethyl)phenyl]-1H-benzimidazole with 6-bromohexanoic acid isopropyl ester according to general operating instructions 8.

Flash point 113-115° C.

EXAMPLE 27

6-[[2-Phenyl-1-[3-(trifluoromethyl)phenyl]-1H-benzimidazol-6-yl]oxy]hexanoic acid was obtained by reaction of 6-[[2-phenyl-1-[3-(trifluoromethyl)phenyl]-1H-benzimidazol-6-yl]oxy]hexanoic acid methyl ester according to general operating instructions 9.

Flash point 156-158° C.

EXAMPLE 28

6-[[2-Phenyl-1-[3-(trifluoromethyl)phenyl]-1H-benzimidazol-6-yl]oxy]hexan-1-ol was obtained by reaction of 6-[[2-phenyl-1-[3-(trifluoromethyl)phenyl]-1H-benzimidazol-6-yl]oxy]hexanoic acid methyl ester according to general operating instructions 11.

Flash point 143-145° C.

EXAMPLE 29

6-[[1-(3-Cyanophenyl)-2-phenyl-1H-benzimidazol-6-yl]oxy]hexanoic acid methyl ester a) 3-(5-Methoxy-2-nitrophenyl)aminobenzonitrile 2 g of 3-fluoro-4-nitroanisole and 15 ml of 3-aminobenzonitrile were stirred for 65 hours at 140° C. The batch was then diluted with ethyl acetate, washed three times with water and once with saturated sodium chloride solution, dried on sodium sulfate, concentrated by evaporation in a vacuum, and the residue was chromatographed on silica gel.

Flash point 157-158° C.

b) 6-Methoxyl-(3-cyanophenyl)-2-phenyl-1H-benzimidazole was obtained by hydrogenation of 3-(5-methoxy-2-nitrophenyl)aminobenzonitrile according to general operating instructions 1 and subsequent cyclization with triethyl orthobenzoate according to general operating instructions 3. In the cyclization, tetrahydrofuran, contrary to the general operating instructions, was used as a solvent.

Flash point 185-191° C. (decomposition)

c) 6-Hydroxy-1-(3-cyanophenyl)-2-phenyl-1H-benzimidazole was obtained by reaction of 6-methoxyl-(3-cyanophenyl)-2-phenyl-1H-benzimidazole according to general operating instructions 7.

Flash point 216-218° C.

6-[[1-(3-Cyanophenyl)-2-phenyl-1H-benzimidazol-6-yl]oxy]hexanoic acid methyl ester was obtained by reaction of 6-hydroxy-1-(3-cyanophenyl)-2-phenyl-1H-benzimidazole with 6-bromohexanoic acid methyl ester according to general operating instructions 8.
Flash point 115-118° C.

EXAMPLE 30

6-[[1-(3-Cyanophenyl)-2-phenyl-1H-benzimidazol-6-yl]oxy]hexanoic acid isopropyl ester was obtained by reaction of 6-hydroxy-1-(3-cyanophenyl)-2-phenyl-1H-benzimidazole with 6-bromohexanoic acid isopropyl ester according to general operating instructions 8.
Flash point 101-102° C.

EXAMPLE 31

6-[[1-(3-Cyanophenyl)-2-phenyl-1H-benzimidazol-6-yl]oxy]hexanoic acid was obtained by reaction of 6-[[1-(3-cyanophenyl)-2-phenyl-1H-benzimidazol-6-yl]oxy]hexanoic acid methyl-ester according to general operating instructions 9.
Flash point 99-101° C.

EXAMPLE 32

6-[[1-(4-Cyanophenyl)-2-phenyl-1H-benzimidazol-6-yl]oxy]hexanoic acid methyl ester a) 4-(5-Methoxy-2-nitrophenyl)aminobenzonitrile 2 g of 3-fluoro-4-nitroanisole and 15 ml of 4-aminobenzonitrile were stirred for 22 hours at 140° C. The batch was then diluted with ethyl acetate, washed three times with 2N aqueous hydrochloric acid, three times with water and once with saturated sodium chloride solution, dried on sodium sulfate, concentrated by evaporation in a vacuum, and the residue was chromatographed on silica gel.
$^1$H-NMR (CDCl$_3$): δ=3.70 ppm s (3H); 6.38 dd (J=8, 2 Hz, 1H); 6.68 d (J=2 Hz, 1H); 7.27 d (J=8 Hz, 2H); 7.54 d (J=8 Hz, 2H); 8.08 d (J=8 Hz, 1H); 9.60 s (broad)(1H).

b) 6-Methoxyl-(4-cyanophenyl)-2-phenyl-1H-benzimidazole was obtained by hydrogenation of 4-(5-methoxy-2-nitrophenyl)aminobenzonitrile according to general operating instructions 1 and subsequent cyclization with triethyl orthobenzoate according to general operating instructions 3. In the cyclization, tetrahydrofuran, contrary to the general operating instructions, was used as a solvent.
$^1$H-NMR (CDCl$_3$): δ=3.82 ppm s (3H); 6.72 d (J=2 Hz, 1H); 7.00 dd (J=8.2 Hz, 1H); 7.30-7.49 m (7H); 7.78 d (J=8 Hz, 1H); 7.81 d (J=8 Hz, 2H).

c) 6-Hydroxy-1-(4-cyanophenyl)-2-phenyl-1H-benzimidazole was obtained by reaction of 6-methoxy-1-(4-cyanophenyl)-2-phenyl-1H-benzimidazole according to general operating instructions 7.
Flash point 266-268° C.

6-[[1-(4-Cyanophenyl)-2-phenyl-1H-benzimidazol-6-yl]oxy]hexanoic acid methyl ester was obtained by reaction of 6-hydroxy-1-(4-cyanophenyl)-2-phenyl-1H-benzimidazole with 6-bromohexanoic acid methyl ester according to general operating instructions 8.
Flash point 145-148° C.

EXAMPLE 33

-6-[[1-(4-Cyanophenyl)-2-phenyl-1H-benzimidazol-6-yl]oxy]hexanoic acid isopropyl ester was obtained by reaction of 6-hydroxy-1-(4-cyanophenyl)-2-phenyl-1H-benzimidazole with 6-bromohexanoic acid isopropyl ester according to general operating instructions 8.
Flash point 102-103° C.

EXAMPLE 34

6-[[1-(3-Chlorophenyl)-2-phenyl-1H-benzimidazol-6-yl]oxy]hexanoic acid methyl ester a) 1-(3-Chlorophenyl)-6-methoxy-2-phenyl-1H-benzimidazole was obtained by reduction of (3-chlorophenyl)-(5-methoxy-2-nitrophenyl)amine (Belton, McInerney; Proc. R. Ir. Acad. Sect. B: 69; 1970; 21, 27) according to general operating instructions 2 and subsequent cyclization with triethyl orthobenzoate according to general operating instructions 3.
Flash point 140-143° C.

b) 1-(3-Chlorophenyl)-6-hydroxy-2-phenyl-1H-benzimidazole was obtained by reaction of 6-methoxy-1-(3-chlorophenyl)-2-phenyl-1H-benzimidazole according to general operating instructions 6.
Flash point 210-214° C.

6-[[1-3-Chlorophenyl)-2-phenyl-1H-benzimidazol-6-yl]oxy]hexanoic acid methyl ester was obtained by reaction of 1-(3-chlorophenyl)-6-hydroxy-2-phenyl-1H-benzimidazole with 6-bromohexanoic acid methyl ester according to general operating instructions 8.
Flash point 101-105° C.

EXAMPLE 35

6-[[1-(3-Chlorophenyl)-2-phenyl-1H-benzimidazol-6-yl]oxy]hexanoic acid isopropyl ester was obtained by reaction of 1-(3-chlorophenyl)-6-hydroxy-2-phenyl-1H-benzimidazole with 6-bromohexanoic acid isopropyl ester according to general operating instructions 8.
Flash point 107-112° C.

EXAMPLE 36

6-[[1-(3-Chlorophenyl)-2-phenyl-1H-benzimidazol-6-yl]oxy]hexanoic acid was obtained by reaction of 6-[[1-(3-chlorophenyl)-2-phenyl-1H-benzimidazol-6-yl]oxy]hexanoic acid methyl ester according to general operating instructions 9.

¹H-NMR (D₆-DMSO): δ=1.36-1.78 ppm m (6H); 2.24 t (J=7.5 Hz, 2H); 3.96 t (J=7.5 Hz, 2H); 6.68 d (J=2 Hz, 1H); 6.97 dd (J=8.2 Hz, 1H); 7.32-7.65 m (9H); 7.69 d (J=8 Hz, 1H).

EXAMPLE 37

6-[[1-(3-Chlorophenyl)-2-phenyl-1H-benzimidazol-6-yl]oxy]hexan-1-ol was obtained by reaction of 6-[[1-(3-chlorophenyl)-2-phenyl-1H-benzimidazol-6-yl]oxy]hexanoic acid methyl ester according to general operating instructions 11.

¹H-NMR (CDCl₃): δ=1.38-1.88 ppm m (8H); 3.67 t (J=7.5 Hz, 2H); 3.96 t (J=7.5 Hz, 2H); 6.70 d (J=2 Hz, 1H); 6.97 dd (J=8, 2 Hz, 1H); 7.18 ddd (J=8, 2, 2 Hz, 1H); 7.25-7.55 m (8H); 7.76 d (J=8 Hz, 1H).

EXAMPLE 38

6-[[1-(4-Chlorophenyl)-2-phenyl-1H-benzimidazol-6-yl]oxy]hexanoic acid methyl ester a) 1-(4-Chlorophenyl)-6-methoxy-2-phenyl-1H-benzimidazole was obtained by reduction of (4-chlorophenyl)-(5-methoxy-2-nitrophenyl)amine (Kottenhahn et al., J. Org. Chem.; 28; 1963; 3114, 3118) according to general operating instructions 2 and subsequent cyclization with triethyl orthobenzoate according to general operating instructions 3.

¹H-NMR (CDCl₃) δ=3.82 ppm s (3H); 6.67 d (J=2 Hz, 1H); 6.97 dd (J=8, 2 Hz, 1H); 7.22-7.40 m (5H); 7.46-7.55 m (4H); 7.77 d (J=8 Hz, 1H).

b) 1-(4-Chlorophenyl)-6-hydroxy-2-phenyl-1H-benzimidazole was obtained by reaction of 6-methoxy-1-(4-chlorophenyl)-2-phenyl-1H-benzimidazole according to general operating instructions 6.

¹H-NMR (D₆-DMSO): δ=6.60 ppm d (J=2 Hz, 1H); 6.87 dd (J=8, 2 Hz, 1H); 7.40-7.56 m (7H); 7.64 d (J=8 Hz, 1H); 7.70 d (J=8 Hz, 2H); 9.50 s (broad)(1H).

6-[[1-(4-Chlorophenyl)-2-phenyl-1H-benzimidazol-6-yl]oxy]hexanoic acid methyl ester was obtained by reaction of 1-(4-chlorophenyl)-6-hydroxy-2-phenyl-1H-benzimidazole with 6-bromohexanoic acid methyl ester according to general operating instructions 8.
Flash point 100-104° C.

EXAMPLE 39

6-[[1-(4-Chlorophenyl)-2-phenyl-1H-benzimidazol-6-yl]oxy]hexanoic acid isopropyl ester was obtained by reaction of 1-(4-chlorophenyl)-6-hydroxy-2-phenyl-1H-benzimidazole with 6-bromohexanoic acid isopropyl ester according to general operating instructions 8.
Flash point 83-88° C.

EXAMPLE 40

6-[[1-(4-Chlorophenyl)-2-phenyl-1H-benzimidazol-6-yl]oxy]hexanoic acid was obtained by reaction of 6-[[1-(4-chlorophenyl)-2-phenyl-1H-benzimidazol-6-yl]oxy]hexanoic acid methyl ester according to general operating instructions 9.

¹H-NMR (D₆-DMSO): δ=1.35-1.78 ppm m (6H); 2.25 t (J=7.5 Hz, 2H); 3.94 t (J=7.5 Hz, 2H); 6.68 d (J=2 Hz, 1H); 6.95 dd (J=8, 2 Hz, 1H); 7.33-7.54 m (7H); 7.63 d (J=8 Hz, 2H); 7.69 d (J=8 Hz, 1H).

EXAMPLE 41

6-[[1-(4-Chlorophenyl)-2-phenyl-1H-benzimidazol-6-yl]oxy]hexan-1-ol was obtained by reaction of 6-[[1-(4-chlorophenyl)-2-phenyl-1H-benzimidazol-6-yl]oxy]hexanoic acid methyl ester according to general operating instructions 11.
Flash point 115-120° C.

EXAMPLE 42

6-[[1-(2-Methylphenyl)-2-phenyl-1H-benzimidazol-6-yl]oxy]hexanoic acid methyl ester a) 5-Chloro-2-nitrophenyl-o-tolylamine 81 ml of o-toluidine was added to absolution of 10 g of 1-chloro-3,4-dinitrobenzene in 50 ml of ethanol, and it was refluxed for 72 hours. It was concentrated by evaporation in a vacuum, the residue was taken up in ethyl acetate and 2N aqueous hydrochloric acid. The organic phase was extracted three more times with 2N aqueous hydrochloric acid, dried on sodium sulfate and concentrated by evaporation in a vacuum. The residue was purified by chromatography on silica gel.

¹H-NMR (CDCl₃): δ=2.28 ppm s (3H); 6.70 dd (J=10, 2 Hz, 1H); 6.80 d (J=2 Hz, 1H); 7.22-7.40 m (4H); 8.18 d (J=10 Hz, 1H); 9.40 s (broad)(1H).

b) 5-Methoxy-2-nitrophenyl-o-tolylamine 1 g of 5-chloro-2-nitrophenyl-o-tolylamine was added to a solution of 1 g of sodium in 20 ml of methanol, and it was refluxed for 72 hours. Then, it is cooled to 0° C., and the crystalline product is suctioned off.

¹H-NMR (CDCl₃): δ=2.30 ppm s (3H); 3.72 s (3H); 6.19 d (J=2 Hz, 1H); 6.32 dd (J=10, 2 Hz, 1H); 7.20-7.40 m (4H); 8.20 d (J=10 Hz, 1H); 9.62 s (broad)(1H).

c) 6-Methoxy-1-(2-methylphenyl)-2-phenyl-1H-benzimidazole was obtained by reaction of 5-methoxy-2-nitrophenyl-o-tolylamine according to general operating instructions 1 and subsequent cyclization with triethyl orthobenzoate according to general operating instructions 3.

¹H-NMR (CDCl₃): δ=1.93 ppm s (3H); 3.78 s (3H); 6.42 d (J=2 Hz, 1H); 6.97 dd (J=8, 2 Hz, 1H); 7.22-7.48 m (7H); 7.57 dd (J=8, 1 Hz, 2H); 7.78 d (J=8 Hz, 1H).

6-[[1-(2-Methylphenyl)-2-phenyl-1H-benzimidazol-6-yl]oxy]hexanoic acid methyl ester 6-Methoxy-1-(2-methylphenyl)-2-phenyl-1H-benzimidazole was reacted according to general operating instructions 6. The crude product was reacted with 6-bromohexanoic acid methyl ester according to general operating instructions 8.

$^1$H-NMR (CDCl$_3$): δ=1.43-1.58 ppm m (2H); 1.62-1.84 m (4H); 1.93 s (3H); 2.34 t (J=7.5 Hz, 2H); 3.68 s (3H); 3.90 t (J=7.5 Hz, 2H); 6.42 d (J=2 Hz, 1H); 6.96 dd (J=8, 2 Hz, 1H); 7.22-7.48 m (7H); 7.56 dd (J=8, 1.5 Hz, 2H); 7.76 d (J=8 Hz, 1H).

EXAMPLE 43

6-[[1-(2-Methylphenyl)-2-phenyl-1H-benzimidazol-6-yl]oxy]hexanoic acid was obtained by reaction of 6-[[1-(2-methylphenyl)-2-phenyl-1H-benzimidazol-6-yl]oxy]hexanoic acid methyl ester according to general operating instructions 9.

Flash point 198-200° C.

EXAMPLE 44

6-[[1-(3-Methylphenyl)-2-phenyl-1H-benzimidazol-6-yl]oxy]hexanoic acid methyl ester a) 5-Chloro-2-nitrophenyl-m-tolylamine 81 ml of m-toluidine is added to a solution of 50 g of 1-chloro-3,4-dinitrobenzene in 250 ml of ethanol, and the solution was allowed to stand for 72 hours. The reaction mixture was filtered, and the crystallizate was washed with cold ethanol and 2N aqueous hydrochloric acid. It was purified by chromatography on silica gel.

$^1$H-NMR (CDCl$_3$): δ=2.40 ppm s (3H); 6.72 dd (J=10, 2 Hz, 1H); 7.04-7.13 m (3H); 7.14 d (J=2 Hz, 1H), 7.32 t (J=10 Hz, 1H); 8.18 d (J=10 Hz, 1H); 9.52 s (broad)(1H).

b) 5-Methoxy-2-nitrophenyl-m-tolylamine 39 g of 5-chloro-2-nitrophenyl-m-tolylamine was added to a solution of 9 g of sodium in 670 ml of methanol, and it was refluxed for 72 hours. Then, it is cooled to 0° C., and the crystalline product is suctioned off.

$^1$H-NMR (CDCl$_3$): δ=2.40 ppm s (3H); 3.73 s (3H); 6.33 dd (J=10, 2 Hz, 1H); 6.58 d (J=2 Hz, 1H); 7.03-7.15 m (3H); 7.31 t (J=10 Hz, 1H); 8.19 d (J=10 Hz, 1H); 9.72 s (broad)(1H).

c) 6-Methoxy-1-(3-methylphenyl)-2-phenyl-1H-benzimidazole was obtained by reaction of 5-methoxy-2-nitrophenyl-m-tolylamine according to general operating instructions 1 and subsequent cyclization with triethyl orthobenzoate according to general operating instructions 3.

$^1$H-NMR (CDCl$_3$): δ=2.42 ppm s (3H); 3.81 s (3H); 6.69 d (J=2 Hz, 1H); 7.03 dd (J=8, 2 Hz, 1H); 7.10-7.18 m (2H); 7.30-7.48 m (5H); 7.62 dd (J=8, 1 Hz, 2H); 7.89 d (J=8 Hz, 1H).

d) 6-Hydroxy-1-(3-methylphenyl)-2-phenyl-1H-benzimidazole was obtained by reaction of 6-methoxy-1-(3-methylphenyl)-2-phenyl-1H-benzimidazole according to general operating instructions 6.

$^1$H-NMR (D$_6$-DMSO): δ=2.34 ppm s (3H); 6.52 d (J=2 Hz, 1H); 6.80 dd (J=8, 2 Hz, 1H); 7.15 d (J=8 Hz, 1H); 7.28 s (broad)(1H); 7.32-7.55 m (7H); 7.59 d (J=8 Hz, 1H); 9.37 s (broad)(1H).

6-[[1-(3-Methylphenyl)-2-phenyl-1H-benzimidazol-6-yl]oxy]hexanoic acid methyl ester was obtained by reaction of 6-hydroxy-1-(3-methylphenyl)-2-phenyl-1H-benzimidazole with 6-bromohexanoic acid methyl ester according to general operating instructions 8.

$^1$H-NMR (CDCl$_3$): δ=1.44-1.58 ppm m (2H); 1.64-1.85 m (4H); 2.35 t (J=7.5 Hz, 2H); 2.40 s (3H); 3.68 s (3H); 3.95 t (J=7.5 Hz, 2H); 6.70 d (J=2 Hz, 1H); 6.96 dd (J=8, 2 Hz, 1H); 7.10 d (J=8 Hz, 1H); 7.16 S (broad)(2H); 7.25-7.43 m (4H); 7.55 dd (J=8, 1 Hz, 2H); 7.77 d (J=8 Hz, 1H).

EXAMPLE 45

6-[[1-(3-Methylphenyl)-2-phenyl-1H-benzimidazol-6-yl]oxy]hexanoic acid isopropyl ester was obtained by reaction of 6-hydroxy-1-(3-methylphenyl)-2-phenyl-1H-benzimidazole with 6-bromohexanoic acid isopropylester according to general operating instructions 8.

$^1$H-NMR (CDCl$_3$): δ=1.22 ppm d (J=8 Hz, 6H); 1.44-1.56 m (2H, CH$_2$); 1.64-1.84 m (4H, CH$_2$); 2.30 t (J=7.5 Hz, 2H); 2.41 s (3H); 3.95 t (J=7.5 Hz, 2H); 5.00 sp (J=8 Hz, 1H); 6.68 d (J=2 Hz, 1H); 6.96 dd (J=8, 2 Hz, 1H); 7.10 d (J=8 Hz, 1H); 7.14 s (broad)(1H); 7.25-7.41 m (4H); 7.54 dd (J=8, 1 Hz, 2H); 7.75 d (J=8 Hz, 1H).

EXAMPLE 46

6-[[1-(3-Methylphenyl)-2-phenyl-1H-benzimidazol-6-yl]oxy]hexanoic acid was obtained by reaction of 6-[[1-(3-methylphenyl)-2-phenyl-1H-benzimidazol-6-yl]oxy]hexanoic acid methyl ester according to general operating instructions 9.

$^1$H-NMR (D$_6$-DMSO): δ=1.38-1.80 ppm m (6H); 2.23 t (J=7.5 Hz, 2H); 3.84-3.93 m (2H); 6.60 d (J=2 Hz, 1H); 6.87 d (broad) (J=8 Hz, 1H); 7.15 d (J=8 Hz, 2H); 7.20-7.32 m (4H); 7.42-7.50 m (2H); 7.59 d (J=8 Hz, 1H); 7.77 d (J=8 Hz, 1H).

EXAMPLE 47

6-[[1-(3-Methylphenyl)-2-phenyl-1H-benzimidazol-6-yl]oxy]hexan-1-ol was obtained by reaction of 6-[[1-(3-methylphenyl)-2-phenyl-1H-benzimidazol-6-yl]oxy]hexanoic acid methyl ester according to general operating instructions 11.

$^1$H-NMR (CDCl$_3$): δ=1.40-1.85 m (8H); 2.40 s (3H); 3.68 t (J=7.5 Hz, 2H); 3.96 t (J=7.5 Hz, 2H); 6.69 d (J=1.5 Hz, 1H); 6.96 dd (J=8, 1.5 Hz, 1H); 7.10 d (J=8 Hz, 1H); 7.13 s (broad)(1H); 7.25-7.42 m (5H); 7.54 dd (J=8, 1 Hz, 2H); 7.76 d (J=8 Hz, 1H).

EXAMPLE 48

6-[[1-(4-Methylphenyl)-2-phenyl-1H-benzimidazol-6-yl]oxy]hexanoic acid methyl ester a) 5-Chloro-2-nitrophenyl-p-tolylamine was produced analogously to 5-chloro-2-nitrophenyl-m-tolylamine from 1-chloro-3,4-dinitrobenzene and p-toluidine. It was purified by crystallization.

$^1$H-NMR (CDCl$_3$): δ=2.40 ppm s (3H); 6.70 dd (J=10, 2 Hz, 1H), 7.08 d (J=2 Hz, 1H); 7.16 d (J=10 Hz, 2H); 7.28 d (J=10 Hz, 2H); 8.18 d (J=10 Hz, 1H); 9.50 s (broad)(1H).

b) 5-Methoxy-2-nitrophenyl-p-tolylamine was produced analogously to 5-methoxy-2-nitrophenyl-m-tolylamine from 5-chloro-2-nitrophenyl)-p-tolylamine and sodium methanolate.

$^1$H-NMR (CDCl$_3$): δ=2.39 ppm s (3H); 3.72 s (3H); 6.31 dd (J=10, 2 Hz, 1H); 6.50 d (J=2 Hz, 1H); 7.19 d (J=10 Hz, 2H); 7.25 d (J=10 Hz, 2H); 8.19 d (J=10 Hz, 1H); 9.70 s (broad)(1H).

c) 6-Methoxy-1-(4-methylphenyl)-2-phenyl-1H-benzimidazole was obtained by reaction of 5-methoxy-2-nitrophenyl-p-tolylamine according to general operating instructions 1 and subsequent cyclization with triethyl orthobenzoate according to general operating instructions 3.

$^1$H-NMR (CDCl$_3$): δ=2.49 ppm s (3H); 3.80 s (3H); 6.69 d (J=2 Hz, 1H); 6.97 dd (J=8, 2 Hz, 1H); 7.20 d (broad)(J=8 Hz, 2H); 7.25-7.36 m (5H); 7.53 dd (J=8, 1 Hz, 2H); 7.76 d (J=8 Hz, 1H).

d) 6-Hydroxy-1-(4-methylphenyl)-2-phenyl-1H-benzimidazole was obtained by reaction of 6-methoxy-1-(4-methylphenyl)-2-phenyl-1H-benzimidazole according to general operating instructions 6.

$^1$H-NMR (D$_6$-DMSO): δ=2.40 ppm s (3H); 6.50 d (J=2 Hz, 1H); 6.80 dd (J=8, 2 Hz, 1H); 7.28 d (J=8 Hz, 2H); 7.32-7.43 m (5H); 7.46-7.52 m (2H); 7.56 d (J=8 Hz, 1H); 9.28 s (broad)(1H).

6-[[1-(4-Methylphenyl)-2-phenyl-1H-benzimidazol-6-yl]oxy]hexanoic acid methyl ester was obtained by reaction of 6-hydroxy-1-(4-methylphenyl)-2-phenyl-1H-benzimidazole with 6-bromohexanoic acid methyl ester according to general operating instructions 8.

$^1$H-NMR (CDCl$_3$): δ=1.44-1.58 ppm m (2H); 1.62-1.86 m (4H); 2.34 t (J=7.5 Hz, 2H); 2.48 s (3H); 3.68 s (3H); 3.94 t (J=7.5 Hz, 2H); 6.69 d (J=2 Hz, 1H); 6.96 dd (J=8, 2 Hz, 1H); 7.19 d (J=8 Hz, 2H); 7.28-7.38 m (5H); 7.55 dd (J=8, 1 Hz, 2H); 7.75 d (J=8 Hz, 1H).

EXAMPLE 49

6-[[1-(4-Methylphenyl)-2-phenyl-1H-benzimidazol-6-yl]oxy]hexanoic acid isopropyl ester was obtained by reaction of 6-hydroxy-1-(4-methylphenyl)-2-phenyl-1H-benzimidazole with 6-bromohexanoic acid isopropyl ester according to general operating instructions 8.

$^1$H-NMR (CDCl$_3$): δ=1.22 ppm d (J=7.5 Hz, 6H); 1.44-1.56 m (2H); 1.62-1.85 m (4H); 2.30 t (J=7.5 Hz, 2H); 2.47 s (3H); 3.93 t (J=7.5 Hz, 2H); 5.01 sp (J=7.5 Hz, 1H); 6.68 d (J=2 Hz, 1H); 6.96 dd (J=8, 2 Hz, 1H); 7.20 d (J=8 Hz, 2H); 7.26-7.36 m (5H); 7.55 dd (J=8, 1 Hz, 2H); 7.75 d (J=8 Hz, 1H).

EXAMPLE 50

6-[[1-(4-Methylphenyl)-2-phenyl-1H-benzimidazol-6-yl]oxy]hexanoic acid was obtained by reaction of 6-[[1-(4-methylphenyl)-2-phenyl-1H-benzimidazol-6-yl]oxy]hexanoic acid methyl ester according to general operating instructions 9.

Flash point 186-190° C.

EXAMPLE 51

6-[[1-(4-Methylphenyl)-2-phenyl-1H-benzimidazol-6-yl]oxy]hexan-1-ol was obtained by reaction of 6-[[1-(4-methylphenyl)-2-phenyl-1H-benzimidazol-6-yl]oxy]hexanoic acid methyl ester according to general operating instructions 11.

$^1$H-NMR (CDCl$_3$): δ=1.38-1.80 m (8H); 2.47 s (3H); 3.65 t (J=7.5 Hz, 2H); 3.93 t (J=7.5 Hz, 2H); 6.68 d (J=2 Hz, 1H); 6.97 dd (J=8, 2 Hz, 1H); 7.18 d (J=8 Hz, 2H); 7.24-7.37 m (5H); 7.54 dd (J=8, 1 Hz, 2H); 7.75 d (J=8 Hz, 1H).

EXAMPLE 52

6-[[1-(3,4-Dimethylphenyl)-2-phenyl-1H-benzimidazol-6-yl]oxy]hexanoic acid methyl ester a) 3-(3,4-Dimethylphenyl)amino-4-nitrophenol 3 g of 3-fluoro-4-nitrophenol and 6.9 g of 3,4-dimethylaniline were mixed and stirred for 2 hours at 150° C. After cooling, it was dissolved in dichloromethane and extracted six times with 1N aqueous hydrochloric acid. The organic phase was discarded, and the combined aqueous phases were extracted three times with chloroform. The combined extracts were dried on sodium sulfate, concentrated by evaporation in a vacuum, and the residue was chromatographed on silica gel.

$^1$H-NMR (CDCl$_3$/D$_6$-DMSO): δ=2.18 ppm s (6H); 6.13 dd (J=8, 2 Hz, 1H); 6.36 d (J=2 Hz, 1H); 6.90-7.00 m (2H); 7.09 d (J=8 Hz, 1H); 7.93 d (J=8 Hz, 1H); 9.50 s (broad)(1H); 10.19 s (broad)(1H).

b) 6-[3-(3,4-Dimethylphenyl)amino-4-nitrophenyl]oxyhexanoic acid methyl ester was obtained by reaction of 3-(3,4-dimethylphenyl)amino-4-nitrophenol with 6-bromohexanoic acid methyl ester according to general operating instructions 8.

$^1$H-NMR (CDCl$_3$): δ=1.38-1.52 ppm m (2H); 1.59-1.80 m (4H); 2.30 s (6H); 2.33 t (J=7.5 Hz, 2H); 3.68 s (3H); 3.87 t (J=7.5 Hz, 2H); 6.28 d (J=8, 2 Hz, 1H); 6.48 d (J=2 Hz, 1H); 7.04 d (J=8 Hz, 1H); 7.06 s (broad)(1H); 7.18 d (J=8 Hz, 1H); 8.17 d (J=8 Hz, 1H); 9.71 s (broad)(1H).

6-[[1-(3,4-Dimethylphenyl)-2-phenyl-1H-benzimidazol-6-yl]oxy]hexanoic acid methyl ester was obtained by reaction of 6-[3-(3,4-dimethylphenyl)amino-4-nitrophenyl]oxyhexanoic acid methyl ester according to general operating instructions 1 and subsequent cyclization with triethyl orthobenzoate according to general operating instructions 3.

$^1$H-NMR (CDCl$_3$): δ=1.44-1.56 ppm m (2H); 1.62-1.84 m (4H); 2.30 s (3H); 2.33 t (J=7.5 Hz, 2H); 2.34 s (3H); 3.68 s (3H); 3.93 t (J=7.5 Hz, 2H); 6.67 d (J=2 Hz, 1H); 6.94 dd (J=8, 2 Hz, 1H); 7.03 dd (J=8, 1.5 Hz, 1H); 7.09 s (broad) (1H); 7.22-7.35 m (4H); 7.57 dd (J=8, 1.5 Hz, 2H); 7.76 d (J=8 Hz, 1H).

EXAMPLE 53

6-[[1-(3,4-Dimethylphenyl)-2-phenyl-1H-benzimidazol-6-yl]oxy]hexanoic acid was obtained by reaction of 6-[[1-(3,4-dimethylphenyl)-2-phenyl-1H-benzimidazol-6-yl]oxy]hexanoic acid methyl ester according to general operating instructions 9.
Flash point 158-161° C.

EXAMPLE 54

6-[[1-(3,5-Dimethylphenyl)-2-phenyl-1H-benzimidazol-6-yl]oxy]hexanoic acid methyl ester a) 3-(3,5-Dimethylphenyl)amino-4-nitrophenol 5.4 g of 3-fluoro-4-nitrophenol and 4.3 ml of 3,5-dimethylaniline were mixed and stirred for 6 hours at 120° C. After cooling, it was taken up in ethyl acetate and water and extracted three times with 1N aqueous hydrochloric acid. The combined aqueous phases were extracted three times with ethyl acetate. The combined organic phases were dried on sodium sulfate, concentrated by evaporation in a vacuum, and the residue was crystallized.

$^1$H-NMR (D$_6$-DMSO): δ=2.30 ppm s (6H); 6.28 dd (J=8, 2 Hz, 1H); 6.49 d (J=2 Hz, 1H); 6.52 d (J=2 Hz, 1H); 6.90 s (broad)(1H); 6.98 s (broad)(2H); 8.04 d (J=8 Hz, 1H); 9.51 s (broad)(1H).

b) 6-[3-(3,5-Dimethylphenyl)amino-4-nitrophenyl]oxyhexanoic acid methyl ester was obtained by reaction of 3-(3,5-dimethylphenyl)amino-4-nitrophenol with 6-bromohexanoic acid methyl ester according to general operating instructions 8.

$^1$H-NMR (CDCl$_3$): δ=1.40-1.52 ppm m (2H); 1.60-1.80 m (4H); 2.30 t (J=7.5 Hz, 2H); 2.32 s (6H); 3.68 s (3H); 3.88 t (J=7.5 Hz, 2H); 6.30 dd (J=8, 2 Hz, 1H); 6.52 d (J=2 Hz, 1H); 6.88 s (broad)(1H); 6.91 s (broad)(2H); 8.17 d (J=8 Hz, 1H); 9.69 s (broad)(1H).

6-[3-(3,5-Dimethylphenyl)amino-4-nitrophenyl]oxyhexanoic acid methyl ester was obtained by reaction of 6-[3-(3,5-dimethylphenyl)amino-4-nitrophenyl]oxyhexanoic acid methyl ester according to general operating instructions 1 and subsequent cyclization with triethyl orthobenzoate according to general operating instructions 3.
Flash point 124-126° C.

EXAMPLE 55

6-[[1-(3,5-Dimethylphenyl)-2-phenyl-1H-benzimidazol-6-yl]oxy]hexanoic acid was by reaction of 6-[3-(3,5-dimethylphenyl)amino-4-nitrophenyl]oxyhexanoic acid methyl ester according to general operating instructions 9.
Flash point 162-164° C.

EXAMPLE 56

6-[[1-(3,5-Dimethylphenyl)-2-phenyl-1H-benzimidazol-6-yl]oxy]hexanoic acid isopropyl ester was by reaction of 6-[3-(3,5-dimethylphenyl)amino-4-nitrophenyl]oxyhexanoic acid with isopropanol according to general operating instructions 10.
Flash point 98-101° C.

EXAMPLE 57

6-[[1-(3-Methoxyphenyl)-2-phenyl-1H-benzimidazol-6-yl]oxy]hexanoic acid methyl ester a) 3-(3-Methoxyphenyl)amino-4-nitrophenol 4 g of 3-fluoro-4-nitrophenol and 9.4 g of m-anisidine were mixed and stirred for 2.5 hours at 150° C. After cooling, it was dissolved in dichloromethane and extracted three times with 1N aqueous hydrochloric acid. The organic phase was dried on sodium sulfate, concentrated by evaporation in a vacuum, and the residue was chromatographed on silica gel.

$^1$H-NMR (CDCl$_3$): δ=3.83 ppm s (3H); 6.30 dd (J=10, 2 Hz, 1H); 6.57 d (J=2 Hz, 1H); 6.70-6.84 m (2H); 6.89 d (broad)(J=10 Hz, 1H); 7.32 t (J=10 Hz, 1H); 8.19 d (J=10 Hz, 1H); 9.68 s (broad)(1H); 9.69 s (broad).

b) 6-[3-(3-Methoxyphenyl)amino-4-nitrophenyl]oxyhexanoic acid methyl ester was obtained by reaction of 3-(3-methoxyphenyl)amino-4-nitrophenol with 6-bromohexanoic acid methyl ester according to general operating instructions 8.

$^1$H-NMR (CDCl$_3$): δ=1.42-1.58 ppm m (2H); 1.60-1.93 m (4H); 2.34 t (J=7.5 Hz, 2H); 3.68 s (3H); 3.80 s (3H); 4.03 t (J=7.5 Hz, 2H); 6.32 dd (J=10, 2 Hz, 1H); 6.59 d (J=2 Hz, 1H); 6.68-6.84 m (2H); 6.90 d (broad)(J=8 Hz, 1H): 7.32 t (J=8 Hz, 1H); 8.19 d (J=10 Hz, 1H); 9.70 s (broad)(1H).

6-[[1-(3-Methoxyphenyl)-2-phenyl-1H-benzimidazol-6-yl]oxy]hexanoic acid methyl ester was obtained by reaction of 6-[3-(3-methoxyphenyl)amino-4-nitrophenyl]oxyhexanoic acid methyl ester according to general operating instructions 1 and subsequent cyclization with triethyl orthobenzoate according to general operating instructions 3.

$^1$H-NMR (CDCl$_3$): δ=1.44-1.58 ppm m (2H); 1.62-1.86 m (4H); 2.34 t (J=7.5 Hz, 2H); 3.68 s (3H); 3.78 s (3H); 3.95 t (J=7.5 Hz, 2H); 6.71 d (J=1.5 Hz, 1H); 6.83 dd (J=1.5, 1.5 Hz, 1H); 6.90 dd (J=8, 1.5 Hz, 1H); 6.94 dd (J=8, 1.5 Hz, 1H); 7.01 dd (J=8, 1.5 Hz, 1H); 7.27-7.36 m (3H); 7.40 t (J=8 Hz, 1H); 7.56 dd (J=8, 2 Hz, 2H); 7.74 d (J=8 Hz, 1H).

EXAMPLE 58

6-[[1-(3-Methoxyphenyl)-2-phenyl-1H-benzimidazol-6-yl]oxy]hexanoic acid was obtained by reaction of 6-[[1-(3-methoxyphenyl)-2-phenyl-1H-benzimidazol-6-yl]oxy]hexanoic acid methyl ester according to general operating instructions 9.

Flash point 149-152° C.

EXAMPLE 59

6-[[1-(4-Methoxyphenyl)-2-phenyl-1H-benzimidazol-6-yl]oxy]hexanoic acid methyl ester a) 3-(4-Methoxyphenyl)amino-4-nitrophenol 0.16 g of 3-fluoro-4-nitrophenol and 0.37 g of p-anisidine were mixed and stirred for 1.5 hours at 150° C. After cooling, it was dissolved in dichloromethane, and extracted twice with 1N aqueous hydrochloric acid and once with saturated sodium chloride solution. The organic phase was dried on sodium sulfate and concentrated by evaporation in a vacuum.

$^1$H-NMR (CDCl$_3$/D$_6$-DMSO): δ=3.57 ppm s (3H); 6.06 dd (J=10, 2 Hz, 1H); 6.18 d (J=2 Hz, 1H); 6.77 d (J=10 Hz, 2H); 7.03 d (J=10 Hz, 2H); 7.89 d (J=10 Hz, 1H); 9.40 s (broad)(1H); 9.80 s (broad).

b) 6-[3-(4-Methoxyphenyl)amino-4-nitrophenyl]oxyhexanoic acid methyl ester was obtained by reaction of 3-(4-methoxyphenyl)amino-4-nitrophenol with 6-bromohexanoic acid methyl ester according to general operating instructions 8.

$^1$H-NMR (CDCl$_3$): δ=1.38-1.50 ppm m (2H); 1.60-1.80 m (4H); 2.33 t (J=7.5 Hz, 2H); 3.67 s (3H); 3.85 t (J=7.5 Hz, 2H); 3.88 s (3H); 6.29 dd (J=10, 1.5 Hz, 1H); 6.30 d (J=1.5 Hz, 1H); 6.98 d (J=10 Hz, 2H); 7.20 d (J=10 Hz, 2H); 8.18 d (J=10 Hz, 1H); 9.63 s (broad)(1H).

6-[[1-(4-Methoxyphenyl)-2-phenyl-1H-benzimidazol-6-yl]oxy]hexanoic acid methyl ester was obtained by reaction of 6-[3-(4-methoxyphenyl)amino-4-nitrophenyl]oxyhexanoic acid methyl ester according to general operating instructions 1 and subsequent cyclization with triethyl orthobenzoate according to general operating instructions 3.

Flash point 98-102° C.

EXAMPLE 60

6-[[1-(4-Methoxyphenyl)-2-phenyl-1H-benzimidazol-6-yl]oxy]hexanoic acid was obtained by reaction of 6-[[1-(4-methoxyphenyl)-2-phenyl-1H-benzimidazol-6-yl]oxy]hexanoic acid methyl ester according to general operating instructions 9.

Flash point 160-165° C.

EXAMPLE 61

6-[[1-(3,4-Dimethoxyphenyl)-2-phenyl-1H-benzimidazol-6-yl]oxy]hexanoic acid methyl ester a) 3-(3,4-Dimethoxyphenyl)amino-4-nitrophenol 3 g of 3-fluoro-4-nitrophenol and 8.8 g of 3,4-dimethoxyaniline were mixed and stirred for 2 hours at 150° C. After cooling, it was dissolved in dichloromethane and extracted twice with 1N aqueous hydrochloric acid. The aqueous phase was extracted twice with chloroform, and the combined chloroform extracts were dried on sodium sulfate and concentrated by evaporation in a vacuum.

$^1$H-NMR (D$_6$-DMSO): δ=3.75 ppm s (3H); 3.78 s (3H); 6.25 dd (J=10, 2 Hz, 1H); 6.35 d (J=2 Hz, 1H); 6.88 dd (J=8, 1.5 Hz, 1H); 6.98 d (J=1.5 Hz, 1H); 7.05 d (J=8 Hz, 1H); 8.04 d (J=10 Hz, 1H); 9.52 s (broad)(1H); 10.72 s (broad).

b) 6-[3-(3,4-Dimethoxyphenyl)amino-4-nitrophenyl]oxyhexanoic acid methyl ester was obtained by reaction of 3-(3,4-dimethoxyphenyl)amino-4-nitrophenol with 6-bromohexanoic acid methyl ester according to general operating instructions 8.

$^1$H-NMR (CDCl$_3$): δ=1.40-1.52 ppm m (2H); 1.60-1.80 m (4H); 2.32 t (J=7.5 Hz, 2H); 3.68 s (3H); 3.85 t (J=7.5 Hz, 2H); 3.88 s (3H); 3.93 s (3H); 6.29 dd (J=10, 1.5 Hz, 1H); 6.33 d (J=1.5 Hz, 1H); 6.80 d (J=1.5 Hz, 1H); 6.87 dd (J=10, 1.5 Hz, 1H); 6.92 d (J=10 Hz, 1H); 8.18 d (J=10 Hz, 1H); 9.68 s (broad)(1H).

6-[[1-(3,4-Dimethoxyphenyl)-2-phenyl-1H-benzimidazol-6-yl]oxy]hexanoic acid methyl ester was obtained by reaction of 6-[3-(3,4-dimethoxyphenyl)amino-4-nitrophenyl]oxyhexanoic acid methyl ester according to general operating instructions 1 and subsequent cyclization with triethyl orthobenzoate according to general operating instructions 3.

Flash point 116-118° C.

EXAMPLE 62

6-[[1-(3,4-Dimethoxyphenyl)-2-phenyl-1H-benzimidazol-6-yl]oxy]hexanoic acid was obtained by reaction of 6-[[1-(3,4-dimethoxyphenyl)-2-phenyl-1H-benzimidazol-6-yl]oxy]hexanoic acid methyl ester according to general operating instructions 9.

Flash point 158-161° C.

EXAMPLE 63

6-[[1-[3,4-(Methylenedioxy)phenyl]-2-phenyl-1H-benzimidazol-6-yl]oxy]hexanoic acid methyl ester a) 3-(3,4-Methylenedioxyphenyl)amino-4-nitrophenol 0.86 g of 3-fluoro-4-nitrophenol and 2.25 g of 3,4-methylenedioxyaniline were mixed and stirred for 5 hours at 120° C. The raw mixture was chromatographed on silica gel.

$^1$H-NMR (D$_6$-DMSO): δ=6.02 ppm s (2H); 6.25 dd (J=10, 2 Hz, 1H); 6.33 d (J=2 Hz, 1H); 6.72 dd (J=8, 1.5 Hz, 1H); 6.87 d (J=1.5 Hz, 1H); 7.65 d (J=10 Hz, 1H); 8.18 d (J=10 Hz, 1H); 9.52 s (broad)(1H).

b) 6-[3-(3,4-Methylenedioxyphenyl)amino-4-nitrophenyl]oxyhexanoic acid methyl ester was obtained by reaction of 3-(3,4-methylenedioxyphenyl)amino-4-nitrophenol with 6-bromohexanoic acid methyl ester according to general operating instructions 8.

Flash point 108-111° C.

6-[[1-(3,4-Methylenedioxyphenyl)-2-phenyl-1H-benzimidazol-6-yl]oxy]hexanoic acid methyl ester was obtained by reaction of 6-[3-(3,4-methylenedioxyphenyl)amino-4-nitrophenyl]oxyhexanoic acid methyl ester according to general operating instructions 1 and subsequent cyclization with triethyl orthobenzoate according to general operating instructions 3.

$^1$H-NMR (CDCl$_3$): δ=1.43-1.55 ppm m (2H); 1.65-1.82 m (4H); 2.35 t (J=7.5 Hz, 2H); 3.68 s (3H); 3.95 t (J=7.5 Hz, 2H); 6.10 s (2H); 6.65 d (J=1.5 Hz, 1H); 6.72-6.83 m (2H); 6.90 d (J=10 Hz, 1H); 6.93 dd (J=10, 1.5 Hz, 1H); 7.29-7.38 m (3H); 7.52-7.62 m (2H); 7.72 d (J=10 Hz, 1H).

EXAMPLE 64

6-[[1-[3,4-(Methylenedioxy)phenyl]-2-phenyl-1H-benzimidazol-6-yl]oxy]hexanoic acid was obtained by reaction of 6-[[1-(3,4-methylenedioxyphenyl)-2-phenyl-1H-benzimidazol-6-yl]oxy]hexanoic acid methyl ester according to general operating instructions 9.

Flash point 130° C.

EXAMPLE 65

6-[[2-Phenyl-1-(3,4,5-trimethoxyphenyl)-1H-benzimidazol-6-yl]oxy]hexanoic acid methyl ester a) 3-(3,4,5-Trimethoxyphenyl)amino-4-nitrophenol 3.7 g of 3-fluoro-4-nitrophenol and 4.76 g of 3,4,5-trimethoxyaniline were mixed and stirred for 10 hours at 100° C. After cooling, it was taken up in ethyl acetate and water and extracted three times with ethyl acetate. The combined organic phases were extracted three times with 1N aqueous hydrochloric acid and once with saturated sodium chloride solution, dried on sodium sulfate and concentrated by evaporation to a very large extent in a vacuum. The product was digested with diisopropyl ether.

$^1$H-NMR (D$_6$-DMSO): δ=3.70 ppm s (3H); 3.80 s (6H); 6.28 dd (J=10, 2 Hz, 1H); 6.53 d (J=2 Hz, 1H); 6.70 s (2H); 8.05 d (J=10 Hz, 1H); 9.50 s (broad)(1H); 10.71 s (broad).

b) 6-[4-Nitro-3-[(3,4,5-trimethoxyphenyl)amino]-phenyl]oxyhexanoic acid methyl ester was obtained by reaction of 4-nitro-3-[(3,4,5-trimethoxyphenyl)amino]phenol with 6-bromohexanoic acid methyl ester according to general operating instructions 8.

$^1$H-NMR (CDCl$_3$): δ=1.40-1.53 ppm m (2H); 1.60-182 m (4H); 2.32 t (J=7.5 Hz, 2H); 3.67 s (3H); 3.85 s (6H); 3.88 t (J=7.5 Hz, 2H); 3.90 s (3H); 6.30 dd (J=10, 1.5 Hz, 1H); 6.50 d (J=1.5 Hz, 1H); 6.52 s (2H); 8.18 d (J=10 Hz, 1H); 9.68 s (broad)(1H).

6-[[2-Phenyl-1-(3,4,5-trimethoxyphenyl)-1H-benzimidazol-6-yl]oxy]hexanoic acid methyl ester was obtained by reaction of 6-[4-nitro-3-[(3,4,5-trimethoxyphenyl)amino]phenyl]oxy-hexanoic acid methyl ester according to general operating instructions 1 and subsequent cyclization with triethyl orthobenzoate according to general operating instructions 3.

Flash point 128-130° C.

EXAMPLE 66

6-[[2-Phenyl-1-(3,4,5-trimethoxyphenyl)-1H-benzimidazol-6-yl]oxy]hexanoic acid was obtained by reaction of 6-[[2-phenyl-1-(3,4,5-trimethoxyphenyl)-1H-benzimidazol-6-yl]oxy]hexanoic acid methyl ester according to general operating instructions 9.

Flash point 198-201° C.

EXAMPLE 67

6-[[2-Phenyl-1-(3,4,5-trimethoxyphenyl)-1H-benzimidazol-6-yl]oxy]hexanoic acid isopropyl ester was obtained by reaction of 6-[[2-phenyl-1-(3,4,5-trimethoxyphenyl)-1H-benzimidazol-6-yl]oxy]hexanoic acid with isopropanol according to general operating instructions 10.

Flash point 98-101° C.

EXAMPLE 68

6-[[1-[4-(N,N-Dimethylamino)phenyl]-2-phenyl-1H-benzimidazol-6-yl]oxy]hexanoic acid methyl ester a) N,N-Dimethyl-N'-(5-chloro-2-nitrophenyl)benzene-1,4-diamine was produced analogously to 5-chloro-2-nitrophenyl-m-tolylamine from 1-chloro-3,4-dinitrobenzene and N,N-dimethyl-p-phenylenediamine.

$^1$H-NMR (CDCl$_3$): δ=3.01 ppm s (6H); 6.63 dd (J=10, 2 Hz, 1H); 6.80 d (broad)(J=10 Hz, 2H); 6.97 d (J=2 Hz, 1H); 7.14 d (J=10 Hz, 2H); 8.14 d (J=10 Hz, 1H); 9.42 s (broad)(1H).

b) N,N-Dimethyl-N'-(5-methoxy-2-nitrophenyl)benzene-1,4-diamine 24.9 g of N,N-dimethyl-N'-(5-chloro-2-nitrophenyl)benzene-1,4-diamine was added to a solution that consists of 8 g of sodium in 200 ml of methanol, and the mixture was heated in an autoclave for 9 hours to 120° C. After cooling, crystalline product was suctioned out.

$^1$H-NMR (CDCl$_3$): δ=3.00 ppm s (6H); 3.70 s (3H); 6.25 dd (J=10, 2 Hz, 1H); 6.34 d (J=2 Hz, 1H); 6.78 d (J=10 Hz, 2H); 7.14 d (J=10 Hz, 2H); 8.16 d (J=10 Hz, 1H); 9.67 s (broad)(1H).

c) 6-Methoxy-1-[4-(N,N-dimethylamino)phenyl]-2-phenyl-1H-benzimidazole was produced by reaction of N,N-dimethyl-N'-(5-methoxy-2-nitrophenyl)benzene-1,4-diamine according to general operating instructions 1, subsequent reaction of the crude diamine with trimethyl orthobenzoate according to general operating instructions 3 and subsequent refluxing of the crude product with 6N aqueous hydrochloric acid for 1 hour. After the reaction mixture was alkalized with aqueous sodium hydroxide solution, it was extracted with ethyl acetate, dried on sodium sulfate and concentrated by evaporation in a vacuum.

$^1$H-NMR (CDCl$_3$): δ=3.04 ppm s (6H); 3.80 s (3H); 6.68 d (J=2 Hz, 1H); 6.78 d (J=10 Hz, 2H); 6.95 dd (J=10, 2 Hz, 1H); 7.17 d (J=10 Hz, 2H); 7.25-7.33 m (3H); 7.56-7.64 m (2H); 7.74 d (J=10 Hz, 1H).

d) 6-Hydroxy-1-[4-(N,N-dimethylamino)phenyl]-2-phenyl-1H-benzimidazole was obtained by reaction of 6-methoxy-1-[4-(N,N-dimethylamino)phenyl]-2-phenyl-1H-benzimidazole according to general operating instructions 6.

$^1$H-NMR (D$_6$-DMSO): δ=2.98 ppm s (6H); 6.48 d (J=2 Hz, 1H); 6.78 dd (J=10, 2 Hz, 1H); 6.83 d (J=10 Hz, 2H); 7.17 d (J=10 Hz, 2H); 7.30-7.38 m (3H); 7.50-7.57 m (3H); 9.32 s (broad)(1H).

6-[[1-[4-(N,N-Dimethylamino)phenyl]-2-phenyl-1H-benzimidazol-6-yl]oxy]hexanoic acid methyl ester was obtained by reaction of 6-hydroxy-1-[4-(N,N-dimethylamino)phenyl]-2-phenyl-1H-benzimidazole with 6-bromohexanoic acid methyl ester according to general operating instructions 8.

$^1$H-NMR (CDCl$_3$): δ=1.43-1.57 ppm m (2H); 1.64-1.85 m (4H); 2.33 t (J=7.5 Hz, 2H); 3.05 s (6H); 3.67 s (3H); 3.93 t (J=7.5 Hz, 2H); 6.65 d (J=2 Hz, 1H); 6.76 d (J=10 Hz, 2H); 6.93 dd (J=10, 2 Hz, 1H); 7.14 d (J=10 Hz, 2H); 7.23-7.27 m (3H); 7.62 dd (J=10, 1.5 Hz, 2H); 7.74 d (J=10 Hz, 1H).

EXAMPLE 69

6-[[1-[4-(N,N-Dimethylamino)phenyl]-2-phenyl-1H-benzimidazol-6-yl]oxy]hexanoic acid was obtained by reaction of 6-[[1-[4-(N,N-dimethylamino)phenyl]-2-phenyl-1H-benzimidazol-6-yl]oxy]hexanoic acid methyl ester according to general operating instructions 9.

Flash point 210-213° C.

EXAMPLE 70

6-[[1-(4-Biphenyl)-2-phenyl-1H-benzimidazol-6-yl]oxy]hexanoic acid methyl ester a) 5-Chloro-2-nitrophenyl-4-biphenylamine was produced analogously to 5-chloro-2-nitrophenyl-m-tolylamine from 1-chloro-3,4-dinitrobenzene and 4-biphenylamine. It was purified by chromatography on silica-gel.

$^1$H-NMR (CDCl$_3$): δ=6.76 dd (J=10, 2 Hz, 1H); 7.26 d (J=2 Hz, 1H); 7.35 d (J=8 Hz, 1H); 7.32-7.52 m (4H); 7.60-7.72 m (4H); 8.19 d (J=10 Hz, 1H); 9.60 s (broad)(1H).

b) 5-Methoxy-2-nitrophenyl-4-biphenylamine was produced analogously to 5-methoxy-2-nitrophenyl-m-tolylamine from 5-chloro-2-nitrophenyl-4-biphenylamine and sodium methanolate.

Flash point 150-154° C.

b) 1-(4-Biphenyl)-6-methoxy-2-phenyl-1H-benzimidazole was obtained by reaction of 5-methoxy-2-nitrophenyl-4-biphenylamine according to general operating instructions 1 and subsequent cyclization with triethyl orthobenzoate according to general operating instructions 3.

Flash point 140-144° C.

c) 1-(4-Biphenyl)-6-hydroxy-2-phenyl-1H-benzimidazole was obtained by reaction of 1-(4-biphenyl)-6-methoxy-2-phenyl-1H-benzimidazole according to general operating instructions 6.

Flash point 312° C.

6-[[1-(4-Biphenyl)-2-phenyl-1H-benzimidazol-6-yl]oxy]hexanoic acid methyl ester was obtained by reaction of 1-(4-biphenyl)-6-hydroxy-2-phenyl-1H-benzimidazole with 6-bromohexanoic acid methyl ester according to general operating instructions 8.

Flash point 106-108° C.

EXAMPLE 71

6-[[1-(4-Biphenyl)-2-phenyl-1H-benzimidazol-6-yl]oxy]hexanoic acid was obtained by reaction of 6-[[1-(4-biphenyl)-2-phenyl-1H-benzimidazol-6-yl]oxy]hexanoic acid methyl ester according to general operating instructions 9.

$^1$H-NMR (D$_6$-DMSO): δ=1.35-1.78 ppm m (6H); 2.20 t (J=7.5 Hz, 2H); 3.96 m (2H); 6.72 d (J=2 Hz, 1H); 6.97 dd (J=10, 2 Hz, 1H); 7.32-7.58 m (10H); 7.69 d (J=10 Hz, 1H); 7.80 d (J=8 Hz, 2H); 7.89 d (J=10 Hz, 2H).

EXAMPLE 72

6-[[1-(2-Naphthyl)-2-phenyl-1H-benzimidazol-6-yl]oxy]hexanoic acid methyl ester a) 3-(2-Naphthylamino)-4-nitrophenol 3 g of 3-fluoro-4-nitrophenol and 8.2 g of 2-naphthylamine were mixed and stirred for 8 hours at 180° C. The raw mixture was taken up in chloroform and washed with 2N aqueous hydrochloric acid. The organic phase was dried on sodium sulfate and concentrated by evaporation in a vacuum. The residue was chromatographed on silica gel.

$^1$H-NMR (D$_6$-DMSO): δ=6.02 ppm s (2H); 6.25 dd (J=10, 2 Hz, 1H); 6.33 d (J=2 Hz, 1H); 6.72 dd (J=8, 1.5 Hz, 1H); 6.87 d (J=1.5 Hz, 1H); 7.05 d (J=10 Hz, 1H); 8.18 d (J=10 Hz, 1H); 9.52 s (broad)(1H).

b) 6-[3-(2-Naphthyl)amino-4-nitrophenyl]oxyhexanoic acid methyl ester was obtained by reaction of 3-(2-naphthylamino)-4-nitrophenol with 6-bromohexanoic acid methyl ester according to general operating instructions 8.

¹H-NMR (CDCl₃): δ=1.35-1.49 ppm m (2H); 1.60-1.80 m (4H); 2.30 t (J=7.5 Hz, 2H); 3.64 s (3H); 3.84 t (J=7.5 Hz, 2H); 6.35 dd (J=10, 2 Hz, 1H); 6.62 d (J=2 Hz, 1H); 7.43 dd (J=10, 2 Hz, 1H); 7.48-7.57 m (2H); 7.75 d (J=2 Hz, 1H); 7.78-7.90 m (2H); 7.91 d (J=10 Hz, 1H); 8.21 D (J=10 Hz, 1H); 9.92 s (broad)(1H).

6-[[1-(2-Naphthyl)-2-phenyl-1H-benzimidazol-6-yl]oxy]hexanoic acid methyl ester was obtained by reaction of 6-[1-(2-naphthylamino)-4-nitrophenyl]oxyhexanoic acid methyl ester according to general operating instructions 1 and subsequent cyclization with triethyl orthobenzoate according to general operating instructions 3.

Flash point 111-114° C.

EXAMPLE 73

6-[[1-(2-Naphthyl)-2-phenyl-1H-benzimidazol-6-yl]oxy]hexanoic acid was obtained by reaction of 6-[[1-(2-naphthyl)-2-phenyl-1H-benzimidazol-6-yl]oxy]hexanoic acid methyl ester according to general operating instructions 9.

Flash point 170-175° C.

EXAMPLE 74

6-[[1-(2-Fluorenyl)-2-phenyl-1H-benzimidazol-6-yl]oxy]hexanoic acid methyl ester a) 3-(2-Fluorenylamino)-4-nitrophenol 2.17 g of 3-fluoro-4-nitrophenol and 5 g of 2-aminofluorene were mixed and stirred for 9 hours at 140° C. The raw mixture was taken up in ethyl acetate and water and washed with 1N aqueous hydrochloric acid. The aqueous phase was extracted with ethyl acetate, and the combined organic phases were washed three times with 2N aqueous hydrochloric acid and once with saturated sodium chloride solution, dried on sodium sulfate and concentrated by evaporation in a vacuum. The residue was chromatographed on silica gel.

¹H-NMR (D₆-DMSO): δ=3.96 ppm s (2H); 6.30 dd (J=10, 2 Hz, 1H); 6.52 d (J=2 Hz, 1H); 7.28-7.45 m (3H); 7.57 s (broad)(1H); 7.60 d (J=8 Hz, 1H); 7.92 d (J=8 Hz, 1H); 7.98 d (J=8 HZ, 1H); 8.10 d (J=10 Hz, 1H); 9.70 s (1H); 10.80 s (broad)(1H).

b) 6-[3-(2-Fluorenylamino)-4-nitrophenyl]oxyhexanoic acid methyl ester was obtained by reaction of 3-(2-fluorenylamino)-4-nitrophenol with 6-bromohexanonic acid methyl ester according to general operating instructions 8.

¹H-NMR (CDCl₃): δ=1.38-1.50 ppm m (2H); 1.58-1.80 m (4H); 2.30 t (J=7.5 Hz, 2H); 3.65 s (3H); 3.84 t (J=7.5 Hz, 2H); 3.95 s (2H); 6.31 dd (J=10, 2 Hz, 1H); 6.53 d (J=2 Hz, 1H); 7.33 t (J=8 Hz, 2H); 7.42 t (J=8 Hz, 1H); 7.47 s (1H); 7.58 d (J=8 Hz, 1H); 7.80 d (J=8 Hz, 1H); 7.83 d (J=8 Hz, 1H); 8.21 d (J=10 Hz, 1H); 9.87 s (broad)(1H).

6-[[1-(2-Fluorenyl)-2-phenyl-1H-benzimidazol-6-yl]oxy]hexanoic acid methyl ester was obtained by reaction of 6-[3-(2-fluorenyl)amino)-4-nitrophenyl]oxyhexanoic acid methyl ester according to general operating instructions 1 and subsequent cyclization with triethyl orthobenzoate according to general operating instructions 3.

Flash point 125-128° C.

EXAMPLE 75

6-[[1-Phenyl-2-[3-(trifluoromethyl)phenyl]-1H-benzimidazol-6-yl]oxy]hexanoic acid methyl ester a) Ethyl-(3-trifluoromethyl)benzimidate hydrochloride 9.7 ml of 3-(trifluoromethyl)benzonitrile was dissolved in 12 ml of ethanol, and the solution was saturated with HCl gas while being cooled in an ice bath. After 72 hours, precipitated product was suctioned out. The product was washed with diethyl ether.

Flash point 131-133° C. (decomposition)

b) 5-Methoxy-2-nitrophenyldiphenylamine

A solution of 2 g of 3-fluoro-4-nitroanisole in 16 ml of aniline was stirred for 24 hours at 140° C. After cooling, it was taken up in ethyl acetate and extracted with 2N aqueous hydrochloric acid. The organic phase was dried on sodium sulfate and concentrated by evaporation in a vacuum. The residue was chromatographed on silica gel.

¹H-NMR (CDCl₃): δ=3.72 ppm s (3H); 6.36 dd (J=10, 2 Hz, 1H); 6.57 d (J=2 Hz, 1H); 7.22-7.33 m (3H); 7.44 dd (J=8, 8 Hz, 2H); 8.18 d (J=10 Hz, 1H); 9.78 s (broad)(1H).

c) 4-Methoxy-N²-phenyl-o-phenylenediamine was obtained by reaction of 5-methoxy-2-nitrophenyldiphenylamine according to general operating instructions 1.

¹H-NMR (CDCl₃): δ=3.42 ppm s (broad)(2H); 3.72 s (3H); 5.33 s (broad)(1H); 6.56 dd (J=10, 2 Hz, 1H); 6.76 d (J=10 Hz, 1H); 6.79 d (J=2 Hz, 1H); 6.82-6.90 m (3H); 7.25 dd (J=8, 8 Hz, 2H)

d) 6-Methoxy-1-phenyl-2-[3-(trifluoromethyl)phenyl]-1H-benzimidazole was obtained by reaction of 4-methoxy-N²-phenyl-o-phenylenediamine with ethyl-(3-trifluoromethyl)benzimidate hydrochloride according to general operating instructions 4.

Flash point 138-140° C.

e) 6-Hydroxy-1-phenyl-2-[3-(trifluoromethyl)phenyl]-1H-benzimidazole was obtained by reaction of 6-methoxy-1-phenyl-2-[3-(trifluoromethyl)phenyl]-1H-benzimidazole according to general operating instructions 7.

¹H-NMR (D₆-DMSO): δ=6.60 ppm d (J=2 Hz, 1H); 6.99 dd (J=10, 2 Hz, 1H); 7.50-7.89 m (10H).

6-[[1-Phenyl-2-[3-(trifluoromethyl)phenyl]-1H-benzimidazol-6-yl]oxy]hexanoic acid methyl ester was obtained by reaction of 6-hydroxy-1-phenyl-2-[3-(trifluoromethyl)phenyl]-1H-benzimidazole with 6-bromohexanoic acid methyl ester according to general operating instructions 8.

Flash point 68-70° C.

EXAMPLE 76

6-[[1-Phenyl-2-[3-(trifluoromethyl)phenyl]-1H-benzimidazol-6-yl]oxy]hexanoic acid isopropyl ester was obtained by reaction of 6-hydroxy-1-phenyl-2-[3-(trifluoromethyl)phenyl]-1H-benzimidazole with 6-bromohexanoic acid isopropyl ester according to general operating instructions 8.

Flash point 96-98° C.

EXAMPLE 77

6-[[1-Phenyl-2-[3-(trifluoromethyl)phenyl]-1H-benzimidazol-6-yl]oxy]hexanoic acid was obtained by reaction of 6-[[1-phenyl-2-[3-(trifluoromethyl)phenyl]-1H-benzimidazol-6-yl]oxy]hexanoic acid methyl ester according to general operating instructions 9.

$^1$H-NMR (D$_6$-DMSO): δ=1.38-1.80 ppm m (6H); 2.27 t (J=7.5 Hz, 2H); 3.98 t (J=7.5 Hz, 2H); 6.70 d (J=2 Hz, 1H); 7.02 dd (J=10, 2 Hz, 1H); 7.48-7.88 m (9H); 7.77 d (J=10 Hz, 1H); 11.94 s (broad)(1H).

EXAMPLE 78

6-[[1-Phenyl-2-[3-(trifluoromethyl)phenyl]-1H-benzimidazol-6-yl]oxy]hexan-1-ol was obtained by reaction of 6-[[1-phenyl-2-[3-(trifluoromethyl)phenyl]-1H-benzimidazol-6-yl]oxy]hexanoic acid methyl ester according to general operating instructions 11.

$^1$H-NMR (CDCl$_3$): δ=1.38-1.68 ppm m (6H); 1.75-1.87 m (2H); 3.60-3.72 m (2H); 3.94 t (J=7.5 Hz, 2H); 6.69 d (J=2 Hz, 1H); 6.99 dd (J=10, 2 Hz, 1H); 7.25-7.35 m (2H); 7.40 dd (J=8.8 Hz; 1H); 7.50-7.61 m (4H); 7.68 d (broad)(J=8 Hz, 1H); 7.78 d (J=10 Hz, 1H); 7.83 s (broad)(1H).

EXAMPLE 79

6-[[2-(3-Chlorophenyl)-1-phenyl-1H-benzimidazol-6-yl]oxy]hexanoic acid methyl ester a) 2-(3-Chlorophenyl)-6-methoxy-1-phenyl-1H-benzimidazole was obtained by reaction of 4-methoxy-N$^2$-phenyl-o-phenylenediamine with ethyl-3-chlorobenzimidate hydrochloride (produced according to: DeWolfe and Augustine; J. Org. Chem.; 30; 699) according to general operating instructions 4.

Flash point 149-151° C.

b) 2-(3-Chlorophenyl)-6-hydroxy-1-phenyl-1H-benzimidazole was obtained by reaction of 2-(3-chlorophenyl)-6-methoxy-1-phenyl-1H-benzimidazole according to general operating instructions 7.

Flash point 199-202° C.

6-[[2-(3-Chlorophenyl)-1-phenyl-1H-benzimidazol-6-yl]oxy]hexanoic acid methyl ester was obtained by reaction of 2-(3-chlorophenyl)-6-hydroxy-1-phenyl-1H-benzimidazole with 6-bromohexanoic acid methyl ester according to general operating instructions 8.

Flash point 69-72° C.

EXAMPLE 80

6-[[2-(3-Chlorophenyl)-1-phenyl-1H-benzimidazol-6-yl]oxy]hexanoic acid isopropyl ester was obtained by reaction of 2-(3-chlorophenyl)-6-hydroxy-1-phenyl-1H-benzimidazole with 6-bromohexanoic acid isopropyl ester according to general operating instructions 8.

Flash point 98-100° C.

EXAMPLE 81

6-[[2-(3-Chlorophenyl)-1-phenyl-1H-benzimidazol-6-yl]oxy]hexanoic acid was obtained by reaction of 6-[[2-(3-chlorophenyl)-1-phenyl-1H-benzimidazol-6-yl]oxy]hexanoic acid methyl ester according to general operating instructions 9.

Flash point 137-140° C.

EXAMPLE 82

6-[[2-(3-Chlorophenyl)-1-phenyl-1H-benzimidazol-6-yl]oxy]hexan-1-ol was obtained by reaction of 6-[[2-(3-chlorophenyl)-1-phenyl-1H-benzimidazol-6-yl]oxy]hexanoic acid methyl ester according to general operating instructions 11.

$^1$H-NMR (CDCl$_3$): δ=1.40-1.70 ppm m (6H); 1.75-1.86 m (2H); 3.67 t (J=7.5 Hz, 2H); 3.93 t (J=7.5 Hz, 2H); 6.69 d (J=2 Hz, 1H); 6.99 dd (J=10, 2 Hz, 1H); 7.20 dd (J=8.8 Hz,; 1H); 7.26-7.38 m (4H); 7.47-7.58 m (3H); 7.60 dd (J=2, 2 Hz, 1H); 7.76 d (J=10 Hz, 1H).

EXAMPLE 83

6-[[2-(4-Chlorophenyl)-1-phenyl-1H-benzimidazol-6-yl]oxy]hexanoic acid methyl ester a) Ethyl-4-chlorobenzimidate hydrochloride 10 g of 4-chlorobenzonitrile was suspended in 12 ml of ethanol and dissolved by adding diethyl ether. While being cooled in an ice bath, it was saturated with HCl gas. After 72 hours, precipitated product was suctioned out. The product was washed with diethyl ether.

Flash point 173-174° C. (decomposition)

a) 2-(4-Chlorophenyl)-6-methoxy-1-phenyl-1H-benzimidazole was obtained by reaction of 4-methoxy-$N^2$-phenyl-o-phenylenediamine with ethyl-4-chlorobenzimidate hydrochloride according to general operating instructions 4.

Flash point 162-164° C.

b) 2-(4-Chlorophenyl)-6-hydroxy-1-phenyl-1H-benzimidazole was obtained by reaction of 2-(4-chlorophenyl)-6-methoxy-1-phenyl-1H-benzimidazole according to general operating instructions 7.

Flash point 246-250° C.

6-[[2-(4-Chlorophenyl)-1-phenyl-1H-benzimidazol-6-yl]oxy]hexanoic acid methyl ester was obtained by reaction of 2-(4-chlorophenyl)-6-hydroxy-1-phenyl-1H-benzimidazole with 6-bromohexanoic acid methyl ester according to general operating instructions 8.

Flash point 86-87° C.

EXAMPLE 84

6-[[2-(4-Chlorophenyl)-1-phenyl-1H-benzimidazol-6-yl]oxy]hexanoic acid isopropyl ester was obtained by reaction of 2-(4-chlorophenyl)-6-hydroxy-1-phenyl-1H-benzimidazole with 6-bromohexanoic acid isopropyl ester according to general operating instructions 8.

Flash point 124-126° C.

EXAMPLE 85

6-[[2-(4-Chlorophenyl)-1-phenyl-1H-benzimidazol-6-yl]oxy]hexanoic acid was obtained by reaction of 6-[[2-(4-chlorophenyl)-1-phenyl-1H-benzimidazol-6-yl]oxy]hexanoic acid methyl ester according to general operating instructions 9.

$^1$H-NMR (D$_6$-DMSO): δ=1.35-1.48 ppm m (2H); 1.50-1.62 m (2H); 1.64-1.77 m (2H); 2.23 t (J=7.5 Hz, 2H); 3.91 t (J=7.5 Hz, 2H); 6.64 d (J=2 Hz, 1H); 6.96 dd (J=10, 2 Hz, 1H); 7.38-7.50 m (6H); 7.52-7.65 m (3H); 7.70 d (J=10 Hz, 1H).

EXAMPLE 86

6-[[2-(4-Chlorophenyl)-1-phenyl-1H-benzimidazol-6-yl]oxy]hexan-1-ol was obtained by reaction of 6-[[2-(4-chlorophenyl)-1-phenyl-1H-benzimidazol-6-yl]oxy]hexanoic acid methyl ester according to general operating instructions 11.

$^1$H-NMR (CDCl$_3$): δ=1.38-1.68 ppm m (6H); 1.74-1.85 m (2H); 3.67 t (broad)(J=7.5 Hz, 2H); 3.94 t (J=7.5 Hz, 2H); 6.68 d (J=2 Hz, 1H); 6.98 dd (J=10, 2 Hz, 1H); 7.22-7.35 m (5H); 7.47 d (J=8 Hz; 2H); 7.49-7.59 m (2H); 7.73 d (J=10 Hz, 1H).

EXAMPLE 87

6-[[2-(3-Methylphenyl)-1-phenyl-1H-benzimidazol-6-yl]oxy]hexanoic acid methyl ester a) 6-Methoxy-2-(3-methylphenyl)-1-phenyl-1H-benzimidazole was obtained by reaction of 4-methoxy-$N^2$-phenyl-o-phenylenediamine with ethyl-3-methylbenzimidate hydrochloride (produced according to: DeWolfe and Augustine; J. Org. Chem.; 30; 699) according to general operating instructions 4.

Flash point 156-158° C.

b) 6-Hydroxy-2-(3-methylphenyl)-1-phenyl-1H-benzimidazole was obtained by reaction of 6-methoxy-2-(3-methylphenyl)-1-phenyl-1H-benzimidazole according to general operating instructions 7.

$^1$H-NMR (D$_6$-DMSO): δ=2.23 ppm s (3H); 6.52 d (J=2 Hz, 1H); 6.80 dd (J=10, 2 Hz, 1H); 7.18 s (broad)(3H); 7.35-7.52 m (3H); 7.50-7:63 m (4H); 9.28 s (broad)(1H).

6-[[2-(3-Methylphenyl)-1-phenyl-1H-benzimidazol-6-yl]oxy]hexanoic acid methyl ester was obtained by reaction of 6-hydroxy-2-(3-methylphenyl)-1-phenyl-1H-benzimidazole with 6-bromohexanoic acid methyl ester according to general operating instructions 8.

Flash point 82-84° C.

EXAMPLE 88

6-[[2-(3-Methylphenyl)-1-phenyl-1H-benzimidazol-6-yl]oxy]hexanoic acid isopropyl ester was obtained by reaction of 6-hydroxy-2-(3-methylphenyl)-1-phenyl-1H-benzimidazole with 6-bromohexanoic acid isopropyl ester according to general operating instructions 8.

$^1$H-NMR (CDCl$_3$): δ=1.22 ppm d (J=7.5 Hz, 6H); 1.38-1.56 m (2H); 1.62-1.85 m (4H); 2.30 t (J=7.5 Hz, 2H); 2.30 s (3H); 3.93 t (J=7.5 Hz, 2H); 5.00 sp (J=7.5 Hz, 1H); 6.68 d (J=2 Hz, 1H); 6.95 dd (J=10, 2 Hz, 1H); 7.13 s (broad) (3H); 7.31 dd (J=8, 2 Hz, 2H); 7.42-7.57 m (4H); 7.76 d (J=10 Hz, 1H).

EXAMPLE 89

6-[[2-(3-Methylphenyl)-1-phenyl-1H-benzimidazol-6-yl]oxy]hexanoic acid was obtained by reaction of 6-[[2-(3-methylphenyl)-1-phenyl-1H-benzimidazol-6-yl]oxy]hexanoic acid methyl ester according to general operating instructions 9.

$^1$H-NMR (D$_6$-DMSO): δ=1.35-1.49 ppm m (2H); 1.50-1.63 m (2H); 1.64-1.78 m (2H); 2.22 t (J=7.5 Hz, 2H); 2.24 s (3H); 3.92 t (J=7.5 Hz, 2H); 6.62 d (J=2 Hz, 1H); 6.95 dd (J=10, 2 Hz, 1H); 7.18 s (broad)(3H); 7.37-7.42 m (3H); 7.51-7.65 m (3H); 7.67 d (J=10 Hz, 1H); 11.90 s (broad) (1H).

EXAMPLE 90

6-[[2-(3-Methylphenyl)-1-phenyl-1H-benzimidazol-6-yl]oxy]hexan-1-ol was obtained by reaction of 6-[[2-(3-methylphenyl)-1-phenyl-1H-benzimidazol-6-yl]oxy]hexanoic acid methyl ester according to general operating instructions 9.
Flash point 92-94° C.

EXAMPLE 91

6-[[2-(4-Methylphenyl)-1-phenyl-1H-benzimidazol-6-yl]oxy]hexanoic acid methyl ester a) 6-Methoxy-2-(4-methylphenyl)-1-phenyl-1H-benzimidazole was obtained by reaction of 4-methoxy-$N^2$-phenyl-o-phenylenediamine with ethyl-4-methylbenzimidate hydrochloride (produced according to: DeWolfe and Augustine; J. Org. Chem.; 30; 699) according to general operating instructions 4.
Flash point 150-152° C.

b) 6-Hydroxy-2-(4-methylphenyl)-1-phenyl-1H-benzimidazole was obtained by reaction of 6-methoxy-2-(4-methylphenyl)-1-phenyl-1H-benzimidazole according to general operating instructions 7.
Flash point 257-264° C.

6-[[2-(4-Methylphenyl)-1-phenyl-1H-benzimidazol-6-yl]oxy]hexanoic acid methyl ester was obtained by reaction of 6-hydroxy-2-(4-methylphenyl)-1-phenyl-1H-benzimidazole with 6-bromohexanoic acid methyl ester according to general operating instructions 8.
Flash point 99-102° C.

EXAMPLE 92

6-[[2-(4-Methylphenyl)-1-phenyl-1H-benzimidazol-6-yl]oxy]hexanoic acid isopropyl ester was obtained by reaction of 6-hydroxy-2-(4-methylphenyl)-1-phenyl-1H-benzimidazole with 6-bromohexanoic acid isopropyl ester according to general operating instructions 8.
Flash point 107-109° C.

EXAMPLE 93

6-[[2-(4-Methylphenyl)-1-phenyl-1H-benzimidazol-6-yl]oxy]hexanoic acid was obtained by reaction of 6-[[2-(4-methylphenyl)-1-phenyl-1H-benzimidazol-6-yl]oxy]hexanoic acid methyl ester according to general operating instructions 9.
$^1$H-NMR ($D_6$-DMSO): δ=1.33-1.49 ppm m (2H); 1.50-1.62 m (2H); 1.64-1.77 m (2H); 2.22 t (J=7.5 Hz, 2H); 2.30 s (3H); 3.90 t (J=7.5 Hz, 2H); 6.62 d (J=2 Hz, 1H); 6.94 dd (J=10, 2 Hz, 1H); 7.15 d (J=8 Hz, 2H); 7.36 d (J=8 Hz, 2H); 7.40 dd (J=8, 1.5 Hz, 2H); 7.52-7.62 m (3H); 7.68 d (J=10 Hz, 1H).

EXAMPLE 94

6-[[2-(4-Methylphenyl)-1-phenyl-1H-benzimidazol-6-yl]oxy]hexan-1-ol was obtained by reaction of 6-[[2-(4-methylphenyl)-1-phenyl-1H-benzimidazol-6-yl]oxy]hexanoic acid methyl ester according to general operating instructions 11.
Flash point 150-152° C.

EXAMPLE 95

6-[[1-Phenyl-2-(4-pyridinyl)-1H-benzimidazol-6-yl]oxy]hexanoic acid methyl ester a) 6-Methoxy-1-phenyl-2-(4-pyridinyl)-1H-benzimidazole 0.4 g of 4-methoxy-$N^2$-phenyl-o-phenylenediamine was dissolved in 8 ml of N,N-dimethylformamide, and the solution was mixed with 0.7 g of ethyl-2-ethoxy-1,2-dihydroquinoline-1-carboxylate and 0.34 g of isonicotinic acid. It was stirred for 16 hours at 100° C., mixed with water after cooling, extracted three times with ethyl acetate, the combined organic phases were washed with saturated sodium chloride solution, dried on sodium sulfate and concentrated by evaporation in a vacuum. After chromatographic purification on silica gel, the amide was taken up in 5 ml of 6N aqueous hydrochloric acid and refluxed for 3 hours. After cooling, it was stirred in saturated sodium bicarbonate solution, extracted three times with ethyl acetate, the combined extracts were washed with saturated sodium chloride solution, dried on sodium sulfate and concentrated by evaporation in a vacuum.
$^1$H-NMR (CDCl$_3$): δ=3.80 ppm s (3H); 6.66 ppm d (J=2 Hz, 1H); 7.02 dd (J=10, 2 Hz, 1H); 7.32-7.38 m (2H); 7.42 dd (J=8, 1.5 Hz, 2H); 7.54-7.62 m (3H); 7.79 d (J=10 Hz, 1H); 8.53 d (broad)(J=6 Hz, 2H)

b) 6-Hydroxy-1-phenyl-2-(4-pyridinyl)-1H-benzimidazole was produced by reaction of 6-methoxy-1-phenyl-2-(4-pyridinyl)-1H-benzimidazole according to general operating instructions 7.
$^1$H-NMR (CD$_3$OD): δ=6.52 ppm d (J=2 Hz, 1H); 6.82 dd (J=10, 2 Hz, 1H); 7.28-7.33 m (2H); 7.39 dd (J=8, 1.5 Hz, 2H); 7.49-7.57 m (4H); 8.40 d (broad)(J=6 Hz, 2H).

6-[[1-Phenyl-2-(4-pyridinyl)-1H-benzimidazol-6-yl]oxy]hexanoic acid methyl ester was produced by reaction of 6-hydroxy-1-phenyl-2-(4-pyridinyl)-1H-benzimidazole according to general operating instructions 8.
Flash point 100-103° C.

EXAMPLE 96

6-[[1-Phenyl-2-(4-pyridinyl)-1H-benzimidazol-6-yl]oxy]hexanoic acid was produced by reaction of 6-[[1-phenyl-2-(4-pyridinyl)-1H-benzimidazol-6-yl]oxy]hexanoic acid methyl ester according to general operating instructions 9.
Flash point 160-162° C.

EXAMPLE 97

6-[(1,2-Diphenyl-5-nitro-1H-benzimidazol-6-yl)oxy] hexanoic acid methyl ester a) 1,2-Diphenyl-6-hydroxy-5-nitro-1H-benzimidazole
b) 1,2-Diphenyl-6-hydroxy-7-nitro-1H-benzimidazole
c) 1,2-Diphenyl-6-hydroxy-5,7-dinitro-1H-benzimidazole 5 g of 1,2-diphenyl-6-hydroxy-1H-benzimidazole was dissolved in 45 ml of glacial acetic acid and mixed at 10-15° C. drop by drop with a solution that consists of 1.67 g of potassium-nitrite in 15 ml of water. It is allowed to stir for 2 hours in an ice bath and then for 2 hours at 20° C., the reaction mixture is concentrated by evaporation in a vacuum and purified by chromatography on silica gel.

a) $^1$H-NMR (CDCl$_3$): δ=6.83 ppm s (1H); 7.25-7.44 m (5H); 7.52-7.60 m (5H); 8.66 S (1H); 10.78 s (1H).
b) $^1$H-NMR (D$_6$-DMSO): δ=7.05 ppm d (J=10 Hz, 1H); 7.30-7.53 m (10H); 7.82 d (J=10 Hz, 1H); 10.83 s (1H).
c) $^1$H-NMR (D$_6$-DMSO): δ=7.32-7.58 ppm m (10H); 8.67 s (1H).

6-[(1,2-Diphenyl-5-nitro-1H-benzimidazol-6-yl)oxy] hexanoic acid methyl ester was obtained by reaction of 1,2-diphenyl-6-hydroxy-5-nitro-1H-benzimidazole with 6-bromohexanoic acid methyl ester according to general operating instructions 8.

Flash point 123° C.

EXAMPLE 98

6-[(1,2-Diphenyl-5-nitro-1H-benzimidazol-6-yl)oxy] hexanoic acid isopropyl ester was obtained by reaction of 1,2-diphenyl-6-hydroxy-5-nitro-1H-benzimidazole with 6-bromohexanoic acid isopropyl ester according to general operating instructions 8.

Flash point 115-117° C.

EXAMPLE 99

6-[(1,2-Diphenyl-7-nitro-1H-benzimidazol-6-yl)oxy] hexanoic acid methyl ester was obtained by reaction of 1,2-diphenyl-6-hydroxy-7-nitro-1H-benzimidazole with 6-bromohexanoic acid methyl ester according to general operating instructions 8.

Flash point 110-112° C.

EXAMPLE 100

6-[(1,2-Diphenyl-7-nitro-1H-benzimidazol-6-yl)oxy] hexanoic acid isopropyl ester was obtained by reaction of 1,2-diphenyl-6-hydroxy-5-nitro-1H-benzimidazole with 6-bromohexanoic acid isopropyl ester according to general operating instructions 8.

Flash point 88° C.

EXAMPLE 101

6-[(7-Amino-1,2-diphenyl-1H-benzimidazol-6-yl)oxy]hexanoic acid methyl ester 340 mg of 6-[(1,2-diphenyl-7-nitro-1H-benzimidazol-6-yl)oxy]hexanoic acid methyl ester was hydrogenated in ethanol with Raney nickel in an autoclave at 50° C. and at normal pressure. After hydrogen absorption ended, catalyst was filtered out and concentrated by evaporation in a vacuum.

Flash point 113-115° C.

EXAMPLE 102

6-[(7-Amino-1,2-diphenyl-1H-benzimidazol-6-yl)oxy]hexanoic acid isopropyl ester was obtained analogously to the instructions indicated in Example 101 by reaction of 6-[(1,2-diphenyl-7-nitro-1H-benzimidazol-6-yl)oxy]hexanoic acid isopropyl ester.

$^1$H-NMR (CDCl$_3$): δ=1.22 ppm d (J=7.5 Hz, 6H); 1.43-1.88 m (6H); 2.30 t (J=7.5 Hz, 2H); 4.04 t (J=7.5 Hz, 2H); 5.00 sp (J=7.5 Hz, 1H); 6.97 d (J=7.5 Hz, 1H); 7.20-7.33 m (4H); 7.42-7.53 m (7H).

EXAMPLE 103

6-[(5,7-Dinitro-1,2-diphenyl-1H-benzimidazol-6-yl)oxy]hexanoic acid methyl ester was obtained by reaction of 5,7-dinitro-1,2-diphenyl-6-hydroxy-1H-benzimidazole with 6-bromohexanoic acid methyl ester according to general operating instructions 8.

Flash point 88-91° C.

EXAMPLE 104

6-[(5,7-Dinitro-1,2-diphenyl-1H-benzimidazol-6-yl)oxy]hexanoic acid isopropyl ester was obtained by reaction of 5,7-dinitro-1,2-diphenyl-6-hydroxy-1H-benzimidazole with 6-bromohexanoic acid isopropyl ester according to general operating instructions 8.

Flash point 92-93° C.

EXAMPLE 105

6-[[5-(Acetylamino)-1,2-diphenyl-1H-benzimidazol-6-yl]oxy]hexanoic acid methyl ester a) 5-Fluoro-2,4-dinitrophenol 0.41 g of 1,3-difluoro-4,6-dinitrobenzene was dissolved in 8 ml of 0.5 N aqueous sodium hydroxide solution and refluxed for 2 hours. After cooling, it was diluted with water and extracted three times with diethyl ether. The aqueous phase was made acidic by adding 1N hydrochloric acid and extracted with diethyl ether. The organic phase was dried on sodium sulfate and concentrated by evaporation in a vacuum.

$^1$H-NMR (CDCl$_3$): δ=7.10 ppm d (J=12 Hz, 1H); 9.03 d (J=8 Hz, 1H); 11.10 s (1H).

b) 2,4-Dinitro-5-hydroxydiphenylamine

100 µl of aniline was added to the suspension that consists of 50 mg of 5-fluoro-2,4-dinitrophenol in 0.5 ml of ethanol, it was stirred for 30 minutes and then allowed to stand for 15 hours. It was suctioned off, the solid was washed with 1N aqueous hydrochloric acid and dried in a vacuum.

$^1$H-NMR (CDCl$_3$): δ=6.58 ppm s (1H); 7.31 d (J=10 Hz, 2H); 7.39 dd (J=10, 10 Hz, 1H); 7.51 dd (J=10, 10 Hz, 2H); 9.20 s (1H); 9.90 s (broad)(1H); 10.97 s (broad)(1H).

c) Acetic acid-(2,4-dinitro-5-phenylamino)phenyl ester 0.11 ml of acetic acid anhydride was added to 275 mg of 2,4-dinitro-5-hydroxydiphenylamine in 1 ml of pyridine, and it was allowed to stir for 30 minutes in an ice bath and then for 1 more hour at 20° C. After dilution with ethyl acetate, it was washed three times with ice-cold 1N aqueous hydrochloric acid, once with saturated potassium bicarbonate solution and once with saturated sodium chloride solution, dried on sodium sulfate and concentrated by evaporation in a vacuum.

$^1$H-NMR (CDCl$_3$): δ=2.34 ppm s (3H); 6.80 s (1H); 7.32 d (J=10 Hz, 2H); 7.40 dd (J=10, 10 Hz, 1H); 7.52 dd (J=10, 10 Hz, 2H); 9.21 s (1H); 9.95 s (broad)(1H).

d) Acetic acid-(1,2-diphenyl-6-hydroxy-1H-benzimidazol-5-yl)amide was obtained by reaction of acetic acid-(2,4-dinitro-5-phenylamino)phenyl ester according to general operating instructions 1 and subsequent reaction with trimethyl orthobenzoate according to general operating instructions 3.

$^1$H-NMR (CDCl$_3$): δ=2.26 ppm s (3H); 6.88 s (1H); 7.22-7.36 m (5H); 7.42-7.53 m (5H); 7.61 s (1H); 8.43 s (broad)(1H).

6-[[5-(Acetylamino)-1,2-diphenyl-1H-benzimidazol-6-yl]oxy]hexanoic acid methyl ester was obtained by reaction of acetic acid-(1,2-diphenyl-6-hydroxy-1H-benzimidazol-5-yl)amide with 6-bromohexanoic acid methyl ester according to general operating instructions 8.

Flash point 128-130° C.

EXAMPLE 106

6-[(5-Amino-1,2-diphenyl-1H-benzimidazol-6-yl)oxy]hexanoic acid isopropyl ester was obtained by reaction of 6-[(1,2-diphenyl-5-nitro-1H-benzimidazol-6-yl)oxy]hexanoic acid isopropyl ester according to general operating instructions 1.

$^1$H-NMR (CDCl$_3$): δ=1.23 ppm d (J=7.5 Hz, 6H); 1.47-1.90 m (6H); 2.32 t (J=7.5 Hz, 2H); 3.95 t (J=7.5 Hz, 2H); 5.02 sp (J=7.5 Hz, 1H); 6.60 s (1H); 7.20 s (1H); 7.22-7.33 m (5H); 7.43-7.58 m (5H).

EXAMPLE 107

6-[[5-[[(4-Bromophenyl)sulfonyl]amino]-1,2-diphenyl-1H-benzimidazol-6-yl]oxy]hexanoic acid isopropyl ester 6-[(5-Amino-1,2-diphenyl-1H-benzimidazol-6-yl)oxy] hexanoic acid isopropyl ester was reacted according to general operating instructions 13 with 4-bromobenzenesulfonic acid chloride.

Flash point 173-175° C.

EXAMPLE 108

6-[(5-Amino-1,2-diphenyl-1H-benzimidazol-6-yl)oxy]hexanoic acid methyl ester was obtained by reaction of 6-[(1,2-diphenyl-5-nitro-1H-benzimidazol-6-yl)oxy]hexanoic acid methyl ester according to general operating instructions 1.

$^1$H-NMR (CDCl$_3$): δ=1.48-1.88 ppm (6H); 2.36 t (J=7.5 Hz, 2H, CH$_2$=CO); 3.67 s (3H); 3.94 t (J=7.5 Hz, 2H); 6.60 s (1H); 7.21 s (1H); 7.22-7.35 m (5H); 7.43-7.59 m (5H).

EXAMPLE 109

6-[[5-[[(4-Chlorophenyl)sulfonyl]amino]-1,2-diphenyl-1H-benzimidazol-6-yl]oxy]hexanoic acid methyl ester 6-[(5-Amino-1,2-diphenyl-1H-benzimidazol-6-yl)oxy] hexanoic acid methyl ester was reacted according to general operating instructions 13 with 4-chlorobenzenesulfonic acid chloride.

Flash point 157-159° C.

EXAMPLE 110

6-[[5-[[(4-Chlorophenyl)sulfonyl]amino]-1,2-diphenyl-1H-benzimidazol-6-yl]oxy]hexanoic acid isopropyl ester 6-[(5-Amino-1,2-diphenyl-1H-benzimidazol-6-yl)oxy] hexanoic acid isopropyl ester was reacted according to general operating instructions 13 with 4-chlorobenzenesulfonic acid chloride.

Flash point 158-159° C.

EXAMPLE 111

6-[[5-[[(4-Chlorophenyl)sulfonyl]amino]-1,2-diphenyl-1H-benzimidazol-6-yl]oxy]hexanoic acid was obtained by reaction of 6-[[5-[[(4-chlorophenyl)sulfonyl]amino]-1,2-diphenyl-1H-benzimidazol-6-yl]oxy]hexanoic acid methyl ester according to general operating instructions 9.

Flash point 201-203° C.

EXAMPLE 112

6-[[1,2-Diphenyl-5-[[(3-methylphenyl)sulfonyl] amino]-1H-benzimidazol-6-yl]oxy]-hexanoic acid isopropyl ester 6-[(5-Amino-1,2-diphenyl-1H-benzimidazol-6-yl)oxy] hexanoic acid isopropyl ester was reacted according to general operating instructions 13 with 3-methylbenzenesulfonic acid chloride.

Flash point 149-151° C.

EXAMPLE 113

6-[[1,2-Diphenyl-5-[[(4-methylphenyl)sulfonyl]amino]-1H-benzimidazol-6-yl]oxy]-hexanoic acid isopropyl ester 6-[(5-Amino-1,2-diphenyl-1H-benzimidazol-6-yl)oxy]hexanoic acid isopropyl ester was reacted according to general operating instructions 13 with 4-methylbenzenesulfonic acid chloride.
Flash point 139-141° C.

EXAMPLE 114

6-[[1,2-Diphenyl-5-[[(4-methoxyphenyl)sulfonyl]amino]-1H-benzimidazol-6-yl]oxy]-hexanoic acid isopropyl ester 6-[(5-Amino-1,2-diphenyl-1H-benzimidazol-6-yl)oxy]hexanoic acid isopropyl ester was reacted according to general operating instructions 13 with 4-methoxybenzenesulfonic acid chloride.
$^1$H-NMR (CDCl$_3$): δ=1.25 ppm d (J=7.5 Hz, 6H); 1.35-1:45 m (2H); 1.59-1.73 m (4H); 2.30 t (J=7.5 Hz, 2H); 3.72 t (J=7.5 Hz, 2H); 3.80 s (3H); 5.02 sp (J=7.5 Hz, 1H); 6.50 s (1H); 6.85 d (J=10 Hz, 2H); 6.99 s (1H); 7.25-7.35 m (5H); 7.45-7.52 m (5H); 7.74 d (J=10 Hz, 2H); 7.99 s (1H).

EXAMPLE 115

6-[[1,2-Diphenyl-5-[[[(4-trifluoromethyl)phenyl]sulfonyl]amino]-1H-benzimidazol-6-yl]oxy]hexanoic acid isopropyl ester 6-[(5-Amino-1,2-diphenyl-1H-benzimidazol-6-yl)oxy]hexanoic acid isopropylester was reacted according to general operating instructions 13 with 4-(trifluoromethyl)benzenesulfonic acid chloride.
Flash point 170-171° C.

EXAMPLE 116

6-[[5-[[[4-(Acetylamino)phenyl]sulfonyl]amino]-1,2-diphenyl-1H-benzimidazol-6-yl]oxy]hexanoic acid isopropyl ester 6-[(5-Amino-1,2-diphenyl-1H-benzimidazol-6-yl)oxy]hexanoic acid isopropyl ester was reacted according to general operating instructions 13 with 4-(acetylamino)benzenesulfonic acid chloride.
Flash point 100-102° C.

EXAMPLE 117

6-[[5-[[Bis(3-chlorophenyl)sulfonyl]amino]-1,2-diphenyl-1H-benzimidazol-6-yl]oxy]-hexanoic acid isopropyl ester 6-[(5-Amino-1,2-diphenyl-1H-benzimidazol-6-yl)oxy]hexanoic acid isopropyl ester was reacted according to general operating instructions 13 with 3-chlorobenzenesulfonic acid chloride.
Flash point 163-167° C.

EXAMPLE 118

6-[[1,2-Diphenyl-5-[(propylsulfonyl)amino]-1H-benzimidazol-6-yl]oxy]hexanoic acid isopropyl ester 6-[(5-Amino-1,2-diphenyl-1H-benzimidazol-6-yl)oxy]hexanoic acid isopropyl ester was reacted according to general operating instructions 13 with propanesulfonic acid chloride.
Flash point 126-128° C.

EXAMPLE 119

6-[[5-[(Benzylsulfonyl)amino]-1,2-diphenyl-1H-benzimidazol-6-yl]oxy]hexanoic acid isopropyl ester 6-[(5-Amino-1,2-diphenyl-1H-benzimidazol-6-yl)oxy]hexanoic acid isopropyl ester was reacted with benzenemethanesulfonic acid chloride according to general operating instructions 13.
Flash point 137-138° C.

EXAMPLE 120

4-[(1,2-Diphenyl-1H-benzimidazol-6-yl)oxy]methylbenzoic acid methyl ester was produced by reaction of 1,2-diphenyl-6-hydroxy-1H-benzimidazole with 4-(bromomethyl)-benzoic acid methyl ester according to general operating instructions 8.
Flash point 180-184° C.

EXAMPLE 121

4-[(1,2-Diphenyl-1H-benzimidazol-6-yl)oxy]methylbenzoic acid was produced by reaction of 4-[(1,2-diphenyl-1H-benzimidazol-6-yl)oxy]methylbenzoic acid methyl ester according to general operating instructions 9.
$^1$H-NMR (D$_6$-DMSO): δ=5.12 ppm s (2H); 6.76 d (J=2 Hz, 1H); 7.04 dd (J=10, 2 Hz, 1H); 7.30-7.63 m (12H); 7.70 d (J=10 Hz, 1H); 7.89 d (J=8 Hz, 2H).

EXAMPLE 122

4-[[1-(3-Methylphenyl)-2-phenyl-1H-benzimidazol-6-yl]oxy]methylbenzoic acid methyl ester was produced by reaction of 6-hydroxy-1-(3-methylphenyl)-2-phenyl-1H-benzimidazole with 4-(bromomethyl)benzoic acid methyl ester according to general operating instructions 8.
Flash point 138-142° C.

EXAMPLE 123

4-[[1-(4-Methylphenyl)-2-phenyl-1H-benzimidazol-6-yl]oxy]methylbenzoic acid methyl ester was produced by reaction of 6-hydroxy-1-(4-methylphenyl)-2-phenyl-1H-benzimidazole with 4-(bromomethyl)benzoic acid methyl ester according to general operating instructions 8.
Flash point 145-148° C.

EXAMPLE 124

2-[2-[(1,2-Diphenyl-1H-benzimidazol-6-yl)oxy]ethoxy]acetic acid-tert-butyl ester 0.2 g of [(1,2-diphenyl-1H-benzimidazol-6-yl)oxy]ethan-1-ol was suspended in 1.7 ml of toluene and 0.7 ml of tetrahydrofuran. 0.1 ml of bromoacetic acid-tert-butyl ester, 13 mg of tetrabutylammonium hydrogen sulfate, and 1.45 ml of 32% sodium hydroxide solution were added to it, and it was allowed to stir for 48 hours. Another 0.1 ml of bromoacetic acid-tert-butyl ester and 13 mg of tetrabutylammonium hydrogen sulfate were added, and the mixture was left for 48 hours in an ultrasound bath. Then, it was diluted with water and extracted three times with toluene. The combined organic phases were washed with water and saturated sodium chloride solution, dried on sodium sulfate and concentrated by evaporation in a vacuum. The residue was chromatographed on silica gel.

$^1$H-NMR (CDCl$_3$): δ=1.43 ppm s (9H); 3.91 t (J=6 Hz, 2H); 4.10 s (2H); 4.17 t (J=6 Hz, 2H); 6.75 d (J=2 Hz, 1H); 7.00 dd (J=10, 2 Hz, 1H); 7.24-7.36 m (5H); 7.45-7.56 m (5H); 7.76 d (J=10 Hz, 1H)

EXAMPLE 125

2-[2-[(1,2-Diphenyl-1H-benzimidazol-6-yl)oxy]ethoxy]acetic acid 50 mg of 2-[2-[(1,2-diphenyl-1H-benzimidazol-6-yl)oxy]ethoxy]acetic acid-tert-butyl ester was dissolved in 0.5 ml of trifluoroacetic acid and stirred for 48 hours. Then, it was diluted with water and extracted three times with ethyl acetate. The combined organic phases were washed with saturated sodium chloride solution, dried on sodium sulfate and concentrated by evaporation in a vacuum. The residue was chromatographed on silica gel.

Flash point 134-136° C.

EXAMPLE 126

2-[2-[(1,2-Diphenyl-1H-benzimidazol-6-yl)oxy]ethoxy]acetic acid methyl ester 35 mg of 2-[2-[(1,2-diphenyl-1H-benzimidazol-6-yl)oxy]ethoxy]acetic acid was dissolved in 0.4 ml of N,N-dimethylformamide and mixed with 29 mg of cesium carbonate and 50 μl of methyl iodide. It was stirred for 20 hours, then concentrated by evaporation in a vacuum and chromatographed on silica gel.

$^1$H-NMR (CDCl$_3$): δ=3.73 ppm s (3H); 3.93 t (J=6 Hz, 2H); 4.18 t (J=6 Hz, 2H); 4.25 s (2H); 6.73 d (J=2 Hz, 1H); 7.00 dd (J=10, 2 Hz, 1H); 7.25-7.42 m (5H); 7.46-7.58 m (5H); 7.77 d (J=10 Hz, 1H).

EXAMPLE 127

3-[2-[(1,2-Diphenyl-1H-benzimidazol-6-yl)oxy]ethoxy]propanoic acid-tert-butyl ester 0.2 g of [(1,2-diphenyl-1H-benzimidazol-6-yl)oxy]ethan-1-ol was suspended in 1.7 ml of toluene and 0.7 ml of tetrahydrofuran. 60 μl of acrylic acid-tert-butyl ester, 13 mg of tetrabutylammonium hydrogen sulfate, and 1.45 ml of 32% sodium hydroxide solution were added to it, and it was allowed to stir for 48 hours. Another 60 μl of acrylic acid-tert-butyl ester and 13 mg of tetrabutylammonium hydrogen sulfate were added, and the mixture was left for 48 hours in an ultrasound bath. Then, it was diluted with water and extracted three times with toluene. The combined organic phases were washed with water and saturated sodium chloride solution, dried on sodium sulfate and concentrated by evaporation in a vacuum. The residue was chromatographed on silica gel.

$^1$H-NMR (CDCl$_3$): δ=1.45 ppm s (9H); 2.52 t (J=8 Hz, 2H); 3.73-3.84 m (4H); 4.10 t (J=6 Hz, 2H); 6.72 d (J=2 Hz, 1H); 6.99 dd (J=10, 2 Hz, 1H); 7.22-7.83 m (5H); 7.45-7.57 m (5H); 7.75 d (J=10 Hz, 1H).

EXAMPLE 128

3-[2-[(1,2-Diphenyl-1H-benzimidazol-6-yl)oxy]ethoxy]propanoic acid 50 mg of 3-[2-[(1,2-diphenyl-1H-benzimidazol-6-yl)oxy]ethoxy]propanoic acid-tert-butyl ester was dissolved in 0.5 ml of trifluoroacetic acid and stirred for 15 hours. Then, it was diluted with water and extracted three times with ethyl acetate. The combined organic phases were washed with saturated sodium chloride solution, dried on sodium sulfate and concentrated by evaporation in a vacuum. The residue was chromatographed on silica gel.

$^1$H-NMR (D$_6$-DMSO): δ=2.26 ppm t (J=8 Hz, 2H); 3.60-3.70 m (4H); 3.98-4.06 m (2H); 6.65 d (J=2 Hz, 1H); 6.94 dd (J=10, 2 Hz, 1H); 7.30-7.62 m (10H); 7.68 d (J=10 Hz, 1H).

EXAMPLE 129

3-[2-[(1,2-Diphenyl-1H-benzimidazol-6-yl)oxy]ethoxy]propanoic acid methyl ester 35 mg of 3-[2-[(1,2-diphenyl-1H-benzimidazol-6-yl)oxy]ethoxy]propanoic acid was dissolved in 0.4 ml of N,N-dimethylformamide, mixed with 28 mg of cesium carbonate and 50 μl of methyl iodide and stirred for 30 hours. Then, it was diluted with water and extracted three times with ethyl acetate. The combined organic phases were washed with saturated sodium chloride solution, dried on sodium sulfate and concentrated by evaporation in a vacuum. The residue was chromatographed on silica gel.

Flash point 91-93° C.

EXAMPLE 130

3-[3-[(1,2-Diphenyl-1H-benzimidazol-6-yl)oxy]propoxy]propanoic acid-tert-butyl ester 0.2 g of 3-[(1,2-diphenyl-1H-benzimidazol-6-yl)oxy]propan-1-ol was suspended in 1.7 ml of toluene and 0.7 ml of tetrahydrofuran. 60 μl of acrylic acid-tert-butyl ester, 13 mg of tetrabutylammonium hydrogen sulfate, and 1.47 ml of 32% sodium hydroxide solution were added to it, and it was allowed to stir for 48 hours. Another 60 μl of acrylic acid-tert-butyl ester and 13 mg of tetrabutylammonium hydrogen sulfate were added, and the mixture was left for 48 hours in an ultrasound bath. Then, it was diluted with water and extracted three times with toluene. The combined organic phases were washed with water and saturated sodium chloride solution, dried on sodium sulfate and concentrated by evaporation in a vacuum. The residue was chromatographed on silica gel.

Flash point 95-98° C.

EXAMPLE 131

(E/Z)-5-(1,2-Diphenyl-1H-benzimidazol-6-yl)pent-4-enoic acid methyl ester a) 1,2-Diphenyl-6-methyl-1H-benzimidazole 5.1 g of 5-methyl-2-nitrodiphenylamine was hydrogenated in 55 ml of ethanol according to general operating instructions 1. The crude product was reacted with trimethyl orthobenzoate according to general operating instructions 3.
Flash point 134-136° C.

b) 1,2-Diphenyl-1H-benzimidazole-6-carbaldehyde 1 g of 1,2-diphenyl-6-methyl-1H-benzimidazole was suspended in 31 ml of 40% sulfuric acid and mixed with 13.5 g of cerium ammonium nitrate. It was allowed to stir for 2.5 hours at 80° C., cooled to 20° C., and carefully stirred into saturated aqueous sodium bicarbonate solution. The mixture was extracted three times with ethyl acetate, the combined extracts were washed with saturated aqueous sodium chloride solution, dried on sodium sulfate solution and evaporated to the dry state in a vacuum. The residue was chromatographed on silica gel.
$^1$H-NMR (CDCl$_3$): δ=7.30-7.42 ppm m (5H); 7.50-7.66 m (5H); 7.81 d (J=2 Hz, 1H); 7.89 dd (J=8, 2 Hz, 1H); 8.00 d (J=8 Hz, 1H); 10.05 s (1H).

(E/Z)-5-(1,2-Diphenyl-1H-benzimidazol-6-yl)pent-4-enoic acid methyl ester was obtained by reaction of 1,2-diphenyl-1H-benzimidazole-6-carbaldehyde according to general operating instructions 12 with 3-carboxypropyltriphenylphosphonium bromide.
$^1$H-NMR (CDCl$_3$): δ=2.40-2.71 ppm m (4H); 3.68 (3.66) at s (3H) each; 5.56-5.64 (6.12-6.22) at m (1H) each; 6.50 d (J=18 Hz, 1H); 6.58 d (broad) (J=12 Hz, 1H); 7.12 (7.15) at s (broad)(1H) each; 7.25-7.40 m (6H); 7.45-7.62 m (5H); 7.80 (7.83) at d (J=8 Hz, 1H) each.

EXAMPLE 132

E-5-(1,2-Diphenyl-1H-benzimidazol-6-yl)pent-4-enoic acid was obtained by reaction of (E/Z)-5-(1,2-diphenyl-1H-benzimidazol-6-yl)pent-4-enoic acid methyl ester according to general operating instructions 9.
$^1$H-NMR (CD$_3$OD): δ=2.26-2.43 ppm m (4H); 6.10-6.21 m (1H) 6.45 d (J=18 Hz, 1H); 7.08 s (1H); 7.22-7.52 m (11H); 7.59 d (J=8 Hz, 1H).

EXAMPLE 133

5-(1,2-Diphenyl-1H-benzimidazol-6-yl)pentanoic acid methyl ester was obtained by reaction of (E/Z)-5-(1,2-diphenyl-1H-benzimidazol-6-yl)pent-4-enoic acid methyl ester according to general operating instructions 1.
$^1$H-NMR (CDCl$_3$): δ=1.63-1.72 ppm m (4H); 2.30-2.39 m (2H); 2.68-2.77 m (2H); 3.65 (3H); 7.04 s (broad)(1H); 7.17 dd (J=8, 2 Hz, 1H); 7.25-7.38 m (5H); 7.45-7.60 m (5H); 7.79 d (J=8 Hz, 1H).

EXAMPLE 134

5-(1,2-Diphenyl-1H-benzimidazol-6-yl)pentanoic acid was obtained by reaction of 5-(1,2-diphenyl-1H-benzimidazol-6-yl)pentanoic acid methyl ester according to general operating instructions 9.
Flash point 192-193° C.

EXAMPLE 135

(E/Z)-6-(1,2-Diphenyl-1H-benzimidazol-6-yl)hex-5-enoic acid methyl ester was obtained by reaction of 1,2-diphenyl-1H-benzimidazole-6-carbaldehyde according to general operating instructions 12 with 4-carboxybutyltriphenylphosphonium bromide.
$^1$H-NMR (CDCl$_3$): δ=1.72-1.88 ppm m (2H); 2.20-2.42 m (4H); 3.65 (3.67) at s (3H, CH$_3$) each; 5.51-5.68 (6.10-6.20) at m (1H) each; 6.48 d (J=18 Hz, 1H); 6.56 d (broad)(J=12 Hz, 1H); 7.12 (7.16) at s (broad)(1H) each; 7.25-7.38 m (6H); 7.45-7.60 m (5H); 7.80 (7.84) at d (J=8 Hz, 1H) each.

EXAMPLE 136

(E/Z)-6-(1,2-Diphenyl-1H-benzimidazol-6-yl)hex-5-enoic acid was obtained by reaction of (E/Z)-6-(1,2-diphenyl-1H-benzimidazol-6-yl)hex-5-enoic acid methyl ester according to general operating instructions 9.
$^1$H-NMR (CDCl$_3$): δ=1.74-1.89 ppm m (2H); 2.22-2.43 m (4H); 5.58-5.68 (6.10-6.22) at m (1H) each; 6.47 d (J=18 Hz, 1H); 6.55 d (broad) (J=12 Hz, 1H); 7.11 (7.14) at s (broad)(1H) each; 7.25-7.40 m (6H); 7.48-7.59 m (5H); 7.80 (7.85) at d (J=8 Hz, 1H) each.

EXAMPLE 137

6-(1,2-Diphenyl-1H-benzimidazol-6-yl)hexanoic acid methyl ester was obtained by reaction of (E/Z)-6-(1,2-diphenyl-1H-benzimidazol-6-yl)hex-5-enoic acid methyl ester according to general operating instructions 1.
$^1$H-NMR (CDCl$_3$): δ=1.32-1.43 ppm m (2H); 1.62-1.74 m (4H); 2.31 t (J=7.5 Hz, 2H); 2.72 t (J=7.5 Hz, 2H); 3.56 s (3H); 7.02 s (broad)(1H); 7.18 dd (J=8, 2 Hz, 1H); 7.27-7.38 m (5H); 7.45-7.60 m (5H); 7.80 d (J=8 Hz, 1H).

EXAMPLE 138

6-(1,2-Diphenyl-1H-benzimidazol-6-yl)hexanoic acid was obtained by reaction of 6-(1,2-diphenyl-1H-benzimidazol-6-yl)hexanoic acid methyl ester according to general operating instructions 9.
$^1$H-NMR (CDCl$_3$): δ=1.30-1.45 ppm m (2H); 1.54-1.74 m (4H); 2.32 t (J=7.5 Hz, 2H); 2.70 t (J=7.5 Hz, 2H); 7.02 s (broad)(1H); 7.20 dd (J=8, 2 Hz, 1H); 7.25-7.38 m (5H); 7.42-7.60 m (5H); 7.81 d (J=8 Hz, 1H).

EXAMPLE 139

(E/Z)-7-(1,2-Diphenyl-1H-benzimidazol-6-yl)hept-6-enoic acid methyl ester was obtained by reaction of 1,2-diphenyl-1H-benzimidazole-6-carbaldehyde according to general operating instructions 12 with 5-carboxypentyltriphenylphosphonium bromide.

$^1$H-NMR (CDCl$_3$): δ=1.43-1.55 ppm m (2H); 1.58-1.72 m (2H); 2.18-2.38 m (4H); 3.65 (3.66) at s (3H, CH$_3$) each; 5.58-5.68 (6.12-6.22) at m (1H) each; 6.45 d (J=18 Hz, 1H); 6.54 d (broad)(J=12 Hz, 1H); 7.12 (7.14) at s (broad)(1H) each; 7.26-7.40 m (6H); 7.48-7.60 m (5H); 7.80 (7.83) at d (J=8 Hz, 1H) each.

EXAMPLE 140

(E/Z)-7-(1,2-Diphenyl-1H-benzimidazol-6-yl)hept-6-enoic acid was obtained by reaction of (E/Z)-7-(1,2-diphenyl-1H-benzimidazol-6-yl)hept-6-enoic acid methyl ester according to general operating instructions 9.

$^1$H-NMR (D$_6$-DMSO): δ=1.40-1.60 ppm m (4H); 2.14-2.28 m (4H); 6.18-6.30 m (1H); 6.50 d (J=18 Hz, 1H); 7.07 (7.12) at s (broad)(1H) each; 7.32-7.64 m (11H); 7.70 (7.78) at d (J=8 Hz, 1H) each; 12.00 s (broad)(1H).

EXAMPLE 141

7-(1,2-Diphenyl-1H-benzimidazol-6-yl)heptanoic acid methyl ester was obtained by reaction of (E/Z)-7-(1,2-diphenyl-1H-benzimidazol-6-yl)hept-6-enoic acid methyl ester according to general operating instructions 1.

$^1$H-NMR (CDCl$_3$): δ=1.30-1.42 ppm m (4H); 1.55-1.70 m (4H); 2.30 t (J=7.5 Hz, 2H); 2.68 t (J=7.5 Hz, 2H); 3.56 s (3H); 7.02 s (broad)(1H); 7.18 dd (J=8, 2 Hz, 1H); 7.28-7.35 m (5H); 7.45-7.58 m (5H); 7.79 d (J=8 Hz, 1H).

EXAMPLE 142

7-(1,2-Diphenyl-1H-benzimidazol-6-yl)heptanoic acid was obtained by reaction of 7-(1,2-diphenyl-1H-benzimidazol-6-yl)heptanoic acid methyl ester according to general operating instructions 9.
Flash point 99-103° C.

EXAMPLE 143

N-(1,2-Diphenyl-1H-benzimidazol-5-yl)benzenesulfonamide

EXAMPLE 144

N-(Phenylsulfonyl)-N-(1,2-diphenyl-1H-benzimidazol-5-yl)benzenesulfonamide a) 5-Amino-1,2-diphenyl-1H-benzimidazole 2,4-Diaminodiphenylamine is reacted with trimethyl orthobenzoate according to general operating instructions 3. $^1$H-NMR (CDCl$_3$): δ=6.70 ppm dd (J=7.5, 2 Hz, 1H); 7.06 d (J=7.5 Hz, 1H); 7.18 d (J=2 Hz, 1H); 7.28-7.60 m (10H).

5-Amino-1,2-diphenyl-1H-benzimidazole was reacted with benzenesulfonic acid chloride according to general operating instructions 13.

143: Flash point 196-205° C.
144: $^1$H-NMR (CDCl$_3$): δ=6.94 ppm dd (J=7.5, 2 Hz, 1H); 7.20 d (J=2 Hz, 1H); 7.26-8.04 m (21H).

EXAMPLE 145

3-Chloro-N-(1,2-Diphenyl-1H-benzimidazol-5-yl)benzenesulfonamide

EXAMPLE 146

N-[(3-Chlorophenyl)sulfonyl]-N-(1,2-diphenyl-1H-benzimidazol-5-yl)-(3-chlorobenzene)sulfonamide 5-Amino-1,2-diphenyl-1H-benzimidazole was reacted with 3-chlorobenzenesulfonic acid chloride according to general operating instructions 13.

145: Flash point 160-162° C.
146: $^1$H-NMR (CDCl$_3$): δ=6.93 ppm dd (J=7.5, 2 Hz, 1H); 7.25 d (J=2 Hz, 1H); 7.28-7.57 m (13H); 7.66 d (broad)(2H); 7.90 d (broad)(2H); 8.00 d (broad)(2H).

EXAMPLE 147

4-Chloro-N-(1,2-diphenyl-1H-benzimidazol-5-yl)benzenesulfonamide

5-Amino-1,2-diphenyl-1H-benzimidazole was reacted with 4-chlorobenzenesulfonic acid chloride according to general operating instructions 13.

$^1$H-NMR (CDCl$_3$): δ=6.86 ppm s (broad)(1H); 7.11 d (J=7.5, 2 Hz, 1H); 7.17 d (J=2 Hz, 1H); 7.25-7.55 m (12H); 7.70 d (J=10 Hz, 2H).

EXAMPLE 148

4-Bromo-N-(1,2-diphenyl-1H-benzimidazol-5-yl)benzenesulfonamide

EXAMPLE 149

N-(4-Bromophenylsulfonyl)-N-(1,2-diphenyl-1H-benzimidazol-5-yl)-4-bromobenzenesulfonamide 5-Amino-1,2-diphenyl-1H-benzimidazole was reacted with 4-bromobenzenesulfonic acid chloride according to general operating instructions 13.

148: Flash point 135-139° C.
149: $^1$H-NMR (CDCl$_3$): δ=6.90 ppm dd (J=7.5, 2 Hz, 1H); 7.23 d (J=2 Hz, 1H); 7.28-7.43 m (11H); 7.72 d (J=10 Hz, 2H); 7.86 d (J=10 Hz, 2H).

EXAMPLE 150

4-(Trifluoromethyl)-N-(1,2-diphenyl-1H-benzimidazol-5-yl)benzenesulfonamide

EXAMPLE 151

N-(1,2-Diphenyl-3H-benzimidazol-5-yl)-N-[(3-trifluoromethyl)phenylsulfonyl]-(3-trifluoromethyl)benzenesulfonamide 5-Amino-1,2-diphenyl-1H-benzimidazole was reacted with (3-trifluoromethyl)benzenesulfonic acid chloride according to general operating instructions 13.

150: Flash point 116-121° C.
151: Flash point 238-241° C.

EXAMPLE 152

3-Methyl-N-(1,2-diphenyl-1H-benzimidazol-5-yl)benzenesulfonamide

EXAMPLE 153

N-(1,2-Diphenyl-1H-benzimidazol-5-yl)-N-(3-methylphenylsulfonyl)-3-methylbenzenesulfonamide 5-Amino-1,2-diphenyl-1H-benzimidazole was reacted with 3-methylbenzenesulfonic acid chloride according to general operating instructions 13.

152: Flash point 192-195° C.
153: Flash point 173-176° C.

EXAMPLE 154

4-Methyl-N-(1,2-Diphenyl-1H-benzimidazol-5-yl)benzenesulfonamide

EXAMPLE 155

N-(1,2-Diphenyl-1H-benzimidazol-5-yl)-N-(4-methylphenylsulfonyl)-4-methyl-benzenesulfonamide 5-Amino-1,2-diphenyl-1H-benzimidazole was reacted with 4-methylbenzenesulfonic acid chloride according to general operating instructions 13.

154: $^1$H-NMR (CDCl$_3$): δ=2.38 ppm s (3H); 6.77 s (broad)(1H); 7.14-7.55 m (14H); 7.66 d (J=10 Hz, 2H).
155: Flash point 234-236° C.

EXAMPLE 156

4-Methoxy-N-(1,2-Diphenyl-1H-benzimidazol-5-yl)benzenesulfonamide

EXAMPLE

N-(1,2-Diphenyl-1H-benzimidazol-5-yl)-N-(4-methoxyphenylsulfonyl)-4-methoxybenzenesulfonamide 5-Amino-1,2-diphenyl-1H-benzimidazole was reacted with 4-methoxybenzenesulfonic acid chloride according to general operating instructions 13.

156: $^1$H-NMR (CDCl$_3$): δ=3.82 ppm s (3H); 6.78 s (broad)(1H, H-4); 6.88 d (J=7.5 Hz, 1H); 7.14 d (J=1.5 Hz, 1H); 7.28-7.55 m (12H); 7.72 d (J=8 Hz, 2H).

157: $^1$H-NMR (CDCl$_3$): δ=3.90 ppm s (6H); 6.93 dd (J=7.5, 2 Hz, 1H); 7.00 d (J=10 Hz, 4H); 7.06 d (J=2 Hz, 1H); 7.30-7.58 m (11H); 7.93 d (J=10 Hz, 4H).

EXAMPLE 158

N-(1,2-Diphenyl-1H-benzimidazol-5-yl)propanesulfonamide

EXAMPLE 159

N-(1,2-Diphenyl-1H-benzimidazol-5-yl)-N-(propylsulfonyl)-propanesulfonamide

5-Amino-1,2-diphenyl-1H-benzimidazole was reacted with propanebenzenesulfonic acid chloride according to general operating instructions 13.

158: $^1$H-NMR (CDCl$_3$/D$_6$-DMSO): δ=0.80 ppm t (J=7.5 Hz, 3H); 1.65 m (2H); 2.82 m (2H); 6.95 d (J=7.5 Hz, 1H); 7.08 dd (J=7.5, 2 Hz, 1H); 7.10-7.40 m (10H); 7.61 d (J=2 Hz, 1H); 9.05 s (broad)(1H, NH).

159: $^1$H-NMR (CDCl$_3$): δ=1.08 ppm t (J=7.5 Hz, 3H); 1.12 t (J=7.5 Hz, 3H); 2.00 m (4H); 3.60 m (4H); 7.25-7.63 m (13H).

EXAMPLE 160

N-(1,2-Diphenyl-1H-benzimidazol-5-yl)benzenemethanesulfonamide

5-Amino-1,2-diphenyl-1H-benzimidazole was reacted with benzenemethanesulfonic acid chloride according to general operating instructions 13.

Flash point 185-188° C.

EXAMPLE 161

6-[[1,2-Diphenyl-1H-benzimidazol-5-yl]amino]hexanoic acid methyl ester

EXAMPLE 162

6-[N-(1,2-Diphenyl-1H-benzimidazol-5-yl)-N-[(5-methoxycarbonyl)-pentyl]amino]hexanoic acid methyl ester 207 mg of 6-bromohexanoic acid methyl ester, 138 mg of potassium carbonate and 150 mg of sodium iodide were added to a solution of 285 mg of 5-amino-1,2-diphenyl-1H-benzimidazole in 5 ml of methanol, and it was allowed to stir for 3 days at 20° C. It was mixed with water, extracted three times with ethyl acetate, the combined organic phases were dried on sodium sulfate and concentrated by evaporation in a vacuum. The residue was chromatographed on silica gel.

161: Flash point 109-113° C.
162: $^1$H-NMR (CDCl$_3$): δ=1.30-1.43 m (4H); 1.53-1.73 m (8H); 2.32 t (J=7.5 Hz, 4H); 3.30 t (J=7.5 Hz, 4H); 3.68 s (6H); 6.75 dd (J=10, 2 Hz, 1H); 7.10 d (J=10 Hz, 1H); 7.14 d (J=2 Hz, 1H); 7.23-7.35 m (5H); 7.42-7.58 m (5H).

EXAMPLE 163

6-[[1,2-Diphenyl-1H-benzimidazol-5-yl]amino]hexanoic acid was obtained by reaction of 6-[[1,2-diphenyl-1H-benzimidazol-5-yl]amino]hexanoic acid methyl ester according to general operating instructions 9.

$^1$H-NMR (D$_6$-DMSO): δ=1.35-1.50 ppm m (2H); 1.50-1.68 m (4H); 2.23 t (J=7.5 Hz, 2H); 3.05 t (J=7.5 Hz, 2H); 6.67 dd (J=10, 2 Hz, 1H); 6.80 d (J=2 Hz, 1H); 6.92 d (J=10 Hz, 1H); 7.30-7.40 m (4H); 7.45-7.62 m (6H).

EXAMPLE 164

6-[[2-Phenyl-1-[4-(phenylmethoxy)phenyl]-1H-benzimidazol-6-yl]oxy]hexanoic acid methyl ester a) (5-Hydroxy-2-nitrophenyl)[(4-(phenylmethoxy)phenyl]amine 1 g of 3-fluoro-4-nitrophenol and 3.8 g of 4-benzyloxyaniline were stirred for 6.5 hours at 150° C. The batch was then diluted with dichloromethane. After two cycles of extraction with 1N aqueous hydrochloric acid and washing with water, it was extracted twice with 2N aqueous sodium hydroxide solution. The basic water phase was mixed with ethyl acetate and 1N aqueous hydrochloric acid. After phase separation, the organic phase was extracted several times with 1N aqueous hydrochloric acid. After the organic phase was washed with saturated sodium chloride solution, it was dried on sodium sulfate, concentrated by evaporation in a vacuum, and the residue was chromatographed on silica gel.

$^1$H-NMR (D$_6$-DMSO): δ=5.14 ppm s (2H); 6.23 m (2H); 7.10 d (J=8 Hz, 2H); 7.26 d (J=8 Hz, 2H); 7.32-7.52 m (5H); 8.03 d (J=8 Hz, 1H); 9.52 s (1H); 10.71 s (1H).

b) 6-[[4-Nitro-3-[[4-(phenylmethoxy)phenyl]amino]-phenyl]oxy]hexanoic acid methyl ester was obtained by reaction of (5-hydroxy-2-nitrophenyl)[(4-(phenylmethoxy)phenyl]amine with 6-bromohexanoic acid methyl ester according to general operating instructions 8.

$^1$H-NMR (CDCl$_3$): δ=1.37-1.50 m (2H); 1.59-1.80 m (4H); 2.33 t (J=7.5 Hz, 2H); 3.67 s (3H); 3.83 t (J=7.5 Hz, 2H); 5.12 s (2H); 6.24-6.33 m (2H);-7.04 d (J=8 Hz, 2H); 7.21 d (J=8 Hz, 2H); 7.32-7.50 m (5H); 8.17 d (J=8 Hz, 1H); 9.66 s (1H).

6-[[2-Phenyl-1-[4-(phenylmethoxy)phenyl]-1H-benzimidazol-6-yl]oxy]hexanoic acid methyl ester was obtained by reduction of 6-[[4-nitro-3-[[4-(phenylmethoxy)phenyl]amino]phenyl]oxy]hexanoic acid methyl ester according to general operating instructions 2 and subsequent cyclization with trimethyl orthobenzoate according to general operating instructions 3.

$^1$H-NMR (CDCl$_3$): δ=1.43-1.58 m (2H); 1.65-1.86 m (4H), 2.35 t (J=7.5 Hz, 2H); 3.67 s (3H); 3.94 t (J=7.5 Hz, 2H); 5.14 s (2H); 6.64 d (J=2 Hz, 1H); 6.95 dd (J=8, 2 Hz, 1H); 7.11 d (J=8 Hz, 2H); 7.18-7.61 m (12H); 7.74 d (J=8 Hz, 1H).

EXAMPLE 165

6-[[2-Phenyl-1-[4-(phenylmethoxy)phenyl]-1H-benzimidazol-6-yl]oxy]hexanoic acid

6-[[2-Phenyl-1-[4-(phenylmethoxy)phenyl]-1H-benzimidazol-6-yl]oxy]hexanoic acid methyl ester was reacted according to general operating instructions 9.

$^1$H-NMR (D$_6$-DMSO): δ=1.36-1.62 m (4H); 1.65-1.78 m (2H); 2.22 t (J=7.5 Hz, 2H); 3.92 t (J=7.5 Hz, 2H); 5.18 s (2H); 6.59 d (J=2 Hz, 1H); 6.92 dd (J=8, 2 Hz, 1H); 7.20 d (J=8 Hz, 2H); 7.30-7.54 m (12H); 7.66 d (J=8 Hz, 1H).

EXAMPLE 166

6-[[1-(4-Hydroxyphenyl)-2-phenyl-1H-benzimidazol-6-yl]oxy]hexanoic acid

6-[[2-Phenyl-1-[4-(phenylmethoxy)phenyl]-1H-benzimidazol-6-yl]oxy]hexanoic acid was reacted according to general operating instructions 1.

$^1$H-NMR (D$_6$-DMSO): δ=1.37-1.79 m (6H); 2.22 t (J=7.5 Hz, 2H); 3.92 t (J=7.5 Hz, 2H); 6.60 d (J=2 Hz, 1H); 6.91 dd (J=8, 2 Hz, 1H); 6.94 d (J=8 Hz, 2H); 7.20 d (J=8 Hz, 2H); 7.36 m (3H); 7.52 m (2H); 7.63 d (J=8 Hz, 1H).

EXAMPLE 167

6-[[2-Phenyl-1-[3-(phenylmethoxy)phenyl]-1H-benzimidazol-6-yl]oxy]hexanoic acid methyl ester a) (5-Hydroxy-2-nitrophenyl)[(3-(phenylmethoxy)phenyl]amine 1 g of 3-fluoro-4-nitrophenol and 3.81 g of 3-benzyloxyaniline were stirred for 22 hours at 150° C. Then, it was taken up in a little dichloromethane and chromatographed directly on silica gel.

$^1$H-NMR (CDCl$_3$): δ=5.10 ppm s (2H); 5.82 s (br) (1H); 6.27 dd (J=8, 2 Hz, 1H); 6.48 d (J=2 Hz, 1H); 6.86 m (3H); 7.28-7.48 m (5H); 8.15 d (J=8 Hz, 1H); 9.52 s (br) (1H); 10.71 s (1H).

b) 6-[[4-Nitro-3-[[3-(phenylmethoxy)phenyl]amino]phenyl]-oxy]hexanoic acid methyl ester was obtained by reaction of (5-hydroxy-2-nitrophenyl)[(3-(phenylmethoxy)phenyl]amine with 6-bromohexanoic acid methyl ester according to general operating instructions 8.

$^1$H-NMR (CDCl$_3$): δ=1.40-1.53 m (2H); 1.61-1.82 m (4H); 2.34 t (J=7.5 Hz, 2H); 3.67 s (3H); 3.88 t (J=7.5 Hz, 2H); 5.10 s (2H); 6.33 dd (J=8, 2 Hz, 1H); 6.58 d (J=2 Hz, 1H); 6.83-6.96 m (3H); 7.28-7.49 m (5H); 8.17 d (J=8 Hz, 1H); 9.74 s (br).

6-[[2-Phenyl-1-[3-(phenylmethoxy)phenyl]-1H-benzimidazol-6-yl]oxy]hexanoic acid methyl ester was obtained by reduction of 6-[[4-nitro-3-[[3-(phenylmethoxy)phenyl]amino]phenyl]oxy]hexanoic acid methyl ester according to general operating instructions 2 and subsequent cyclization with trimethyl orthobenzoate according to general operating instructions 3.

$^1$H-NMR (CDCl$_3$): δ=1.45-1.60 m (2H); 1.66-1.88 m (4H); 2.35 t (J=7.5 Hz, 2H); 3.68 s (3H); 3.93 t (J=7.5 Hz, 2H); 5.02 s (2H); 6.69 d (J=2 Hz, 1H); 6.90 m (2H); 6.97 dd (J=8, 2 Hz, 1H); 7.11 ddd (J=8, 2, 2 Hz, 1H); 7.28-7.46 m (9H); 7.78 d (J=8 Hz, 1H).

EXAMPLE 168

ZK 212262 NEU+

6-[[2-Phenyl-1-[3-(phenylmethoxy)phenyl]-1H-benzimidazol-6-yl]oxy]hexanoic acid

6-[[2-Phenyl-1-[3-(phenylmethoxy)phenyl]-1H-benzimidazol-6-yl]oxy]hexanoic acid methyl ester was reacted according to general operating instructions 9.

$^1$H-NMR (CDCl$_3$): δ=1.49-1.62 m (2H), 1.67-1.88 m (4H); 2.39 t (J=7.5 Hz, 2H); 3.93 t (J=7.5 Hz, 2H); 5.03 s (2H); 6.68 d (J=2 Hz, 1H); 6.91 m (3H), 6.98 dd (J=8, 2 Hz, 1H); 7.12 ddd (J=8, 2, 2 Hz, 1H); 7.29-7.47 m (8H); 7.57 d (J=8 Hz, 2H); 7.81 d (J=8 Hz, 1H).

EXAMPLE 169

6-[[1-(3-Hydroxyphenyl)-2-phenyl-1H-benzimidazol-6-yl]oxy]hexanoic acid

6-[[2-Phenyl-1-[3-(phenylmethoxy)phenyl]-1H-benzimidazol-6-yl]oxy]hexanoic acid was reacted according to general operating instructions 1.

$^1$H-NMR (D$_6$-DMSO): δ=1.39-1.80 m (6H); 2.23 t (J=7.5 Hz, 2H); 3.94 t (J=7.5 Hz, 2H); 6.57 d (J=2 Hz, 1H); 6.74 dd (J=2, 2 Hz, 1H); 6.84 dd (J=8, 2 Hz, 1H); 6.94 m (2H); 7.38 m (4H); 7.53 m (2H); 7.66 d (J=8 Hz, 1H).

EXAMPLE 170

6-[[1-(3-Hydroxyphenyl)-2-phenyl-1H-benzimidazol-6-yl]oxy]hexanoic acid methyl ester 6-[[2-Phenyl-1-[3-(phenylmethoxy)phenyl]-1H-benzimidazol-6-yl]oxy]hexanoic acid methyl ester was reacted according to general operating instructions 1.

$^1$H-NMR (D$_6$-DMSO): δ=1.38-1.80 m (6H); 2.32 t (J=7.5 Hz, 2H); 3.59 s (3H); 3.94 t (J=7.5 Hz, 2H); 6.66 d (J=2 Hz, 1H); 6.74 dd (J=2, 2 Hz, 1H); 6.83 dd (J=8, 2 Hz, 1H); 6.93 dd (J=8, 2 Hz, 2H); 7.38 m (4H); 7.54 m (2H); 7.67 d (J=8 Hz, 1H).

EXAMPLE 171

6-[[1-(3-Nitrophenyl)-2-phenyl-1H-benzimidazol-6-yl]oxy]hexanoic acid ethyl ester was obtained by reaction of 6-hydroxy-1-(3-nitrophenyl)-2-phenylbenzimidazole (DE 4330959) with 6-bromohexanoic acid ethyl ester according to general operating instructions 8.

Flash point 104-106° C.

EXAMPLE 172

6-[[4-Bromo-1-(4-methylphenyl)-2-phenyl-1H-benzimidazol-6-yl]oxy]hexanoic acid methyl ester a) 4-Bromo-6-methoxy-2-phenyl-1H-benzimidazole 36.6 g of 4-amino-3-bromo-5-nitroanisole (J. Chem. Soc. 1966, 1769) was introduced into 750 ml of ethanol and mixed with 19.8 g of iron powder and 126 ml of acetic acid. After being stirred for 2.5 hours at 55° C., it was mixed with 350 ml of dichloromethane and made basic with 2N sodium hydroxide solution. After filtration on Celite, it was washed with water and saturated common salt solution and concentrated by evaporation. The crude phenyldiamine that was thus obtained was reacted with trimethyl orthobenzoate according to general operating instructions 3.

Flash point 203-205° C.

b) 4-Bromo-6-methoxy-1-(4-methylphenyl)-2-phenyl-1H-benzimidazole 2.5 g of 4-bromo-6-methoxy-2-phenyl-1H-benzimidazole and 2.24 g of 4-(methylbenzene)boronic acid were stirred with 1.5 g of anhydrous copper(II) acetate and about 3 g of molecular sieve in 35 ml of pyridine for 7 hours at 100° C. After dichloromethane and Celite were added, it was concentrated by evaporation and chromatographed on silica gel with a hexane/ethyl acetate mixture.

Flash point 209-210° C.

c) 4-Bromo-6-hydroxy-1-(4-methylphenyl)-2-phenyl-1H-benzimidazole 1.2 g of 4-bromo-6-methoxy-1-(4-methylphenyl)-2-phenyl-1H-benzimidazole, 6 ml of acetic acid and 6 ml of aqueous hydrobromic acid (62%) are boiled for 5.5 hours. Then, it is precipitated with water, and the precipitate is suctioned off. The latter was then dispersed between ethyl acetate and 2N sodium hydroxide solution. After the organic phase was washed with water, it was concentrated by evaporation.

Flash point 136-137° C.

6-[[4-Bromo-1-(4-methylphenyl)-2-phenyl-1H-benzimidazol-6-yl]oxy]hexanoic acid methyl ester was obtained by reaction of 4-bromo-6-hydroxy-1-(4-methylphenyl)-2-phenyl-1H-benzimidazole with 6-bromohexanoic acid methyl ester according to general operating instructions 8.

Flash point 136° C.

EXAMPLE 173

6-[[4-Acetyl-1-(4-methylphenyl)-2-phenyl-1H-benzimidazol-6-yl]oxy]hexanoic acid methyl ester 0.5 g of 4-bromo-6-hydroxy-1-(4-methylphenyl)-2-phenyl-1H-benzimidazole, 0.37 ml (α-ethoxyvinyl)tributyltin, and 140 mg of dichlorobis(triphenylphosphine)palladium were stirred in 10 ml of toluene for 18 hours at 100° C. After cooling, it was stirred with 2N aqueous hydrochloric acid for 0.25 hour. After phase separation, the organic phase was washed with water and concentrated by evaporation. The residue was chromatographed on silica gel with a hexane/ethyl acetate mixture.

Flash point 114-115° C.

EXAMPLE 174

6-[[1-(4-Methylphenyl)-2-phenyl-1H-benzimidazol-5-yl]oxy]hexanoic acid methyl ster a) 5-Methoxy-1-(4-methylphenyl)-2-phenyl-1H-benzimidazole 16.8 g of 5-methoxy-2-phenyl-1H-benzimidazole (Bull. Sci. Fac. Chim. Ind. Bologna, 11, 1953, 42) and 20.4 g of 4-(methylbenzene)boronic acid are reacted according to general operating instructions 14.

¹H-NMR (CDCl₃): δ=2.45 s (3H); 3.91 s (3H); 6.90 dd (J=8, 2 Hz, 1H); 7.12 d (J=8 Hz, 1H); 7.18 d (J=8 Hz, 2H); 7.25-7.38 m (6H); 7.57 m (2H).

In addition, 6-methoxy-1-(4-methylphenyl)-2-phenyl-1H-benzimidazole was obtained.

b) 5-Hydroxy-1-(4-methylphenyl)-2-phenyl-1H-benzimidazole was obtained from 5-methoxy-1-(4-methylphenyl)-2-phenyl-1H-benzimidazole according to general operating instructions 6.

Flash point 270° C.

6-[[1-(4-Methylphenyl)-2-phenyl-1H-benzimidazol-5-yl]oxy]hexanoic acid methyl ester was obtained from 5-hydroxy-1-(4-methylphenyl)-2-phenyl-1H-benzimidazole by reaction with 6-bromohexanoic acid methyl ester according to general operating instructions 8.

¹H-NMR (CDCl₃): δ=1.48-1.92 m (6H); 2.38 t (J=7.5 Hz, 2H); 2.46 s (3H); 3.69 s (3H); 4.06 t (J=7.5 Hz, 2H); 6.89 dd (J=8, 2 Hz, 1H); 7.11 d (J=8 Hz, 1H); 7.18 d (J=8 Hz, 2H); 7.24-7.37 m (6H), 7.57 m (2H).

EXAMPLE 175

6-[[1-(4-Methylphenyl)-2-phenyl-1H-benzimidazol-5-yl]oxy]hexanoic acid was obtained from 6-[[1-(4-methylphenyl)-2-phenyl-1H-benzimidazol-5-yl]oxy]hexanoic acid methyl ester according to general operating instructions 9.

¹H-NMR (D₆-DMSO) δ=1.41-1.67 m (4H); 1.70-1.83 m (2H); 2.26 t (J=7.5 Hz, 2H); 2.43 s (3H); 4.05 t (J=7.5 Hz, 2H); 6.90 dd (J=8, 2 Hz, 1H); 7.04 d (J=8 Hz, 1H); 7.23-7.40 m (8H); 7.52 m (2H); 11.92 s (br.) (1H).

EXAMPLE 176

6-[[2-Phenyl-1-[4-(thiomethyl)phenyl]-1H-benzimidazol-5-yl]oxy]hexanoic acid methyl ester a) 6-[[2-Phenyl]-1H-benzimidazol-5-yl]oxy]hexanoic acid methyl ester 4.84 g of 2-phenyl-5-hydroxy-1H-benzimidazole (Izv. Akad. Nauk. SSSR Ser. Chim. 8, 1990, 1888) was obtained by reaction with 6-bromohexanoic acid methyl ester according to general operating instructions 8.

¹H-NMR (CDCl₃): δ=1.43-1.58 m (2H); 1.64-1.87 m (4H); 2.37 t (J=7.5 Hz, 2H); 3.69 s (3H); 3.94 t (J=7.5 Hz, 2H); 6.87 dd (J=8, 2 Hz, 1H); 7.02 s (br.); 7.40-7.57 m (4H); 8.05 m (2H).

6-[[2-Phenyl-1-[4-(thiomethyl)phenyl]-1H-benzimidazol-5-yl]oxy]hexanoic acid methyl ester was obtained by reaction of 6-[[2-phenyl]-1H-benzimidazol-5-yl]oxy]hexanoic acid methyl ester with 4-(thiomethylbenzene)boronic acid according to general operating instructions 14.

¹H-NMR (CDCl₃): δ=1.48-1.61 m (2H); 1.66-1.92 m (4H); 2.36 t (J=7.5 Hz, 2H); 2.54 s (3H); 3.68 s (3H); 4.05 t (J=7.5 Hz, 2H); 6.90 dd (J=8, 2 Hz, 1H); 7.11 d (J=8 Hz, 1H); 7.22 d (J=8 Hz, 2H); 7.27-7.49 m (6H); 7.57 m (2H).

EXAMPLE 177

6-[[2-Phenyl-1-[(4-thiomethyl)phenyl]-1H-benzimidazol-6-yl]oxy]hexanoic acid methyl ester was obtained by reaction of 6-[[2-phenyl]-1H-benzimidazol-5-yl]oxy]hexanoic acid methyl ester with 4-(thiomethylbenzene)boronic acid according to general operating instructions 14.

¹H-NMR (CDCl₃): δ=1.45-1.57 m (2H); 1.62-1.86 m (4H); 2.44 t (J=7.5 Hz, 2H); 2.56 s (3H); 3.66 s (3H); 3.93 t (J=7.5 Hz, 2H); 6.66 d (J=2 Hz, 1H); 6.96 dd (J=8, 2 Hz, 1H); 7;18-7.39 m (7H); 7.54 m (2H); 7.73 d (J=8 Hz, 1H).

EXAMPLE 178

6-[[2-Phenyl-1-(3-thienyl)-1H-benzimidazol-5-yl]oxy]hexanoic acid methyl ester was obtained by reaction of 6-[[2-phenyl]-1H-benzimidazol-5-yl]oxy]hexanoic acid methyl ester with thiophene-3-boronic acid according to general operating instructions 14.

¹H-NMR (CDCl₃): δ=1.48-1.62 m (2H); 1.66-1.92 m (4H); 2.47 t (J=7.5 Hz, 2H); 3.68 s (3H); 4.04 t (J=7.5 Hz, 2H); 6.93 dd (J=8, 2 Hz, 1H); 6.98 dd (J=5, 1 Hz, 1H); 7.18 d (J=8 Hz, 1H); 7.28 dd (J=3, 1 Hz, 1H); 7.30-7.40 m (4H), 7.46 dd (J=5, 3 Hz, 1H); 7.60 m (2H).

EXAMPLE 179

6-[[2-Phenyl-1-(3-thienyl)-1H-benzimidazol-6-yl]oxy]hexanoic acid methyl ester was obtained by reaction of 6-[[2-phenyl]-1H-benzimidazol-5-yl]oxy]hexanoic acid methyl ester with thiophene-3-boronic acid according to general operating instructions 14.

¹H-NMR (CDCl₃): δ=1.45-1.58 m (2H); 1.64-1.87 m (4H); 2.35 t (J=7.5 Hz, 2H); 3.67 s (3H); 3.97 t (J=7.5 Hz, 2H); 6.74 d (J=2 Hz, 1H); 6.95 dd (J=8, 2 Hz, 1H); 7.01 dd (J=5, 1 Hz, 1H); 7.29 dd (J=3, 1 Hz, 1H); 7.30-7.38 m (4H); 7.47 dd (J=5, 3 Hz, 1H); 7.58 m (2H); 7.73 d (J=8 Hz, 1H).

EXAMPLE 180

4-[3-[[1-(4-Methylphenyl)-2-phenyl-1H-benzimidazol-6-yl]oxy]phenoxy]butanoic acid methyl ester a) 6-(3-Methoxyphenoxy)-1-(4-methylphenyl)-2-phenyl-1H-benzimidazole was obtained from 6-hydroxy-1-(4-methylphenyl)-2-phenyl-1H-benzimidazole and 3-methoxybenzeneboronic acid according to general operating instructions 14.

Flash point 120-122° C.

b) 3-[[1-(4-Methylphenyl)-2-phenyl-1H-benzimidazol-6-yl]oxy]phenol was obtained by reaction of 6-(3-methoxyphenoxy)-1-(4-methylphenyl)-2-phenyl-1H-benzimidazole according to general operating instructions 6 with the addition of 10 mol % of hexadecyltributyl phosphonium bromide.
Flash point 252-253° C.

4-[3-[[1-(4-Methylphenyl)-2-phenyl-1H-benzimidazol-6-yl]oxy]phenoxy]butanoic acid methyl ester was obtained by reaction of 3-[[1-(4-methylphenyl)-2-phenyl-1H-benzimidazol-6-yl]oxy]phenol with 4-bromobutyric acid methyl ester according to general operating instructions 8.
$^1$H-NMR (CDCl$_3$): δ=2.00-2.13 nm (2H); 2.43 s (3H); 2.50 t (J=7.5 Hz, 2H); 3.67 s (3H); 3.93 t (J=7.5 Hz, 2H); 6.44-6.62 m (3H); 6.95 d (J=2 Hz, 1H); 7.06 dd (J=8, 2 Hz, 1H); 7.12-7.22 m (3H); 7.25-7.39 m (5H); 7.59 m (2H); 7.87 d (J=8 Hz, 1H).

EXAMPLE 181

4-[4-[[1-(4-Methylphenyl)-2-phenyl-1H-benzimidazol-6-yl]oxy]phenoxy]butanoic acid methyl ester a) 6-(4-Methoxyphenoxy)-1-(4-methylphenyl)-2-phenyl-1H-benzimidazole was obtained from 6-hydroxy-1-(4-methylphenyl)-2-phenyl-1H-benzimidazole and 4-methoxybenzeneboronic acid according to general operating instructions 14.
$^1$H-NMR (CDCl$_3$): δ=2.44 s (3H); 3.79 s (3H); 6.82-6.98 m (5H); 7.01 dd (J=8, 2 Hz, 1H); 7.17 d (J=8 Hz, 2H); 7.25-7.41 m (5H); 7.57 m (2H); 7.82 d (J=8 Hz, 1H).

b) 4-[[1-(4-Methylphenyl)-2-phenyl-1H-benzimidazol-6-yl]oxy]phenol was obtained by reaction of 6-(3-methoxyphenoxy)-1-(4-methylphenyl)-2-phenyl-1H-benzimidazole according to general operating instructions 6 with the addition of 10 mol % of hexadecyltributyl phosphonium bromide.
$^1$H-NMR (D$_6$-DMSO): δ=2.38 s (3H); 6.61 d (J=2 Hz, 1H); 6.74 d (J=8 Hz, 2H); 6.86 d (J=8 Hz, 2H); 6.91-7.01 m (2H); 7.22-7.41 m (6H); 7.49 m (2H); 7.75 d (J=8 Hz, 1H); 9.32 s (1H).

4-[4-[[1-(4-Methylphenyl)-2-phenyl-1H-benzimidazol-6-yl]oxy]phenoxy]butanoic acid methyl ester was obtained by reaction of 4-[[1-(4-methylphenyl)-2-phenyl-1H-benzimidazol-6-yl]oxy]phenol with 4-bromobutyric acid methyl ester according to general operating instructions 8.
$^1$H-NMR (CDCl$_3$): δ=2.03-2.16 m (2H); 2.42 s (3H); 2.53 t (J=7.5 Hz, 2H); 3.69 s (3H); 3.97 t (J=7.5 Hz, 2H); 6.78-6.94 m (5H); 6.99 dd (J=8, 2 Hz, 1H); 7.16 d (J=8, Hz, 2H); 7.24-7.38 m (5H); 7.57 m (2H); 7.79 d (J=8 Hz, 1H).

EXAMPLE 182

[4-[[1-(4-Methylphenyl)-2-phenyl-1H-benzimidazol-6-yl]oxy]phenoxy]acetic acid methyl ester was obtained by reaction of 4-[[1-(4-methylphenyl)-2-phenyl-1H-benzimidazol-6-yl]oxy]phenol with bromoacetic acid methyl ester according to general operating instructions 8.
$^1$H-NMR (CDCl$_3$): δ=2.43 s (3H); 3.82 s (3H); 4.61 s (2H); 6.78-6.96 m (5H); 7.00 dd (J=8, 2 Hz, 1H); 7.14 d (J=8, Hz, 2H); 7.23-7.38 m (5H); 7.56 m (2H); 7.80 d (J=8 Hz, 1H).

EXAMPLE 183

4-[(1,2-Diphenyl-1H-benzimidazol-6-yl)oxy]butanoic acid methyl ester was obtained by reaction of 1,2-diphenyl-6-hydroxy-1H-benzimidazole with 4-bromobutanoic acid methyl ester according to general operating instructions 8.
Flash point 107-110° C.

EXAMPLE 184

6-[[2-Phenyl-1-(3-pyridyl)-1H-benzimidazol-5-yl]oxy]hexanoic acid methyl ester was obtained by reaction of 6-[[2-phenyl]-1H-benzimidazol-5-yl]oxy]hexanoic acid methyl ester with pyridine-3-boronic acid according to general operating instructions 14.
MS (EI): 415 (molecular ion peak)

EXAMPLE 185

6-[[2-Phenyl-1-(3-pyridyl)-1H-benzimidazol-6-yl]oxy]hexanoic acid methyl ester was obtained by reaction of 6-[[2-phenyl]-1H-benzimidazol-5-yl]oxy]hexanoic acid methyl ester with pyridine-3-boronic acid according to general operating instructions 14.
MS (EI): 415 (molecular ion peak)

EXAMPLE 186

6-[[2-Phenyl-1-(2-pyridyl)-1H-benzimidazol-5-yl]oxy]hexanoic acid was obtained by reaction of 6-[[2-phenyl]-1H-benzimidazol-5-yl]oxy]hexanoic acid methyl ester with 2-fluoro-pyridine according to general operating instructions 15.
MS (EI): 401 (molecular ion peak)

EXAMPLE 187

6-[[2-Phenyl-1-(2-pyridyl)-1H-benzimidazol-6-yl]oxy]hexanoic acid was obtained by reaction of 6-[[2-phenyl]-1H-benzimidazol-5-yl]oxy]hexanoic acid methyl ester with 2-fluoro-pyridine according to general operating instructions 15.
MS (EI): 401 (molecular ion peak)

EXAMPLE 188

6-[[2-Phenyl-1-(4-pyridyl)-1H-benzimidazol-6-yl]oxy]hexanoic acid methyl ester was obtained by reaction of 6-[[2-phenyl]-1H-benzimidazol-5-yl]oxy]hexanoic acid methyl ester with pyridine-4-boronic acid according to general operating instructions 14.
MS (EI): 415 (molecular ion peak)

EXAMPLE 189

6-[[2-(4-Fluorophenyl)-1-phenyl-1H-benzimidazol-6-yl]oxy]hexanoic acid methyl ester was obtained by reaction of 6-[[4-amino-3-(phenylamino)phenyl]oxy]hexanoic acid methyl ester with 4-fluorobenzoyl chloride according to general operating instructions 5.

MS (EI): 432 (molecular ion peak)

EXAMPLE 190

6-[[2-(4-Methoxyphenyl)-1-phenyl-1H-benzimidazol-6-yl]oxy]hexanoic acid methyl ester was obtained by reaction of 6-[[4-amino-3-(phenylamino)phenyl]oxy]hexanoic acid methyl ester with 4-methoxybenzoyl chloride according to general operating instructions 5.

MS (EI): 444 (molecular ion peak)

EXAMPLE 191

6-[[2-(3-Fluorophenyl)-1-phenyl-3H-benzimidazol-6-yl]oxy]hexanoic acid methyl ester was obtained by reaction of 6-[[4-amino-3-(phenylamino)phenyl]oxy]hexanoic acid methyl ester with 3-fluorobenzoyl chloride according to general operating instructions 5.

MS (EI): 432 (molecular ion peak)

EXAMPLE 192

6-[[2-(4-Bromophenyl)-1-phenyl-1H-benzimidazol-6-yl]oxy]hexanoic acid methyl ester was obtained by reaction of 6-[[4-amino-3-(phenylamino)phenyl]oxy]hexanoic acid methyl ester with 4-bromobenzoyl chloride according to general operating instructions 5.

MS (EI): 492/494 (molecular ion peaks)

EXAMPLE 193

6-[[2-[4-(Trifluoromethyl)phenyl]-1-phenyl-3-1H-benzimidazol-6-yl]oxy]hexanoic acid methyl ester was obtained by reaction of 6-[[4-amino-3-(phenylamino)phenyl]oxy]hexanoic acid methyl ester with 4-(trifluoromethyl)benzoyl chloride according to general operating instructions 5.

MS (EI): 482 (molecular ion peak)

EXAMPLE 194

6-[[2-(4-Fluorophenyl)-1-phenyl-1H-benzimidazol-6-yl]oxy]hexanoic acid was obtained by reaction of 6-[2-(4-fluorophenyl)-1-phenyl-1H-benzimidazol-6-yl]oxy]hexanoic acid methyl ester according to general operating instructions 9.

MS (EI): 418 (molecular ion peak).

EXAMPLE 195

6-[[1-Phenyl-2-(benzothien-2-yl)-1H-benzimidazol-6-yl]oxy]hexanoic acid methyl ester was obtained by reaction of 6-[[4-amino-3-(phenylamino)phenyl]oxy]hexanoic acid methyl ester with benzothiophene-2-carboxylic acid chloride according to general operating instructions 5.

Flash point 129-130° C.

EXAMPLE 196

6-[[1-Phenyl-2-(benzothien-2-yl)-1H-benzimidazol-6-yl]oxy]hexanoic acid was produced according to general operating instructions 9.

Flash point 340° C. (decomposition)

EXAMPLE 197

6-[[5-Hydroxy-1-(4-methylphenyl)-2-phenyl-3H-benzimidazol-6-yl]oxy]hexanoic acid isopropyl ester

EXAMPLE 198

6-[[6-Hydroxy-1-(4-methylphenyl)-2-phenyl-1H-benzimidazol-5-yl]oxy]hexanoic acid isopropyl ester 4,5-Dimethoxy-1,2-dinitrobenzene was hydrogenated to the diamino compound according to general operating instructions 1, and said compound was cyclized with trimethyl orthobenzoate to 5,6-dimethoxy-2-phenyl-1H-benzimidazole (flash point 131-133° C.) as crude product according to general operating instructions 3. This benzimidazole derivative was reacted with 4-methylphenylboronic acid to 5,6-dimethoxy-1-(4-methylphenyl)-2-phenyl-1H-benzimidazole (flash point 145-148° C.) according to general operating instructions 14. After ether cleavage with hydrobromic acid according to general operating instructions 6 to 5,6-dihydroxy-1-(4-methylphenyl)-2-phenyl-1H-benzimidazole ($^1$H-NMR of hydrobromide (D$_6$-DMSO): δ=2.42 ppm s (3H); 6.68 s (1H); 7.22 s (1H); 7.40-7.62 m (10H)), it was alkylated with 6-bromohexanoic acid isopropyl ester according to general operating instructions 8. 6-[[5-Hydroxy-1-(4-methylphenyl)-2-phenyl-1H-benzimidazol-6-yl]oxy]hexanoic acid isopropyl ester flash point 137-139° C.

and 6-[[6-hydroxy-1-(4-methylphenyl)-2-phenyl-1H-benzimidazol-5-yl]oxy]hexanoic acid isopropyl ester flash point 177-178° C.

were obtained.

EXAMPLE 199

6-[[5-Hydroxy-1-(4-methylphenyl)-2-phenyl-1H-benzimidazol-6-yl]oxy]hexanoic acid was produced according to general operating instructions 9.

Flash point 245-248° C.

EXAMPLE 200

6-[[6-Hydroxy-1-(4-methylphenyl)-2-phenyl-1H-benzimidazol-5-yl]oxy]hexanoic acid was produced according to general operating instructions 9.
Flash point 182-184° C.

EXAMPLE 201

6-[[5-Methoxy-1-(4-methylphenyl)-2-phenyl-1H-benzimidazol-6-yl]oxy]hexanoic acid isopropyl ester 6-[[5-Hydroxy-1-(4-methylphenyl)-2-phenyl-1H-benzimidazol-6-yl]oxy]hexanoic acid isopropyl ester was methylated with methyl iodide according to general operating instructions 8.
Flash point 89-91° C.

EXAMPLE 202

6-[[5-Methoxy-1-(4-methylphenyl)-2-phenyl-1H-benzimidazol-6-yl]oxy]hexanoic acid was produced according to general operating instructions 9.
Flash point 184-186° C.

EXAMPLE 203

6-[[5-Hydroxy-1-(4-methylphenyl)-2-phenyl-1H-benzimidazol-6-yl]oxy]hexanoic acid methyl ester
and

EXAMPLE 204

6-[[6-Hydroxy-1-(4-methylphenyl)-2-phenyl-1H-benzimidazol-5-yl]oxy]-hexanoic acid methyl ester were produced with 6-bromohexanoic acid methyl ester analogously to the isopropyl esters by alkylation of 5,6-dihydroxy-1-(4-methylphenyl)-2-phenyl-1H-benzimidazole according to general operating instructions 8. 6-[[5-Hydroxy-1-(4-methylphenyl)-2-phenyl-1H-benzimidazol-6-yl]oxy]hexanoic acid methyl ester was obtained.
$^1$H-NMR (CDCl$_3$): δ=1.45-1.58 ppm m (2H); 1.65-1.90 m (4H); 2.37 t (J=7.5 Hz, 2H); 2.48 s (3H); 3.68 s (3H); 3.98 t (J=7.5 Hz, 2H); 5.68 s (broad) (1H, OH); 6.62 s (1H); 7.18 d (J=8 Hz, 2H); 7.22-7.38 m (5H); 7.40 s (1H); 7.53 dd (J=8, 1 Hz, 2H) and 6-[[6-hydroxy-1-(4-methylphenyl)-2-phenyl-1H-benzimidazol-5-yl]oxy]hexanoic acid methyl ester.
Flash point 141-143° C.

EXAMPLE 205

6-[[5-Methoxy-1-(4-methylphenyl)-2-phenyl-3H-benzimidazol-6-yl]oxy]hexanoic acid methyl ester 40 mg of 6-[[5-methoxy-1-(4-methylphenyl)-2-phenyl-1H-benzimidazol-6-yl]oxy]hexanoic acid was dissolved in 2 ml of methanol, mixed with 1 drop of concentrated sulfuric acid, and the mixture was stirred for 2 hours. It was mixed with saturated potassium bicarbonate solution, diluted with water, extracted with ethyl acetate, the extracts were dried on sodium sulfate and concentrated by evaporation in a vacuum. The residue was crystallized from diisopropyl ether.
Flash point 81-82° C.

EXAMPLE 206

6-[[6-Methoxy-1-(4-methylphenyl)-2-phenyl-1H-benzimidazol-5-yl]oxy]-hexanoic acid methyl ester 6-[[6-Hydroxy-1-(4-methylphenyl)-2-phenyl-1H-benzimidazol-5-yl]oxy]hexanoic acid methyl ester was methylated with methyl iodide according to general operating instructions 8.
Flash point 108-110° C.

EXAMPLE 207

6-[[6-Methoxy-1-(4-methylphenyl)-2-phenyl-1H-benzimidazol-5-yl]oxy]hexanoic acid was produced according to general operating instructions 9.
Flash point 182-184° C.

EXAMPLE 208

6-[(5-Amino-1-(3,4-dimethylphenyl)-2-phenyl-1H-benzimidazol-6-yl)oxy]-hexanoic acid methyl ester a) 3-[(3,4-Dimethylphenyl)amino]-4,6-dinitrophenol 6.6 g of 3,4-dimethylaniline was added to a suspension that consists of 4 g of 4,6-dinitro-3-fluorophenol (J. Org. Chem. 1991, 5958) in 100 ml of ethanol, and it was stirred for 7 days at 40° C. After cooling, it was suctioned off, and the residue was recrystallized from ethanol.
$^1$H-NMR (CDCl$_3$): δ=2.20 ppm s (6H); 6.43 s (1H); 6.90-7.0 m (2H); 7.14 d (J=8 Hz, 1H); 9.08 s (1H), 9.70 s (broad) (1H); 10.2-10.6 (1H)

b) 6-[[3-[(3,4-Dimethylphenyl)amino]-4,6-dinitrophenyl]oxy]hexanoic acid methyl ester 5 g of 3-[(3,4-dimethylphenyl)amino]-4,6-dinitrophenol was O-alkylated with 6-bromohexanoic acid methyl ester at 70° C. analogously to general operating instructions 8.
$^1$H-NMR (CDCl$_3$): δ=1.45-1.88 ppm m (6H); 2.30 s (6H); 2.33 t (J=7.5 Hz, 2H); 3.68 s (3H); 3.88 t (J=7.5 Hz, 2H); 6.45 s (1H); 7.00-7.08 m (2H); 7.25 d (J=8 Hz, 1H); 9.03 s (1H); 9.89 s (broad) (1H)

c) 6-[(5-Amino-1-(3,4-dimethylphenyl)-2-phenyl-1H-benzimidazol-6-yl)oxy]hexanoic acid methyl ester 2.45 g of 6-[[3-[(3,4-dimethylphenyl)amino]-4,6-dinitrophenyl]oxy]hexanoic acid methyl ester was hydrogenated in methanol according to general operating instructions 1. 500 mg of the crude product was reacted with benzimidate hydrochloride according to general operating instructions 4. Contrary to general operating instructions 4, after being taken up in solvent, the crude product was not washed with aqueous hydrochloric acid.
$^1$H-NMR (CDCl$_3$): δ=1.48-1.58 ppm m (2H); 1.62-1.78 m (2H); 1.78-1.90 m (2H); 2.30 s (3H); 2.38 s (3H); 2.38 t (J=7.5 Hz, 2H); 3.67 s (3H); 3.93 t (J=7.5 Hz, 2H); 6.56 s (1H); 6.98-7.08 m (2H); 7.18 s (1H); 7.20-7.32 m (4H); 7.52 dd (J=8 Hz and 2 Hz, 2H)

EXAMPLE 209

6-[[5-[[(4-Chlorophenyl)sulfonyl]amino]-1-(3,4-dimethylphenyl)-2-phenyl-1H-benzimidazol-6-yl]oxy]hexanoic acid methyl ester 6-[(5-Amino-1-(3,4-dimethylphenyl)-2-phenyl-1H-benzimidazol-6-yl)oxy]hexanoic acid methyl ester was reacted with 4-chlorobenzenesulfonic acid chloride according to general operating instructions 13.

Flash point 186-191° C.

EXAMPLE 210

6-[(5-Amino-2-(4-fluorophenyl)-1-(4-methoxyphenyl)-1H-benzimidazol-6-yl)oxy]hexanoic acid methyl ester was produced analogously to 6-[(5-amino-1-(3,4-dimethylphenyl)-2-phenyl-1H-benzimidazol-6-yl)oxy]-hexanoic acid methyl ester.

MS (EI): 4.77 (molecular ion peak)

EXAMPLE 211

6-[(5-Amino-1-(4-methoxyphenyl)-2-(4-methoxyphenyl)-1H-benzimidazol-6-yl)oxy]-hexanoic acid methyl ester was produced analogously to 6-[(5-amino-1-(3,4-dimethylphenyl)-2-phenyl-1H-benzimidazol-6-yl)oxy]-hexanoic acid methyl ester.

MS (EI): 489 (molecular ion peak)

EXAMPLE 212

6-[[5-[[(4-Chlorophenyl)sulfonyl]amino]-2-(4-fluorophenyl)-1-(4-methoxyphenyl)-1H-benzimidazol-6-yl]oxy]hexanoic acid methyl ester 6-[(5-Amino-2-(4-fluorophenyl)-1-(4-methoxyphenyl)-1H-benzimidazol-6-yl)oxy]hexanoic acid methyl ester was reacted with 4-chlorobenzenesulfonic acid chloride according to general operating instructions 13.

Flash point 180-182° C.

EXAMPLE 213

6-[[5-[[(4-Chlorophenyl)sulfonyl]amino]-1-(4-methoxyphenyl)-2-(4-methoxyphenyl)-1H-benzimidazol-6-yl]oxy]hexanoic acid methyl ester 6-[(5-Amino-1-(4-methoxyphenyl)-2-(4-methoxyphenyl)-1H-benzimidazol-6-yl)oxy]hexanoic acid methyl ester was reacted with 4-chlorobenzenesulfonic acid chloride according to general operating instructions 13.

Flash point 169-171° C.

EXAMPLE 214

4-[(5-Amino-1-(4-methoxyphenyl)-2-phenyl-1H-benzimidazol-6-yl)oxy]butanoic acid methyl ester was produced analogously to 6-[(5-amino-1-(3,4-dimethylphenyl)-2-phenyl-1H-benzimidazol-6-yl)oxy]-hexanoic acid methyl ester.

$^1$H-NMR (CDCl$_3$): δ=2.17 ppm tt (J=8 and 8 Hz, 2H); 2.52 t (J=8 Hz, 2H); 3.68 s (3H); 3.90 s (3H); 3.98 t (J=7.5 Hz, 2H); 6.54 s (1H); 7.0 d (J=12 Hz, 2H); 7.18-7.35 m (6H); 7.50-7.58 m (2H)

EXAMPLE 215

4-[[5-[[(4-Chlorophenyl)sulfonyl]amino]-1-(4-methoxyphenyl)-2-phenyl-1H-benzimidazol-6-yl]oxy]butanoic acid methyl ester 4-[(5-Amino-1-(4-methoxyphenyl)-2-phenyl-1H-benzimidazol-6-yl)oxy]butanoic acid methyl ester was reacted with 4-chlorobenzenesulfonic acid chloride according to general operating instructions 13.

MS (EI): 605 (molecular ion peak)

EXAMPLE 216

5-[(5-Amino-1-(4-methoxyphenyl)-2-phenyl-1H-benzimidazol-6-yl)oxy]pentanoic acid methyl ester was produced analogously to 6-[(5-amino-1-(3,4-dimethylphenyl)-2-phenyl-1H-benzimidazol-6-yl)oxy]-hexanoic acid methyl ester.

$^1$H-NMR (CDCl$_3$): δ=1.78-1.89 ppm m (4H); 2.32 t (J=8 Hz, 2H); 3.68 s (3H); 3.88 s (3H); 3.92 t (J=7.5 Hz, 2H); 6.53 s (1H); 7.0 d (J=12 Hz, 2H); 7.18-7.36 m (6H); 7.48-7.58 m (2H)

EXAMPLE 217

5-[[5-[[(4-Chlorophenyl)sulfonyl]-amino]-1-(4-methoxyphenyl)-2-phenyl-1H-benzimidazol-6-yl]oxy]pentanoic acid methyl ester 5-[(5-Amino-1-(4-methoxyphenyl)-2-phenyl-1H-benzimidazol-6-yl)oxy]pentanoic acid methyl ester was reacted with 4-chlorobenzenesulfonic acid chloride according to general operating instructions 13.

MS (EI): 619 (molecular ion peak)

EXAMPLE 218

6-[(5-Amino-1-(4-methoxyphenyl)-2-phenyl-1H-benzimidazol-6-yl)oxy]hexanoic acid methyl ester was produced analogously to 6-[(5-amino-1-(3,4-dimethylphenyl)-2-phenyl-1H-benzimidazol-6-yl)oxy]-hexanoic acid methyl ester.

Flash point 129-131° C.

EXAMPLE 219

6-[[5-[[(4-Chlorophenyl)sulfonyl]amino]-1-(4-methoxyphenyl)-2-phenyl-1H-benzimidazol-6-yl]oxy]hexanoic acid methyl ester 6-[(5-Amino-1-(4-methoxyphenyl)-2-phenyl-1H-benzimidazol-6-yl)oxy]hexanoic acid methyl ester was reacted with 4-chlorobenzenesulfonic acid chloride according to general operating instructions 13.
Flash point 168-170° C.

EXAMPLE 220

6-[[5-[[(4-Chlorophenyl)sulfonyl]amino]-1-(4-methoxyphenyl)-2-phenyl-1H-benzimidazol-6-yl]oxy]hexanoic acid was produced according to general operating instructions 9.
Flash point 181-182° C.

EXAMPLE 221

6-[(5-Amino-1-(4-methylphenyl)-2-phenyl-1H-benzimidazol-6-yl)oxy]hexanoic acid methyl ester was produced analogously to 6-[(5-amino-1-(3,4-dimethylphenyl)-2-phenyl-1H-benzimidazol-6-yl)oxy]-hexanoic acid methyl ester.
Flash point 105-107° C.

EXAMPLE 222

6-[[5-[[(4-Chlorophenyl)sulfonyl]amino]-1-(4-methylphenyl)-2-phenyl-1H-benzimidazol-6-yl]oxy]hexanoic acid methyl ester 6-[(5-Amino-1-(4-methylphenyl)-2-phenyl-1H-benzimidazol-6-yl)oxy]hexanoic acid methyl ester was reacted with 4-chlorobenzenesulfonic acid chloride according to general operating instructions 13.
Flash point 189-191° C.

EXAMPLE 223

6-[[5-[[(4-Chlorophenyl)sulfonyl]amino]-1-(4-methylphenyl)-2-phenyl-1H-benzimidazol-6-yl]oxy]hexanoic acid was produced according to general operating instructions 9.
Flash point 102-105° C.

EXAMPLE 224

5-[(5-Amino-1,2-diphenyl-1H-benzimidazol-6-yl)oxy]pentanoic acid methyl ester was produced analogously to 6-[(5-amino-1-(3,4-dimethylphenyl)-2-phenyl-1H-benzimidazol-6-yl)oxy]-hexanoic acid methyl ester.
$^1$H-NMR (CDCl$_3$): δ=1.82-1.95 ppm m (4H); 2.39 t (J=8 Hz, 2H); 3.69 s (3H); 3.92-4.00 m (2H); 6.60 s (1H); 7.26-7.34 m (6H); 7.43-7.58 m (5H)

EXAMPLE 225

5-[[5-[[(4-Chlorophenyl)sulfonyl]amino]-1,2-diphenyl-1H-benzimidazol-6-yl]oxy]pentanoic acid methyl ester 5-[(5-Amino-1,2-diphenyl-1H-benzimidazol-6-yl)oxy]pentanoic acid methyl ester was reacted with 4-chlorobenzenesulfonic acid chloride according to general operating instructions 13.
Flash point 157-161° C.

EXAMPLE 226

5-[[5-[[(4-Chlorophenyl)sulfonyl]amino]-1,2-diphenyl-1H-benzimidazol-6-yl]oxy]pentanoic acid was produced according to general operating instructions 9.
Flash point 236-242° C.

EXAMPLE 227

6-[[5-[[(4-Fluorophenyl)sulfonyl]amino]-1-(4-methoxyphenyl)-2-phenyl-1H-benzimidazol-6-yl]oxy]hexanoic acid methyl ester 6-[(5-Amino-1-(4-methoxyphenyl)-2-phenyl-1H-benzimidazol-6-yl)oxy]hexanoic acid methyl ester was reacted with 4-fluorobenzenesulfonic acid chloride according to general operating instructions 13.
MS (EI): 617 (molecular ion peak)

EXAMPLE 228

6-[[5-[[(4-(Trifluoromethyl)phenyl)sulfonyl]amino]-1-(4-methoxyphenyl)-2-phenyl-1H-benzimidazol-6-yl]oxy]hexanoic acid methyl ester 6-[(5-Amino-1-(4-methoxyphenyl)-2-phenyl-1H-benzimidazol-6-yl)oxy]hexanoic acid methyl ester was reacted with 4-(trifluoromethyl)benzenesulfonic acid chloride according to general operating instructions 13.
MS (EI): 668 (molecular ion peak)

EXAMPLE 229

6-[[5-[[(4-Trifluorophenyl)sulfonyl]amino]-1-(4-methoxyphenyl)-2-phenyl-1H-benzimidazol-6-yl]oxy]hexanoic acid was produced according to general operating instructions 9.
Flash point 190-192° C.

EXAMPLE 230

6-[[5-[[(4-chlorophenyl)sulfonyl]methylamino]-1-(4-methoxyphenyl)-2-phenyl-1H-benzimidazol-6-yl]oxy]hexanoic acid methyl ester 100 mg of 6-[[5-[[(4-chlorophenyl)sulfonyl]amino]-1-(4-methoxyphenyl)-2-phenyl-1H-benzimidazol-6-yl]oxy]hexanoic acid methyl ester was dissolved in 3 ml of tetrahydrofuran. 10 mg of sodium hydride was added to it at 0° C., it was allowed to stir for 30 minutes, then 50 μl of methyl iodide was added in drops, and it was allowed to stir for another 60 minutes at 0° C. It was mixed with saturated ammonium chloride solution, extracted three times with ethyl acetate, the organic phases were washed with water, dried on sodium sulfate and concentrated by evaporation in a vacuum. The residue was chromatographed on silica gel.
Flash point 178-180° C.

EXAMPLE 231

[[(4-Chlorophenyl)sulfonyl][1,2-diphenyl-1H-benzimidazol-5-yl]amino]acetic acid methyl ester 100 mg of 4-chloro-N-(1,2-diphenyl-1H-benzimidazol-5-yl)benzenesulfonamide was suspended in 0.5 ml of N,N-dimethylformamide, mixed with 8 mg of sodium hydride and stirred for 30 minutes at 20° C. 50 mg of bromoacetic acid methyl ester was added, allowed to stir for 15 hours, mixed with water, extracted three times with ethyl acetate, the extracts were dried on sodium sulfate, concentrated by evaporation in a vacuum, and the residue was chromatographed on silica gel.
$^1$H-NMR (CDCl$_3$): δ=3.70 ppm s (3H); 4.52 s (2H); 7.20 d (J=8 Hz, 1H); 7.26-7.58 m (14H); 7.70 d (J=10 Hz, 2H)

EXAMPLE 232

[[(4-Chlorophenyl)sulfonyl][1,2-diphenyl-1H-benzimidazol-5-yl]amino]acetic acid was produced according to general operating instructions 9.
Flash point 248° C.

EXAMPLE 233

4-[[(4-Chlorophenyl)sulfonyl][1,2-diphenyl-1H-benzimidazol-5-yl]amino]butanoic acid methyl ester 100 mg of 4-chloro-N-(1,2-diphenyl-1H-benzimidazol-5-yl)benzenesulfonamide was suspended in 0.5 ml of N,N-dimethylformamide, mixed with 6 mg of sodium hydride and stirred for 30 minutes at 20° C. 56 mg of 4-bromobutyric acid methyl ester was added, it was allowed to stir for 15 hours, mixed with water, extracted three times with ethyl acetate, the extracts were dried on sodium sulfate, concentrated by evaporation in a vacuum, and the residue was digested with diisopropyl ether.
Flash point 54-58° C.

EXAMPLE 234

4-[[(4-Chlorophenyl)sulfonyl][1,2-diphenyl-1H-benzimidazol-5-yl]amino]butanoic acid was produced according to general operating instructions 9.
Flash point 249-254° C.

EXAMPLE 235

5-[[(4-Chlorophenyl)sulfonyl][1,2-diphenyl-1H-benzimidazol-5-yl]amino]pentanoic acid methyl ester 100 mg of 4-chloro-N-(1,2-diphenyl-1H-benzimidazol-5-yl)benzenesulfonamide was suspended in 0.5 ml of N,N-dimethylformamide, mixed with 8 mg of sodium hydride and stirred for 30 minutes at 20° C. 60 mg of 5-bromopentanoic acid methyl ester was added, it was allowed to stir for 15 hours, mixed with water, extracted three times with ethyl acetate, the extracts were dried on sodium sulfate, concentrated by evaporation in a vacuum, and the residue was chromatographed on silica gel.
$^1$H-NMR (CDCl$_3$): δ=1.46-1.54 ppm m (2H); 1.62-1.78 m (2H); 2.30 t (J=8 Hz, 2H); 3.62 s (3H); 3.62 t (J=8 Hz, 2H); 7.12-7.53 m (17H)

EXAMPLE 236

5-[[(4-Chlorophenyl)sulfonyl][1,2-diphenyl-1H-benzimidazol-5-yl]amino]pentanoic acid was produced according to general operating instructions 9.
Flash point 123-127° C.

EXAMPLE 237

6-[[(4-Chlorophenyl)sulfonyl][1,2-diphenyl-1H-benzimidazol-5-yl]amino]hexanoic-acid methyl ester 6-[[1,2-Diphenyl-1H-benzimidazol-5-yl]amino]hexanoic acid methyl ester was reacted with 4-chlorobenzenesulfonic acid chloride according to general operating instructions 13.
MS (EI): 588 (molecular ion peak)

EXAMPLE 238

7-[[(4-Chlorophenyl)sulfonyl][1,2-diphenyl-1H-benzimidazol-5-yl]amino]heptanoic acid methyl ester 100 mg of 4-chloro-N-(1,2-diphenyl-1H-benzimidazol-5-yl)benzenesulfonamide was suspended in 0.5 ml of N,N-dimethylformamide, mixed with 8 mg of sodium hydride, and stirred for 30 minutes at 20° C. 70 mg of 7-bromoheptanoic acid methyl ester was added, it was allowed to stir for 15 hours, mixed with water, extracted three times with ethyl acetate, the extracts were dried on sodium sulfate, concentrated by evaporation in a vacuum, and the residue was chromatographed on silica gel.
$^1$H-NMR (CDCl$_3$): δ=1.26-1.64 ppm m (8H); 2.27 t (J=8 Hz, 2H); 3.60 t (J=8 Hz, 2H); 3.68 s (3H); 7.12 dd (J=10, 2 Hz, 1H); 7.22 d (J=10 Hz, 1H); 7.30-7.61 m (15H)

EXAMPLE 239

7-[[(4-Chlorophenyl)sulfonyl][1,2-diphenyl-1H-benzimidazol-5-yl]amino]heptanoic acid was produced according to general operating instructions 9.
Flash point 172-178° C.

EXAMPLE 240

N-(1,2-Diphenyl-1H-benzimidazol-5-yl)-4-fluorobenzenesulfonamide

5-Amino-1,2-diphenyl-1H-benzimidazole was reacted with 4-fluorobenzenesulfonic acid chloride according to general operating instructions 13.
Flash point 209-214° C.

EXAMPLE 241

6-[[(4-Fluorophenyl)sulfonyl][1,2-diphenyl-1H-benzimidazol-5-yl]amino]hexanoic acid methyl ester 150 mg of N-(1,2-diphenyl-1H-benzimidazol-5-yl)-4-fluorobenzenesulfonamide was suspended in 0.5 ml of N,N-dimethylformamide, mixed with 12 mg of sodium hydride and stirred for 30 minutes at 20° C. 98 mg of 6-bromohexanoic acid methyl ester was added, allowed to stir for 15 hours, mixed with water, extracted three times with ethyl acetate, the extracts were dried on sodium sulfate, concentrated by evaporation in a vacuum, and the residue was chromatographed on silica gel.

Flash point 128-134° C.

EXAMPLE 242

6-[[(4-Fluorophenyl)sulfonyl][1,2-diphenyl-1H-benzimidazol-5-yl]amino]hexanoic acid was produced according to general operating instructions 9.
Flash point 200-210° C.

EXAMPLE 243

6-[[[4-(Trifluoromethyl)phenyl]sulfonyl][1,2-diphenyl-1H-benzimidazol-5-yl]-amino]hexanoic acid methyl ester 150 mg of 4-(trifluoromethyl)-N-(1,2-diphenyl-1H-benzimidazol-5-yl)benzenesulfonamide was suspended in 0.5 ml of N,N-dimethylformamide, mixed with 11 mg of sodium hydride and stirred for 30 minutes at 20° C. 88 mg of 6-bromohexanoic acid methyl ester was added, it was allowed to stir for 15 hours, mixed with water, extracted three times with ethyl acetate, the extracts were dried on sodium sulfate, concentrated by evaporation in a vacuum, and the residue was digested with diisopropyl ether.
Flash point 359-161° C.

EXAMPLE 244

6-[[[4-(Trifluoromethyl)phenyl]sulfonyl][1,2-diphenyl-1H-benzimidazol-5-yl]-amino]hexanoic acid was produced according to general operating instructions 9.
Flash point 224-230° C.

EXAMPLE 245

4-Chloro-N-[1-(4-methoxyphenyl)-2-phenyl-1H-benzimidazol-5-yl]benzenesulfonamide a) (2,4-Dinitrophenyl)(4-methoxyphenyl)amine 1.43 g of 4-(2,4-dinitroanilino)phenol, 500 mg of potassium carbonate and 0.32 ml of methyl iodide were stirred in 5 ml of N,N-dimethylformamide for 2 days at 20° C. The mixture was poured onto water, extracted three times with ethyl acetate, the extracts were dried on sodium sulfate, concentrated by evaporation in a vacuum, and the residue was chromatographed on silica gel.
Flash point 117-127° C.

b) 5-Amino-1-(4-methoxyphenyl)-2-phenyl-1H-benzimidazole (2,4-Dinitrophenyl)(4-methoxyphenyl)amine was hydrogenated according to general operating instructions 1. The crude product was cyclized with trimethyl orthobenzoate to the benzimidazole derivative according to general operating instructions 3.
$^1$H-NMR (CDCl$_3$): δ=3.88 ppm s (3H); 6.70 dd (J=12, 2 Hz, 1H); 6.95-7.06 m (4H); 7.18-7.38 m (7H); 7.53-7.65 m (2H)

c) 4-Chloro-N-[1-(4-methoxyphenyl)-2-phenyl-1H-benzimidazol-5-yl]benzenesulfonamide 5-Amino-1-(4-methoxyphenyl)-2-phenyl-1H-benzimidazole was reacted with 4-chlorobenzenesulfonic acid chloride according to general operating instructions 13.
Flash point 238-24° C.

EXAMPLE 246

6-[[(4-Chlorophenyl)sulfonyl][1-(4-methoxyphenyl)-2-phenyl-1H-benzimidazol-5-yl]amino]hexanoic acid methyl ester 75 mg of 4-chloro-N-[1-(4-methoxyphenyl)-2-phenyl-1H-benzimidazol-5-yl]benzenesulfonamide was suspended in 0.5 ml of N,N-dimethylformamide, mixed with 6 mg of sodium hydride and stirred for 30 minutes at 20° C. 44 mg of 6-bromohexanoic acid methyl ester was added, allowed to stir for 15 hours, mixed with water, extracted three times with ethyl acetate, the extracts were dried on sodium sulfate, concentrated by evaporation in a vacuum, and the residue was chromatographed on silica gel.
MS (EI): 617 (molecular ion peak)

EXAMPLE 247

6-[[(4-Chlorophenyl)sulfonyl][1-(4-methoxyphenyl)-2-phenyl-1H-benzimidazol-5-yl]amino]hexanoic acid was produced according to general operating instructions 9.
Flash point 205-208° C.

EXAMPLE 248

2,2-Dimethyl-6-[(1,2-diphenyl-1H-benzimidazol-6-yl)oxy]hexanamide a) 2,2-Dimethyl-6-[(1,2-diphenyl-1H-benzimidazol-6-yl)oxy]hexanonitrile was obtained by reaction of 1,2-diphenyl-6-hydroxy-1H-benzimidazole with 6-bromo-1,1-dimethylhexanonitrile according to general operating instructions 8.
Flash point 115-118° C.

b) 2,2-Dimethyl-6-[(1,2-diphenyl-1H-benzimidazol-6-yl)oxy]hexanamide 500 mg of 2,2-dimethyl-6-[(1,2-diphenyl-1H-benzimidazol-6-yl)oxy]hexanonitrile was refluxed for 2 hours in 5 ml of 80% sulfuric acid. After cooling, it was carefully added to ice water, the pH was set at 8 with sodium hydroxide solution, it was extracted three times with ethyl acetate, the extracts were dried on sodium sulfate, and it was concentrated by evaporation in a vacuum. The residue was chromatographed on silica gel.
Flash point 115-118° C.

EXAMPLE 249

8-[(1,2-Diphenyl-1H-benzimidazol-6-yl)oxy]octanoic acid methyl ester was obtained by reaction of 1,2-diphenyl-6-hydroxy-1H-benzimidazole with 8-bromooctanoic acid methyl ester according to general operating instructions 8.
Flash point 92-95° C.

EXAMPLE 250

8-[(1,2-Diphenyl-1H-benzimidazol-6-yl)oxy]octanoic acid was produced according to general operating instructions 9.
Flash point 136-140° C.

EXAMPLE 251

6-[[1-(Indan-5-yl)-2-phenyl-1H-benzimidazol-6-yl]oxy]hexanoic acid methyl ester was produced analogously to 6-[[1-(3,4-dimethylphenyl)-2-phenyl-1H-benzimidazol-6-yl]oxy]hexanoic acid methyl ester.
Flash point 81-85° C.

EXAMPLE 252

6-[[1-(Indan-5-yl)-2-phenyl-1H-benzimidazol-6-yl]oxy]hexanoic acid was produced according to general operating instructions 9.
Flash point 176-180° C.

EXAMPLE 253

7-[[1-(Indan-5-yl)-2-phenyl-1H-benzimidazol-6-yl]oxy]heptanoic acid methyl ester was produced analogously to 6-[[1-(3,4-dimethylphenyl)-2-phenyl-1H-benzimidazol-6-yl]oxy]hexanoic acid methyl ester.
Flash point 92-98° C.

EXAMPLE 254

7-[[1-(Indan-5-yl)-2-phenyl-1H-benzimidazol-6-yl]oxy]heptanoic acid was produced according to general operating instructions 9.
Flash point 175-178° C.

EXAMPLE 255

6-[[1-(3-Fluorophenyl)-2-phenyl-1H-benzimidazol-6-yl]oxy]hexanoic acid methyl ester was produced-analogously to 6-[[1-(3,4-dimethylphenyl)-2-phenyl-1H-benzimidazol-6-yl]oxy]hexanoic acid methyl ester.
Flash point 104-106° C.

EXAMPLE 256

6-[[1-(3-Fluorophenyl)-2-phenyl-1H-benzimidazol-6-yl]oxy]hexanoic acid was produced according to general operating instructions 9.
Flash point 149-151° C.

EXAMPLE 257

6-[[2-(4-Nitrophenyl)-1-phenyl-1H-benzimidazol-6-yl]oxy]hexanoic acid methyl ester a) 6-Methoxy-2-(4-nitrophenyl)-1-phenyl-1H-benzimidazole 200 mg of 4-methoxy-$N^2$-phenyl-o-phenylenediamine was dissolved in 5 ml of N,N-dimethylformamide, mixed with 346 mg of EEDQ and 234 mg of 4-nitrobenzoic acid, and the mixture was stirred for 5 hours at 100° C. After cooling, it was mixed with water. The precipitate was suctioned off and purified by column chromatography, taken up in 6N hydrochloric acid and refluxed for 2 hours. After cooling, it was added in drops to saturated potassium bicarbonate solution. The precipitate was suctioned off and dried.
Flash point 189-191° C.

b) 6-Hydroxy-2-(4-nitrophenyl)-1-phenyl-1H-benzimidazole was obtained by reaction according to general operating instructions 6.
$^1$H-NMR ($D_6$-DMSO): δ=6.56 ppm d (J=2 Hz, 1H); 6.87 dd (J=10, 2 Hz, 1H); 7.46 dd (J=10, 2 Hz, 2H); 7.53-7.70 m (4H); 7.75 d (J=10 Hz, 2H); 8.20 d (J=10 Hz, 2H); 9.55 s (broad) (1H)

c) 6-[[2-(4-Nitrophenyl)-1-phenyl-1H-benzimidazol-6-yl]oxy]hexanoic acid methyl ester was obtained by reaction according to general operating instructions 8.
$^1$H-NMR (CDCl$_3$): δ=1.45-1.55 ppm m (2H); 1.62-1.84 m (4H); 2.33 t (J=8 Hz, 2H); 3.68 s (3H); 3.95 t (J=8 Hz, 2H); 6.67 d (J=2 Hz, 1H); 7.00 dd (J=10, 2 Hz, 1H); 7.28-7.38 m (2H); 7.52-7.60 m (3H); 7.71 d (J=10 Hz, 2H); 7.77 d (J=10 Hz, 1H); 8.13 d (J=10 Hz, 2H)

EXAMPLE 258

6-[[2-(4-Nitrophenyl)-1-phenyl-1H-benzimidazol-6-yl]oxy]hexanoic acid was produced according to general operating instructions 9.
Flash point 181-186° C.

EXAMPLE 259

6-[[1-Phenyl-2-(3-pyridinyl)-1H-benzimidazol-6-yl]oxy]hexanoic acid methyl ester was produced analogously to 6-[[1-phenyl-2-(4-pyridinyl)-1H-benzimidazol-6-yl]oxy]hexanoic acid methyl ester.
Flash point 159-160° C.

EXAMPLE 260

N-(Cyclopropylmethoxy)-6-[(1,2-diphenyl-1H-benzimidazol-6-yl)oxy]hexanamide was produced according to general operating instructions 18.
MS (EI): 469 (molecular ion peak)

EXAMPLE 261

N-Isobutoxy-6-[(1,2-diphenyl-1H-benzimidazol-6-yl)oxy]hexanamide was produced according to general operating instructions 18.

MS (EI): 471 (molecular ion peak)

EXAMPLE 262

N-(Phenylmethoxy)-6-[2-phenyl-1-(3,4,5-trimethoxyphenyl)-1H-benzimidazol-6-yl)oxy]-hexanamide A solution that consists of 50 mg of 6-[2-phenyl-1-(3,4,5-trimethoxyphenyl)-1H-benzimidazol-6-yl)oxy]hexanoic acid in 1 ml of tetrahydrofuran was added to a solution that consists of 17 mg of carbonyl diimidazole in 1 ml of tetrahydrofuran, it was stirred for 30 minutes at 20° C. and refluxed for 30 minutes. At 20° C., 16 mg of O-benzylhydroxylamine hydrochloride was added, and it was allowed to stir for 20 hours. For working-up, ethyl acetate was added, extracted with 2N hydrochloric acid and saturated sodium bicarbonate solution, dried on sodium sulfate and concentrated by evaporation in a vacuum. The residue was purified by column chromatography on silica gel.

Flash point 145-148° C.

EXAMPLE 263

N-(Cyclopropylmethoxy)-6-[2-phenyl-1-(3,4,5-trimethoxyphenyl)-1H-benzimidazol-6-yl)oxy]hexanamide was produced analogously to N-(phenylmethoxy)-6-[2-phenyl-1-(3,4,5-trimethoxyphenyl)-1H-benzimidazol-6-yl)oxy]hexanamide.

MS (EI): 559 (molecular ion peak)

EXAMPLE 264

N-Isobutoxy-6-[2-phenyl-1-(3,4,5-trimethoxyphenyl)-1H-benzimidazol-6-yl)oxy]hexanamide was produced analogously to N-(phenylmethoxy)-6-[2-phenyl-1-(3,4,5-trimethoxyphenyl)-1H-benzimidazol-6-yl)oxy]hexanamide.

$^1$H-NMR (CDCl$_3$): δ=0.94 ppm d (J=8 Hz, 6H); 1.48-2.03 m (7H); 2.05-2.18 m (2H); 3.60-3.72 m (2H); 3.76 s (6H); 3.90-4.00 m (2H); 3.96 s (3H); 6.50 s (2H); 6.72 d (J=2 Hz, 1H); 6.95 dd (J=10, 2 Hz, 1H); 7.28-7.38 m (3H); 7.55-7.62 m (2H); 7.74 d (J=10 Hz, 1H); 8.20 s (broad) (1H).

EXAMPLE 265

N-Isopropyl-6-[(1,2-diphenyl-1H-benzimidazol-6-yl)oxy]hexanamide was produced according to general operating instructions 17.

Flash point 107-112° C.

EXAMPLE 266

N,N-Dimethyl-6-[(1,2-diphenyl-1H-benzimidazol-6-yl)oxy]hexanamide was produced according to general operating instructions 17.

Flash point 83-88° C.

EXAMPLE 267

6-[(1,2-Diphenyl-1H-benzimidazol-6-yl)oxy]-1-pyrrolidin-1-ylhexan-1-one was produced according to general operating instructions 17.

Flash point 84-88° C.

EXAMPLE 268

N-(2-Methoxyethyl)-6-[(1,2-diphenyl-1H-benzimidazol-6-yl)oxy]hexanamide was produced according to general operating instructions 17.

Flash point 63-68° C.

EXAMPLE 269

N-(3-Methoxypropyl)-6-[(1,2-diphenyl-1H-benzimidazol-6-yl)oxy]hexanamide was produced according to general operating instructions 18.

Flash point 84-91° C.

EXAMPLE 270

N-Isobutyl-6-[(1,2-diphenyl-1H-benzimidazol-6-yl)oxy]hexanamide was produced according to general operating instructions 17.

$^1$H-NMR (CDCl$_3$): δ=0.90 ppm d (J=8 Hz, 6H); 1.44-1.57 m (2H); 1.65-1.85 m (5H); 2.20 t (J=8 Hz, 2H); 3.08 t (J=8 Hz, 2H); 3.94 t (J=8 Hz, 2H); 6.68 d (J=2 Hz, 1H); 6.96 dd (J=10, 2 Hz, 1H); 7.25-7.38 m (5H); 7.45-7.58 m (5H); 7.75 d (J=10 Hz, 1H)

EXAMPLE 271

N-[[2,2-Dimethylamino)ethyl]-N-methyl-6-[(1,2-diphenyl-1H-benzimidazol-6-yl)-oxy]hexanamide was produced according to general operating instructions 17.

$^1$H-NMR (CDCl$_3$) (signal of the main rotamer): δ=1.44-1.57 ppm m (2H); 1.64-1.84 m (4H); 2.30 s (6H); 2.34 t (J=8 Hz, 2H); 2.47 t (J=8 Hz, 2H); 3.00 s (3H); 3.50 t (J=8 Hz, 2H); 3.94 t (J=8 Hz, 2H); 6.69 d (J=2 Hz, 1H); 6.96 dd (J=10, 2 Hz, 1H); 7.25-7.36 m (5H); 7.45-7.56 m (5H); 7.73 d (J=10 Hz, 1H)

EXAMPLE 272

N-(2-Methoxyethyl)-N-methyl-6-[(1,2-diphenyl-1H-benzimidazol-6-yl)oxy]hexanamide was produced according to general operating instructions 17.

$^1$H-NMR (CDCl$_3$) (signal of the main rotamer): δ=1.43-1.58 ppm m (2H); 1.63-1.84 m (4H); 2.33 t (J=8 Hz, 2H); 3.07 s (3H); 3.32 s (3H); 3.47-3.58 m (4H); 3.95 t (J=8 Hz, 2H); 6.70 d (J=2 Hz, 1H); 6.96 dd (J=10, 2 Hz, 1H); 7.25-7.35 m (5H); 7.45-7.55 m (5H); 7.75 d (J=10 Hz, 1H)

EXAMPLE 273

6-[(1,2-Diphenyl-1H-benzimidazol-6-yl)oxy]-1-morpholin-1-ylhexan-1-one was produced according to general operating instructions 17.

$^1$H-NMR (CDCl$_3$): δ=1.47-1.59 ppm m (2H); 1.63-1.88 m (4H); 2.34 t (J=8 Hz, 2H); 3.42-3.49 m (2H); 3.57-3.70 m (6H); 3.94 t (J=8 Hz, 2H); 6.68 d (J=2 Hz, 1H); 6.96 dd (J=10, 2 Hz, 1H); 7.23-7.38 m (5H); 7.45-7.56 m (5H); 7.75 d (J=10 Hz, 1H)

EXAMPLE 274

N,N-Di(-2-methoxyethyl)-6-[(1,2-diphenyl-1H-benzimidazol-6-yl)oxy]hexanamide was produced according to general operating instructions 18.

Flash point 88-98° C.

EXAMPLE 275

N-Isopentyl-6-[(1,2-diphenyl-1H-benzimidazol-6-yl)oxy]hexanamide was produced according to general operating instructions 18.

Flash point 127-129° C.

EXAMPLE 276

N-(Pyridin-2-yl)-6-[(1,2-diphenyl-1H-benzimidazol-6-yl)oxy]hexanamide was produced according to general operating instructions 18.

Flash point 120-124° C.

EXAMPLE 277

N-(Pyridin-3-yl)-6-[(1,2-diphenyl-1H-benzimidazol-6-yl)oxy]hexanamide was produced according to general operating instructions 18.

Flash point 154° C.

EXAMPLE 278

6-[(1,2-Diphenyl-1H-benzimidazol-6-yl)oxy]-1-piperidin-1-ylhexan-1-one was produced according to general operating instructions 18.

Flash point 93-98° C.

EXAMPLE 279

[6-[(1,2-Diphenyl-1H-benzimidazol-6-yl)oxy]-1-hexanoyl]piperidine-4-carbonamide was produced according to general operating instructions 17.

Flash point 177-178° C.

EXAMPLE 280

[[6-[(1,2-Diphenyl-1H-benzimidazol-6-yl)oxy]-1-hexanoyl]methylamino]-acetic acid ethyl ester was produced according to general operating instructions 17.

$^1$H-NMR (CDCl$_3$) (signal of the main rotamer): δ=1.23 ppm t (J=8 Hz, 3H); 1.45-1.88 m (6H); 2.40 t (J=8 Hz, 2H); 3.08 s (3H); 3.93 t (J=8 Hz, 2H); 4.12 s (2H); 4.18 q (J=8 Hz; 2H); 6.70 d (J=2 Hz, 1H); 6.97 dd (J=10, 2 Hz, 1H) 7.23-7.35 m (5H); 7.45-7.58 m (5H); 7.75 d (J=10 Hz, 1H)

EXAMPLE 281

4-[[6-[(1,2-Diphenyl-1H-benzimidazol-6-yl)oxy]-1-hexanoyl]]piperazine-1-carboxylic acid ethyl ester was produced according to general operating instructions 17.

$^1$H-NMR (CDCl$_3$): δ=1.27 ppm t (J=8 Hz, 3H); 1.45-1.60 m (2H); 1.63-1.88 m (4H); 2.36 t (J=8 Hz, 2H); 3.40-3.53 m (6H); 3.56-3.64 m (2H); 3.93 t (J=8 Hz, 2H); 4.15 q (J=8 Hz, 2H); 6.69 d (J=2 Hz, 1H); 6.96 dd (J=10, 2 Hz, 1H); 7.23-7.38 m (5H); 7.45-7.56 m (5H); 7.76 d (J=10 Hz, 1H)

EXAMPLE 282

N-Isopropyl-6-[[1-(3,4-dimethylphenyl)-2-phenyl-1H-benzimidazol-6-yl]oxy]hexanamide was produced according to general operating instructions 18.

MS (EI): 469 (molecular ion peak)

EXAMPLE 283

N,N-Dimethyl-6-[[1-(3,4-dimethylphenyl)-2-phenyl-1H-benzimidazol-6-yl]oxy]-hexanamide was produced according to general operating instructions 18.

MS (EI): 455 (molecular ion peak)

EXAMPLE 284

N,N-Diethyl-6-[[1-(3,4-dimethylphenyl)-2-phenyl-1H-benzimidazol-6-yl]oxy]hexanamide was produced according to general operating instructions 18.

MS (EI): 483 (molecular ion peak)

EXAMPLE 285

N-Isobutyl-6-[[1-(3,4-dimethylphenyl)-2-phenyl-1H-benzimidazol-6-yl]oxy]hexanamide was produced according to general operating instructions 18.

$^1$H-NMR (CDCl$_3$): δ=0.90 ppm d (J=8 Hz, 6H); 1.44-1.55 m (2H); 1.58-1.83 m (5H); 2.20 t (J=8 Hz, 2H); 2.30 s (3H); 2.35 s (3H); 3.09 t (J=8 Hz, 2H); 3.94 t (J=8 Hz, 2H); 6.63 d (J=2 Hz, 1H); 6.94 dd (J=10, 2 Hz, 1H); 7.02 dd (J=10, 2 Hz, 1H); 7.10 d (J=2 Hz, 1H); 7.22-7.35 m (4H); 7.56 dd J=8 Hz, and 2 Hz, 2H); 7.73 d (J=10 Hz, 1H)

EXAMPLE 286

N-Cyclopropyl-6-[[1-(3,4-dimethylphenyl)-2-phenyl-1H-benzimidazol-6-yl]oxy]-hexanamide was produced according to general operating instructions 18.

MS (EI): 467 (molecular ion peak)

EXAMPLE 287

N-Cyclobutyl-6-[[1-(3,4-dimethylphenyl)-2-phenyl-1H-benzimidazol-6-yl]-oxy]hexanamide was produced according to general operating instructions 18.

$^1$H-NMR (CDCl$_3$): δ=1.42-1.55 ppm m (2H); 1.60-1.88 m (8H); 2.15 t (J=8 Hz, 2H); 2.28-2.40 m (2H); 2.30 s (3H); 2.35 s (3H); 3.93 t (J=8 Hz, 2H); 4.40 quintet (J=8 Hz, 2H); 5.55 s (broad) (1H); 6.63 d (J=2 Hz, 1H); 6.92 dd (J=10, 2 Hz, 1H); 7.03 dd (J=10 Hz, and 2 Hz; 1H); 7.08 d (J=2 Hz, 1H); 7.20-7.36 m (4H); 7.57 dd (J=8, 2 Hz, 2H); 7.72 d (J=10 Hz, 1H)

EXAMPLE 288

N-tert-Butyl-6-[[1-(3,4-dimethylphenyl)-2-phenyl-1H-benzimidazol-6-yl]oxy]hexanamide was produced according to general operating instructions 18.

$^1$H-NMR (CDCl$_3$): δ=1.32 ppm s (9H); 1.42-1.55 m (2H); 1.62-1.82 m (4H); 2.10 t (J=8 Hz, 2H); 2.30 s (3H); 2.36 s (3H); 3.92 t (J=8 Hz, 2H); 5.23 s (broad) (1H); 6.66 d (J=2 Hz, 1H); 6.93 dd (J=10, 2 Hz, 1H); 7.02 dd (J=10 Hz, and 2 Hz, 1H); 7.02 s (broad) (1H); 7.22-7.36 m (4H); 7.56 dd (J=8, 2 Hz, 2H); 7.73 d (J=10 Hz, 1H)

EXAMPLE 289

(R)-6-[[1-(3,4-Dimethylphenyl)-2-phenyl-1H-benzimidazol-6-yl]oxy]1-(2-methoxy-methyl)pyrrolidin-1-ylhexan-1-one was produced according to general operating instructions 18.

MS (EI): 467 (molecular ion peak)

EXAMPLE 290

N-(3-Imidazol-1-yl-propyl)-6-[[1-(3,4-dimethylphenyl)-2-phenyl-1H-benzimidazol-6-yl]oxy]hexanamide was produced according to general operating instructions 18.

$^1$H-NMR (CDCl$_3$): δ=1.42-1.53 ppm m (2H); 1.62-2.02 m (6H); 2.17 t (J=8 Hz, 2H); 2.27 s (3H); 2.34 s (3H); 3.24 q (J=8 Hz, 2H); 3.92 t (J=8 Hz, 2H); 3.96 t (J=8 Hz, 2H); 5.68 s (broad) (1H); 6.63 d (J=2 Hz, 1H); 6.88-6.95 m (2H); 7.00 dd (J=10 Hz, and 2 Hz, 1H); 7.04-7.10 m (2H); 7.20-7.36 m (4H); 7.50 s (broad) (1H); 7.53 dd (J=8, 2 Hz, 2H); 7.72 d (J=10 Hz, 1H)

EXAMPLE 291

N-(2-Pyridin-2-ylethyl)-6-[[1-(3,4-dimethylphenyl)-2-phenyl-1H-benzimidazol-6-yl]oxy]hexanamide was produced according to general operating instructions 18.

$^1$H-NMR (CDCl$_3$): δ=1.38-1.52 ppm m (2H); 1.62-1.82 m (4H); 2.15 t (J=8 Hz, 2H); 2.30 s (3H); 2.35 s (3H); 2.96 t (J=8 Hz, 2H); 3.66 q (J=8 Hz, 2H); 3.90 t (J=8 Hz, 2H); 6.48 s (broad) (1H); 6.65 d (J=2 Hz, 1H); 6.92 dd (J=10, 2 Hz, 1H); 7.00 d (J=10 Hz, and 2 Hz, 1H); 7.06-7.38 m (7H); 7.53-7.62 m (3H); 7.72 d (J=10 Hz, 1H); 8.50 d (broad) (J=6 Hz, 1H)

EXAMPLE 292

N,N-Dimethyl-6-[[2-(4-nitrophenyl)-1-phenyl-1H-benzimidazol-6-yl]oxy]hexanamide was produced according to general operating instructions 18.

$^1$H-NMR (CDCl$_3$): δ=1.46-1.58 ppm m (2H); 1.64-1.88 m (4H); 2.32 t (J=8 Hz, 2H); 2.93 s (3H); 3.00 s (3H); 3.96 t (J=8 Hz, 2H); 6.65 d (J=2 Hz, 1H); 7.00 dd (J=10, 2 Hz, 1H); 7.28-7.36 m (2H); 7.53-7.61 m (3H); 7.70 d (J=10 Hz, 2H); 7.76 d (J=8 Hz, 1H); 8.13 d (J=8 Hz, 2H)

EXAMPLE 293

N-Isopropyl-6-[[2-(4-nitrophenyl)-1-phenyl-1H-benzimidazol-6-yl]oxy]hexanamide was produced according to general operating instructions 18.

Flash point 162-165° C.

EXAMPLE 294

N-Isopentyl-6-[[2-(4-nitrophenyl)-1-phenyl-1H-benzimidazol-6-yl]oxy]hexanamide was produced according to general operating instructions 18.

Flash point 148-154° C.

EXAMPLE 295

N-(3-Methoxypropyl)-6-[[2-(4-nitrophenyl)-1-phenyl-1H-benzimidazol-6-yl]-oxy]hexanamide was produced according to general operating instructions 18.

Flash point 104-110° C.

EXAMPLE 296

N-(3-Methoxypropyl)-6-[[1-(indan-5-yl)-2-phenyl-1H-benzimidazol-6-yl]oxy]hexanamide was produced according to general operating instructions 18.

$^1$H-NMR (CDCl$_3$): δ=1.43-1.56 ppm m (2H); 1.62-1.85 m (6H); 2.10-2.23 m (4H); 2.95 t (J=10 Hz, 2H); 3.00 t (J=10 Hz, 2H); 3.32 s (3H); 3.32-3.40 m (2H); 3.48 t (J=8 Hz, 2H); 3.93 t (J=8 Hz, 2H); 6.03 s (broad) (1H); 6.67 d (J=2 Hz, 1H); 6.93 dd (j=10, 2 Hz, 1H); 7.03 dd (J=10, 2 Hz, 1H); 7.12 s (broad) (1H); 7.26-7.35 m (4H); 7.55 dd (J=10 Hz, 2H); 7.72 d (J=8 Hz, 1H)

EXAMPLE 297

6-[[1-(4-Methylphenyl)-2-(3-pyridyl)-1H-benzimidazol-6-yl]oxy]hexanoic acid methyl ester was obtained by reaction of 6-[[4-amino-3-((4-methylphenyl)amino)phenyl]-oxy]hexanoic acid methyl ester with 3-pyridylcarbaldehyde according to general operating instructions 16.

MS (EI): 429 (molecular ion peak)

EXAMPLE 298

6-[[1-(4-Methylphenyl)-2-(4-pyridyl)-1H-benzimidazol-6-yl]oxy]hexanoic acid methyl ester was obtained by reaction of 6-[[4-amino-3-((4-methylphenyl)amino)phenyl]-oxy]hexanoic acid methyl ester with 4-pyridylcarbaldehyde according to general operating instructions 16;

MS (EI): 429 (molecular ion peak)

EXAMPLE 299

6-[[1-(4-Methylphenyl)-2-(2-thienyl)-1H-benzimidazol-6-yl]oxy]hexanoic acid methyl ester was obtained by reaction of 6-[[4-amino-3-((4-methylphenyl)amino)phenyl]-oxy]hexanoic acid methyl ester with 2-thienylcarbaldehyde according to general operating instructions 16.

MS (EI): 434 (molecular ion peak)

EXAMPLE 300

6-[[1-(4-Methylphenyl)-2-(3-thienyl)-1H-benzimidazol-6-yl]oxy]hexanoic acid methyl ester was obtained by reaction of 6-[[4-amino-3-((4-methylphenyl)amino)phenyl]oxy]hexanoic acid methyl ester with 3-thienylcarbaldehyde according to general operating instructions 16.

MS (EI): 434 (molecular ion peak)

EXAMPLE 301

6-[[2-(3-Indolyl)-1-(4-methylphenyl)-1H-benzimidazol-6-yl]oxy]hexanoic acid methyl ester was obtained by reaction of 6-[[4-amino-3-((4-methylphenyl)amino)phenyl]-oxy]hexanoic acid methyl ester with 3-indolylcarbaldehyde according to general operating instructions 16.

MS (EI): 467 (molecular ion peak)

EXAMPLE 302

6-[[1-(4-Methylphenyl)-2-(2-furyl)-1H-benzimidazol-6-yl]oxy]hexanoic acid methyl ester was obtained by reaction of 6-[[4-amino-3-((4-methylphenyl)amino)phenyl]-oxy]hexanoic acid methyl ester with 2-furylcarbaldehyde according to general operating instructions 16.

MS (EI): 418 (molecular ion peak)

EXAMPLE 303

6-[[1-(4-Methylphenyl)-2-(3-furyl)-1H-benzimidazol-6-yl]oxy]hexanoic acid methyl ester was obtained by reaction of 6-[[4-amino-3-((4-methylphenyl)amino)phenyl]-oxy]hexanoic acid methyl ester with 3-furylcarbaldehyde according to general operating instructions 16.

MS (EI): 418 (molecular ion peak)

EXAMPLE 304

6-[[1-(4-Methylphenyl)-2-(5-methyl-2-thienyl)-1H-benzimidazol-6-yl]oxy]hexanoic acid methyl ester was obtained by reaction of 6-[[4-amino-3-((4-methylphenyl)amino)phenyl]-oxy]hexanoic acid methyl ester with 5-methyl-2-thienyl-carbaldehyde according to general operating instructions 16.

MS (EI): 448 (molecular ion peak)

EXAMPLE 305

6-[[1-(4-Methylphenyl)-2-(4-bromo-2-thienyl)-1H-benzimidazol-6-yl]oxy]hexanoic acid methyl ester was obtained by reaction of 6-[[4-amino-3-((4-methylphenyl)amino)phenyl]-oxy]hexanoic acid methyl ester with 4-bromo-2-thienylcarbaldehyde according to general operating instructions 16.

MS (EI): 512/514 (molecular ion peak)

EXAMPLE 306

6-[[1-(4-Methylphenyl)-2-(3-methyl-2-thienyl)-1H-benzimidazol-6-yl]oxy]hexanoic acid methyl ester was obtained by reaction of 6-[[4-amino-3-((4-methylphenyl)amino)phenyl]-oxy]hexanoic acid methyl ester with 3-methyl-2-thienylcarbaldehyde according to general operating instructions 16.

MS (EI): 448 (molecular ion peak)

EXAMPLE 307

Inhibition of Microglia Activation

For in vitro production of Aβ-activated microglia, primary rat microglia with synthetic Aβ-peptide are incubated:

For simulation of Aβ deposits, synthetic Aβ peptide is dried on 96-hole tissue culture plates. A peptide stock solution is diluted by 2 mg/ml of $H_2O$ 1:50 in $H_2O$. To coat the 96-hole plates, 30 µl of this dilute peptide solution/hole is used, and it is dried overnight at room temperature.

Primary rat microglia are harvested by mixed glia cultures, which were obtained from P3 rat brains. In the production of mixed glia cultures, the brains are taken from 3-day-old rats, and meninges are removed. The isolation of cells is achieved by trypsinization (0.25% trypsin solution, 15 minutes at 37° C.)). After undigested tissue fragments are separated with the aid of a 40 µm nylon mesh, the isolated cells are centrifuged off (800 rpm/10 min). The cell pellet is resuspended in the culture medium and moved into 100 ml tissue culture flasks (1 brain/tissue culture flask). The cultivation of the cells is carried out over a period of 5-7 days in Dulbeccos modified Eagle Medium (DMEM, with glutamine), supplemented with penicillin (50 U/ml), streptomycin (40 µg/ml) and 10% (v/v) fetal calf serum (FCS) at 37° C. and 5% $CO_2$. During this incubation, an adhesive cellular film is formed, which mainly consists of astrocytes. Microglia proliferate as non-adhesive or weakly adhesive cells on the latter and are harvested via shaking incubation (420 rpm, 1 hour).

To activate the microglia by Aβ-peptide, $2.5 \times 10^4$ microglia/hole are grown on the Aβ-coated tissue culture plates and incubated over a period of 7 days in DMEM (with glutamine), supplemented with penicillin (50 U/ml), streptomycin (40 µg/ml) and 10% (v/v) fetal calf serum (FCS) at 37° C. and 5% $CO_2$. On day 5, a compound according to the invention is added at various concentrations (0.1, 0.3, 1.3 and 10 µM).

To quantify the microglia reactivity, the metabolic activity is measured on cultivation day 7 via the reduction of MTS (3-(4,5-dimethylthiazol-2-yl)-5-(3carboxymethoxyphenyl)-2-(sulfophenyl)-2H-tetrazolium), Owen's reagent, Baltrop, J. A. et al. Bioorg. & Med. Chem. Lett 1, 6111 (1991)). The percentage of inhibition relates to a control that is treated only with DMSO. The compounds according to the invention inhibit the microglia activation.

EXAMPLE 308

Cerebral Brain Infarction in Rats (MCAO Model)

The compounds according to the invention were tested for in vivo activity in an animal model for cerebral ischemia (stroke), the MCAO (permanent middle cerebral artery occlusion) model. One-sided obstruction of the middle cerebral artery (MCA) triggers a brain infarction, which is caused by the fact that the corresponding area of the brain is undernourished with oxygen and nutrients. The result of this undernourishment is a pronounced cellular degeneration and, subsequently, a strong microglia activation. This microglia activation reaches its maximum only after several days, however, and can last for several weeks. To test the substances, the compounds according to the invention were administered intraperitoneally 1-6 days after occlusion. On day 7, the animals were perfused and sacrificed. The extent of the microglia activation was measured by a modified immunohistochemical method. Vibratom sections of fixed brains were incubated with antibodies, whereby said sections detect the CR3 complement receptor or the MHCII complex from activated microglia. The quantification of the primary antibody bond was carried out by an enzyme-coupled detection system. The treatment with the compounds according to the invention resulted in a significant reduction of microglia activation in the brain hemisphere affected by the brain infarction. The reduction was at least 20%.

EXAMPLE 309

Activation of Macrophages

To test substances on macrophages/monocytes, LPS-activated THP-1 cells were used. For this purpose, $2.5 \times 10^6$ cells/ml in RPMI medium (RPMI 1640+10% FCS) were grown. The compounds according to the invention were added at a concentration of 5 µM and pre-incubated for 30 minutes. The stimulation of the cells was carried out overnight at 37 C with 1 µg/ml of LPS. Then, the medium was harvested, and the amount of TNFα was determined quantitatively. The treatment of the cells with the substances according to the invention resulted in a reduction of the amount of $TNF_\alpha$ of at least 30%.

The invention claimed is:

1. A method of treating inflammation in a patient, comprising administering an effective amount of a benzimidazole compound according to formula I

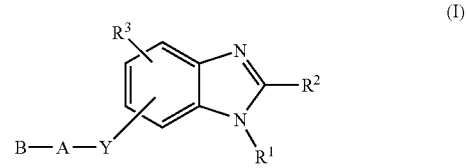

or a physiologically acceptable salt thereof,
in which
$R^1$ means a monocyclic or bicyclic $C_{6-12}$ aryl group or a monocyclic or bicyclic 5- to 10-membered heteroaryl group with 1-4 heteroatoms selected from N, S and O atoms, wherein said aryl or heteroaryl group is optionally substituted with up to three substituents, independently of one another, selected from F, Cl, Br, I, $C(NH)NH_2$, $C(NH)NHR^4$, $C(NH)NR^4R^{4'}$, $C(NR^4)NH_2$, $C(NR^4)NHR^{4'}$, $C(NR^4)NR^4R^{4'}$, XOH, $XOR^4$, $XOCOR^4$, $XOCONHR^4$, $XOCOOR^4$, $XCOR^4$, $XC(NOH)R^4$, $XC(NOR^4)R^{4'}$, $XC(NO(COR^4))R^{4'}$ XCN, XCOOH, $XCOOR^4$, $XCONH_2$, $XCONR^4R^{4'}$, $XCONHR^4$, XCONHOH, $XCONHOR^4$, $XCOSR^4$, $XSR^4$, $XSOR^4$, $XSO_2R^4$, $SO_2NH_2$, $SO_2NHR^4$, $SO_2NR^4R^{4'}$, $NO_2$, $XNH_2$, $XNHR^4$, $XNR^4R^{4'}$, $XNHSO_2R^4$, $XN(SO_2R^4)SO_2R^{4'}$, $XNR^4SO_2R^{4'}$, $XNHCOR^4$, $XNHCOOR^4$, $XNHCONHR^4$, tetrahydro-2,5-dioxopyrrol-1-yl, 2,5-dihydro-2,5-dioxopyrrol-1-yl, 2,7-dihydro-2,7-dioxoisoindol-1-yl, and $R^4$, wherein two substituents at $R^1$, if they are in ortho-position to one another, are optionally linked to one another to jointly form methanediylbisoxy, ethane-1,2-diylbisoxy, propane-1,3-diyl, or butane-1,4-diyl, $R^2$ means a monocyclic or bicyclic 5- to 10-membered heteroaryl group with 1-4 heteroatoms selected from N, S and O atoms, wherein said heteroaryl group is optionally substituted with up to three independently of one another, selected from of F, Cl, Br, I, XOH, $XOR^4$, $XOCOR^4$, $XOCONHR^4$, $XOCOOR^4$, $XCOR^4$, $XC(NOH)R^4$, $XC(NOR^4)R^{4'}$, $XC(NO(COR^4))R^{4'}$, XCOOH, $XCOOR^4$, $XCONH_2$, $XCONHR^4$, $XCONR^4R^{4'}$, XCONHOH, $XCONHOR^4$, $XCOSR^4$, $XSR^4$, $XSOR^4$, $XSO_2R^4$, $SO_2NH_2$, $SO_2NHR^4$, $SO_2NR^4R^{4'}$, $NO_2$, $XNHR^4$, $XNR^4R^{4'}$, $XNHSO_2R^4$, $XN(SO_2R^4)SO_2R^{4'}$, $XNR^4SO_2R^{4'}$, tetrahydro-2,5-dioxopyrrol-1-yl, 2,5-dihydro-2,5-dioxopyrrol-1-yl, 2,7-dihydro-2,7-dioxoisoindol-1-yl, and $R^4$, wherein two substituents at $R^2$, if they are in ortho-position to one another, are optionally linked to one another to jointly form methanediyl-bisoxy, ethane-1,2-diylbisoxy, propane-1,3-diyl, or butane-1,4-diyl, $R^3$ means one or two substituents, independently of one another, which are hydrogen, F, Cl, Br, I, XOH, $XOR^4$, $XOCOR^4$, $XOCONHR^4$, $XOCOOR^4$, $XCOR^4$, $XC(NOH)R^4$, $XC(NOR^4)R^{4'}$, $XC(NO(COR^4))R^{4'}$, XCN, XCOOH, $XCOOR^4$, $XCONH_2$, $XCONHR^4$, $XCONR^4R^{4'}$, XCONHOH, $XCONHOR^4$, $XCOSR^4$, $XSR^4$, $XSOR^4$, $XSO_2R^4$, $SO_2NH_2$, $SO_2NHR^4$, $SO_2NR^4R^{4'}$, $NO_2$, $XNH_2$, $XNHR^4$, $XNR^4R^{4'}$, $XNHSO_2R^4$, $XNR^4SO_2R^{4'}$, $XN(SO_2R^4)(SO_2R^{4'})$ $XNHCOR^4$, $XNHCOOR^4$, $XNHCONHR^4$, tetrahydro-2,5-dioxopyrrol-1-yl, 2,5-dihydro-2,5-dioxopyrrol-1-yl, 2,7-dihydro-2,7-dioxoisoindol-1-yl, and/or $R^4$, wherein two substituents at $R^3$, if they are in ortho-position to one another, are optionally linked to one another to jointly form methanediylbisoxy, ethane-1,2-diylbisoxy, propane-1,3-diyl, or butane-1,4-diyl, $R^4$ and $R^{4'}$, independently of one another, mean $C_{1-4}$ perfluoroalkyl, $C_{1-6}$ alkyl, $C_{2-6}$ alkenyl, $C_{2-6}$alkinyl, $C_{3-7}$cycloalkyl, ($C_{1-3}$ alkyl-$C_{3-7}$cycloalkyl), $C_{1-3}$ alkyl-$C_{6-10}$ aryl, $C_{1-3}$ alkyl-5-to-10-membered heteroaryl with 1-4 heteroatoms selected from N, S and O atoms, $C_{6-10}$ aryl, or 5- to 10-membered heteroaryl with 1-4 heteroatoms selected from N, S and O atoms, wherein the aryl and heteroaryl groups are optionally substituted with one or two substituents selected from F, Cl, Br, $CH_3$, $C_2H_5$, $NO_2$, $OCH_3$, $OC_2H_5$, $CF_3$, and $C_2F_5$, or optionally carry an annelated methanediylbisoxy group or ethane-1,2-diylbisoxy group, and wherein a 5-membered cycloalkyl ring optionally has an N or O ring member, and a 6- or 7-membered cycloalkyl ring optionally has one or two ring members selected from N and O, wherein ring nitrogens optionally are substituted with $C_{1-3}$ alkyl or $C_{1-3}$ alkanoyl, $R^5$ and $R^{5'}$, independently of one another, mean $C_{1-6}$ alkyl, $C_{2-6}$alkenyl, $C_{2-6}$alkinyl (wherein in each case a carbon atom is optionally replaced by O, S, SO, $SO_2$, NH, $NC_{1-3}$ alkyl or $NC_{1-3}$ alkanoyl), $C_{3-7}$cycloalkyl-$C_{0-3}$ alkyl, $C_{6-10}$ aryl or 5- to 10-membered heteroaryl with 1-4 heteroatoms selected from N, S, and O atoms, wherein a 5-membered cycloalkyl ring optionally has an N or O ring member and a 6- or 7-membered cycloalkyl ring optionally has one or two ring members selected from N and O, wherein ring nitrogens optionally are substituted with $C_{1-3}$ alkyl or $C_{1-3}$ alkanoyl, wherein the alkyl, alkenyl and alkinyl groups are optionally substituted with one of the previously mentioned cycloalkyls, aryls or heteroaryls, and wherein all previously mentioned alkyl and cycloalkyl radicals are optionally substituted with one or two substituents selected from of $CF_3$, $C_2F_5$, OH, $OC_{1-3}$ alkyl, $NH_2$, $NHC_{1-3}$ alkyl, $NHC_{1-3}$ alkanoyl, $N(C_{1-3}$ alkyl$)_2$$N(C_{1-3}$ alkyl)($C_{1-3}$ alkanoyl), COGH, $CONH_2$, and $COOC_{1-3}$ alkyl, and all previously mentioned aryl and heteroaryl groups are optionally substituted with one or two substituents selected from of F, Cl, Br, $CH_3$, $C_2H_5$, $NO_2$, $OCH_3$, $OC_2H_5$, $CF_3$, and $C_2F_5$ or optionally carry an annelated methanediylbisoxy or ethane-1,2-diylbisoxy group, or $R^5$ and $R^{5'}$ together with the nitrogen atom form a 5-to 7-membered heterocyclic ring, which optionally contains another oxygen, nitrogen or sulfur atom and is optionally substituted with $C_{1-4}$ alkyl, $C_{1-4}$ alkoxy-$C_{0-2}$ alkyl, $C_{1-4}$ alkoxycarbonyl, aminocarbonyl or phenyl, A means $C_{1-10}$ alkanediyl, $C_{2-10}$ alkenediyl, $C_{2-10}$ alkinediyl, ($C_{0-5}$alkanediyl-$C_{3-7}$, cycloalkanediyl-$C_{0-5}$ alkanediyl), wherein a 5-membered cycloalkyl ring optionally has a N or O ring member, and a 6-or7-membered cycloalkyl ring optionally has one or two ring members selected from N and O, wherein ring nitrogens are optionally substituted with $C_{1-3}$ alkyl or $C_{1-3}$ alkanoyl, wherein in an aliphatic group, one or two carbon atoms are each optionally replaced by O, NH, $NC_{1-3}$ alkyl, and/or $NC_{1-3}$ alkanoyl, and wherein alkyl or cycloalkyl groups are optionally substituted with up to two substituents selected from of =O, OH, $OC_{1-3}$ alkyl, $NH_2$, $NHC_{1-3}$ alkyl, $NHC_{1-3}$ alkanoyl, $N(C_{1-3}$ alkyl$)_2$, and $N(C_{1-3}$ alkyl)($C_{1-3}$ alkanoyl), B means COOH, $COOR^5$, $CONH_2$, $CONHNH_2$, $CONHR^5$, $CONR^5R^{5'}$, CONHOH, $CONHOR^5$, $SO_3H$, $SO_2NH_2$, $SO_2NHR^5$, $SO_2NR^5R^{5'}$, $PO^3H$, PO(OH)($OR^5$), PO($OR^5$)($OR^{5'}$), PO(OH)($NHR^5$), PO($NHR^5$)($NHR^{5'}$), or tetrazolyl, each bonded to a carbon atom of group A, or the entire group Y-A-B is $N(SO_2R^4)(SO_2R^{4'})$ or $NHSO_2R^4$, X means a bond, $CH_2$, $(CH_2)_2$, $CH(CH_3)$, $(CH_2)_3$, $CH(CH_2CH_3)$, $CH(CH_3)CH_2$, or $CH_2CH(CH_3)$, Y means O, NH, $NR^4$, $NCOR^4$, or $NSO_2R^4$, provided that if Y means NH, $NR^4$, $NCOR^4$ or $NSO_2R^4$, and a) $R^2$ contains a nitrogen-containing, saturated heterocyclic compound, this heterocyclic compound is not substituted in the imine nitrogen with H, methyl, ethyl, propyl or isopropyl, or b) in optionally present groups $XNHR^4$ or $XNR^4R^{4'}$ of $R^2$, $R^4$ and/or $R^{4'}$ does not mean $C_{1-4}$ alkyl, that B does not mean COOH, SO$_3$H, PO$^3$H$_2$ or tetrazolyl at the same time R$^1$ means C$_{5-6}$ heteroaryl or phenyl which are, independently of one another, unsubstituted or substituted simply with C$_{1-6}$ alkyl, C$_{1-4}$ perfluoroalkyl, OC$_{1-6}$ alkyl, OC$_{1-4}$ perfluoroalkyl, COOH, COOC$_{1-6}$ alkyl, COC$_{1-6}$ alkyl, CONH$_2$, CONHR$^4$, NO$_2$, NH$_2$, NHCOR$^4$, NHSO$_2$R$^4$, or with 1 or 2 halogen atoms selected from of F, Cl, Br, and I, and R$^2$ means C$_{5-6}$ heteroaryl substituted simply with C$_{1-6}$ akyl, C$_{1-4}$ perfluoroalkyl, OC$_{1-6}$ alkyl, OC$_{1-4}$ perfluoroalkyl, COOH, COOC$_{1-6}$ alkyl, COC$_{1-6}$ alkyl, CONH$_2$, CONHR$^4$, NO$_2$, NH$_2$, NHCOR$^4$, NHSO$_2$R$^4$, or with 1 or 2 halogen atoms selected from of Cl, Br and I.

2. A method according to claim 1, wherein
R$^1$ means a monocyclic or bicyclic C$_{2-6}$ aryl group or a monocyclic or bicyclic 5- to 10-membered heteroaryl group with 1-2 heteroatoms selected from N, S and O atoms, wherein said aryl or heteroaryl group is optionally substituted with up to three substituents, independently of one another, selected from of F, Cl, Br, XOH, XOR$^4$, XOCOR$^4$, XOCONHR$^4$, XOCOOR$^4$, XCOR$^4$, XCN, XCOOH, XCOOR$^4$, XCONH$_2$, XCONR$^4$R$^{4'}$, XCONHR$^4$, XCONHOH, XCONHOR$^4$, XCOSR$^4$, XSR$^4$, NO$_2$, XNHR$^4$, XNR$^4$R$^{4'}$, and R$^4$,
wherein two substituents at R$^1$, if they are in ortho-position to one another, are optionally linked to one another to jointly form methanediylbisoxy, ethane-1,2-diylbisoxy, propane-1,3-diyl, or butane-1,4-diyl.

3. A method according to claim 1, wherein
R$^2$ means monocyclic or bicyclic 5- to 10-membered heteroaryl group with 1-2 heteroatoms selected from N, S and O atoms, wherein said heteroaryl group is optionally substituted with up to three, independently of one another, selected from of F, Cl, Br, XOH, XOR$^4$, XOCOR$^4$, XOCONHR$^4$, XOCOOR$^4$, XCOR$^4$, XC(NOH)R$^4$, XC(NOR$^4$)R$^{4'}$, XC(NO(COR$^4$))R$^{4'}$, XCOOH, XCOOR$^4$, XCONH$_2$, XCONHR$^4$, XCONR$^4$R$^{4'}$, XCONHOH, XCONHOR$^4$, XCOSR$^4$, XSR$^4$, XSOR$^4$, XSO$_2$R$^4$, SO$_2$NH$_2$, SO$_2$NHR$^4$, SO$_2$NR$^4$R$^{4'}$, NO$_2$, XNHR$^4$, XNR$^4$R$^{4'}$, XNHSO$_2$R$^4$, XN(SO$_2$R$^4$)SO$_2$R$^{4'}$, XNR$^4$SO$_2$R$^{4'}$, and R$^4$,
wherein two substituents at R$^2$, if they are in ortho-position to one another, are optionally linked to one another to jointly form methanediylbisoxy, ethane-1,2-diylbisoxy, propane-1,3-diyl, or butane-1,4-diyl.

4. A method according to claim 1, wherein
R$^3$ means one or two substituents, independently of one another, which are hydrogen, F, Cl, Br, XOH, XOR$^4$, XOCOR$^4$, XOCONHR$^4$, XOCOOR$^4$, XCOR$^4$, XC(NOH)R$^4$, XC(NOR$^4$)R$^{4'}$, XC(NO(COR$^4$))R$^{4'}$, XCN, XSR$^4$, XSOR$^4$, XSO$_2$R$^4$, SO$_2$NH$_2$, SO$_2$NHR$^4$, SO$_2$NR$^4$R$^{4'}$, NO$_2$, XNH$_2$, XNHR$^4$, XNR$^4$N$^{4'}$, XNHSO$_{2R}^4$, XNR$^4$SO$_2$R$^{4'}$, XN(SOR$^4$)SOR$^{4'}$, XNHCOR$^4$, XNHCOOR$^4$, XNHCONHR$^4$, and/or R$^4$,
wherein two substituents at R$^3$, if they are in ortho-position to one another, are optionally linked to one another to jointly form methanediylbisoxy, ethane-1,2-diylbisoxy, propane-1,3-diyl, or butane-1,4-diyl.

5. A method according to claim 1, wherein
R$^4$ and R$^{4'}$, independently of one another, mean CF$_3$, C$_2$F$_5$, C$_{1-4}$ alkyl, C$_{2-4}$ alkenyl, C$_{2-4}$ alkinyl, C$_{3-6}$ cycloalkyl, (C$_{1-3}$ alkyl-C$_{3-6}$ cycloalkyl), phenyl or 5- to 6-membered heteroaryl with 1-2 heteroatoms selected from of N, S and O atoms, wherein the phenyl and heteroaryl groups are optionally, substituted with one or two substituents selected from of F, Cl, Br, CH$_3$, C$_2$H$_5$, OCH$_3$, $_{OC_2}$H$_5$, CF$_3$, and C$_2$F$_5$,
and wherein a 5-membered cycloalkyl ring optionally has a N or O ring member, and a 6-membered cycloalkyl ring optionally has one or two ring members selected from N and O, wherein ring nitrogens optionally are substituted with C$_{1-3}$ alkyl or C$_{1-3}$ alkanoyl.

6. A method according to claim 1, wherein
R$^5$ and R$^{5'}$, independently of one another, are optionally C$_{1-6}$ alkyl (wherein a carbon atom is optionally replaced by O, NH, NC$_{1-3}$ alkyl, or NC$_{1-3}$ alkanoyl) or C$_{3-7}$ cycloalkyl-C$_{0-3}$-alkyl, wherein a 5- membered cycloalkyl ring optionally has a N or O ring member and a 6- or 7-membered cycloalkyl ring optionally has one or two ring members selected from N and O, wherein ring nitrogens are optionally substituted with C$_{1-3}$ alkyl or C$_{1-3}$ alkanoyl,
and wherein the C$_{1-6}$ alkyl group is optionally substituted with one of the previously mentioned cycloalkyls or a 5- to 6-membered heteroaromatic compound with 1-2 heteroatoms selected from N, S and O atoms, wherein all previously mentioned alkyl and cycloalkyl groups are optionally substituted with up to two substituents selected from of CF$_3$, OH, and OC$_{1-3}$ alkyl, and the previously mentioned heteroaryl groups are optionally substituted with one or two substituents selected from of F, Cl, CF$_3$, CH$_3$, C$_2$H$_5$, OCH$_3$, and OC$_2$H$_5$, or
R$^5$ and R$^{5'}$ together with the nitrogen atom form a 5- to 7-membered heterocyclic group, which optionally contains another oxygen, nitrogen or sulfur atom and is optionally substituted with C$_{1-4}$ alkyl, C$_{1-4}$ alkoxy-C$_{0-2}$ alkyl, C$_{1-4}$ alkoxy-carbonyl, aminocarbonyl or phenyl.

7. A method according to claim 1, wherein
A means C$_{1-10}$ alkanediyl, C$_{2-10}$ alkenediyl, C$_{2-10}$ alkinediyl, (C$_{05}$ alkanediyl-C$_{3-7}$ cycloalkanediyl-C$_{0-5}$ alkanediyl), wherein a 5-membered cycloalkyl ring optionally has a N or O ring member and a 6- or 7-membered cycloalkyl ring optionally has one or two ring members selected from N and O, wherein ring nitrogens are optionally substituted with C$_{1-3}$ alkyl or C$_{1-3}$ alkanoyl, wherein in an aliphatic group one or two carbon atoms are each optionally replaced by O, NH, N C$_{1-3}$ alkyl, and/or NC$_{1-3}$ alkanoyl.

8. A method according to claim 1, wherein
B means COOH, COOR$^5$, CONH$_2$, CONHR$^5$, CONR$^5$R$^{5'}$, CONHOH, CONHOR$^5$ or tetrazolyl, in each case bonded to a carbon atom of group A.

9. A method according to claim 1, wherein
X means a bond or CH$_2$.

10. A method according to claim 1, wherein
Y means O.

11. A method according to claim 1, wherein the compound administered is 6-[[1-phenyl-2-(4-pyridinyl)-1H-benzimidazol-6-yl]oxy]hexanoic acid methyl ester.

12. A method according to claim 1, wherein the compound administered is
6-[[1-phenyl-2-(benzothien-2-yl)-1H-benzimidazol-6-yl]oxy]hexanoic acid methyl ester,
6-[[1-phenyl-2-(benzothien-2-yl)-1H-benzimidazol-6-yl]oxy]hexanoic acid,
6-[[1-phenyl-2-(3-pyridinyl)-1H-benzimidazol-6-yl]oxy] hexanoic acid methyl ester,
6-[[1-(4-methylphenyl)-2-(3-pyridyl)-1H-benzimidazol-6-yl]oxy]hexanoic acid methyl ester,
6-[[1-(4-methylphenyl)-2-(4-pyridyl)-1H-benzimidazol-6-yl]oxy]hexanoic acid methyl ester, 6-[[1-(4-methylphenyl)-2-(2-thienyl)-1H-benzimidazol-6-yl]oxy]hexanoic acid methyl ester,
6-[[1-(4-methylphenyl)-2-(3-thienyl)-1H-benzimidazol-6-yl]oxy]hexanoic acid methyl ester,
6-[[2-(3-indolyl)-1-(4-methylphenyl)-1H-benzimidazol-6-yl]oxy]hexanoic acid methyl ester,
6-[[1-(4-methylphenyl)-2-(2-furyl)-1H-benzimidazol-6-yl]oxy]hexanoic acid methyl ester,
6-[[1-(4-methylphenyl)-2-(3-furyl)-1H-benzimidazol-6-yl]oxy]hexanoic acid methyl ester,
6-[[1-(4-methylphenyl)-2-(5-methyl-2-thienyl)-1H-benzimidazol-6-yl]oxy]hexanoic acid methyl ester, or
6-[[1-(4-methylphenyl)-2-(3-methyl-2-thienyl)-1H-benzimidazol-6-yl]oxy]hexanoic acid methyl ester.

13. A method for treating a patient suffering from chronic inflammation comprising administering to said patient an effective amount of a benzimidazole compound of formula II

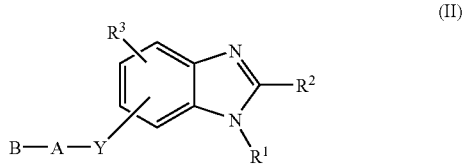

(II)

or a physiologically compatible acceptable salt thereof, in which $R^1$ means a monocyclic or bicyclic $C_{6-12}$ aryl group or a monocyclic or bicyclic 5- to 10-membered heteroaryl group with 1-4 heteroatoms selected from N, S and O atoms, wherein said aryl or heteroaryl group is optionally substituted with up to three substituents, independently of one another, selected from F, Cl, Br, I, C(NH)NH$_2$, C(NH)NHR$^4$, C(NH)NR$^4$R$^{4'}$, C(NR$^4$)NH$_2$, C(NR$^4$)NHR$^{4'}$, C(NR$^4$)NR$^4$R$^{4'}$, XOH, XOR$^4$, XOCOR$^4$, XOCONHR$^4$, XOCOOR$^4$, XCOR$^4$, XC(NOH)R$^4$, XC(NOR$^4$)R$^{4'}$, XC(NO(COR$^4$))R$^{4'}$, XCN, XCOOH, XCOOR$^4$, XCONH$_2$, XCONR$^4$R$^{4'}$, XCONHR$^4$, XCONHOH, XCONHOR$^4$, XCOSR$^4$, XSR$^4$, XSOR$^4$, XSO$_2$R$^4$, SO$_2$NH$_2$, SO$_2$NHR$^4$, SO$_2$NR$^4$R$^{4'}$, NO$_2$, XNH$_2$, XNHR$^4$, XNR$^4$R$^{4'}$, XNHSO$_2$R$^4$, XN(SO$_2$R$^4$)(SO$_2$R$^{4'}$), XNR$^4$SO$_2$R$^{4'}$, XNHCOR$^4$, XNHCOOR$^4$, XNHCONHR$^4$, tetrahydro-2,5-dioxopyrrol-1-yl, 2,5-dihydro-2,5-dioxopyrrol-1-yl, 2,7-dihydro-2,7-dioxoisoindol-1-yl, and R$^4$, wherein two substituents at R$^1$, if they are in ortho-position to one another, are optionally linked to one another to jointly form methanediylbisoxy, ethane-1,2-diylbisoxy, propane-1,3-diyl, or butane-1,4-diyl, $R^2$ means a monocyclic or bicyclic 5- to 10-membered heteroaryl group with 1-4 heteroatoms selected from N, S and O atoms, wherein said heteroaryl group is optionally substituted with up to three substituents, independently of one another, selected from of F, Cl, Br, I, C(NH)NH$_2$, C(NH)NHR$^4$, C(NH)NR$^4$R$^{4'}$, C(NR$^4$)NH$_2$, C(NR$^4$)NHR$^{4'}$, C(NR$^4$)NR$^4$R$^{4'}$, XOH, XOR$^4$, XOCOR$^4$, XOCONHR$^4$, XOCOOR$^4$, XCOR$^4$, XC(NOH)R$^4$, XC(NOR$^4$)R$^{4'}$, XC(NO(COR$^4$))R$^{4'}$, XCN, XCOOH, XCOOR$^4$, XCONH$_2$, XCONR$^4$R$^{4'}$, XCONHR$^4$, XCONHOH, XCONHOR$^4$, XCOSR$^4$, XSR$^4$, XSOR$^4$, XSO$_2$R$^4$, SO$_2$NH$_2$, SO$_2$NHR$^4$, SO$_2$NR$^4$R$^{4'}$, NO$_2$, XNH$_2$, XNHR$^4$, XNR$^4$R$^{4'}$XNHSO$_2$R$^4$, $^{XN(SO}$$_2$R$^4$)(SO$_2$R$^{4'}$), XNR$^4$SO$_2$R$^{4'}$, XNHCOR$^4$, XNHCOOR$^4$, XNH-CONHR$^4$, tetrahydro-2,5-dioxopyrrol-1-yl, 2,5-dihydro-2,5-dioxopyrrol-1-yl, 2,7-dihydro-2,7-dioxoisoindol-1-yl, and R$^4$, wherein two substituents at R$^2$, if they are in ortho-position to one another, are optionally linked to one another to jointly form methanediyl-bisoxy, ethane-1,2-diylbisoxy, propane-1,3-diyl, or butane-1,4-diyl, $R^3$ stands for one or two substituents, independently of one another, which are hydrogen, F, Cl, Br, I, XOH, XOR$^4$, XOCOR$^4$, XOCONHR$^4$, XOCOOR$^4$, XCOR$^4$, XC(NOH)R$^4$, XC(NOR$^4$)R$^{4'}$, XC(NO(COR$^4$))R$^{4'}$, XCN, XCOOH, XCOOR$^4$, XCONH$_2$, XCONHR$^4$, XCONR$^4$R$^{4'}$, XCONHOH, XCONHOR$^4$, XCOSR$^4$, XSR$^4$, XSOR$^4$, XSO$_2$R$^4$, SO$_2$NH$_2$, SO$_2$NHR$^4$, SO$_2$NR$^4$R$^{4'}$, NO$_2$, XNH$_2$, XNHR$^4$, XNR$^4$R$^{4'}$, XNHSO$_2$R$^4$, XNR$^4$SO$_2$R$^{4'}$, XN(SO$_2$R$^4$)(SO$_2$R$^{4'}$), XNHCOR$^4$, XNHCOOR$^4$, XNHCONHR$^4$, tetrahydro-2,5-dioxopyrrol-i-yl, 2,5-dihydro-2,5-dioxopyrrol-1-yl, 2,7-dihydro-2,7-dioxoisoindol-1-yl, or R$^4$, two substituents at R$^3$, if they are in ortho-position to one another, are optionally linked to one another to jointly form methanediylbisoxy, ethane-1,2-diylbisoxy, propane-1,3-diyl, or butane-1,4-diyl, $R^4$ and $R^{4'}$, independently of one another, mean $C_{1-4}$ perfluoroalkyl, $C_{1-6}$ alkyl, $C_{2-6}$alkenyl, $C_{2-6}$alkinyl, $C_{3-7}$cycloalkyl, ($C_{1-3}$ alkyl-$C_{3-7}$cycloalkyl), $C_{1-3}$ alkyl-$C_{6-10}$ aryl, $C_{1-3}$ alkyl-5-to-10-membered heteroaryl with 1-4 heteroatoms selected from N, S and O atoms, $C_{6-10}$ aryl, or 5- to 10-membered heteroaryl with 1-4 heteroatoms selected from N, S and O atoms, wherein the $C_{6-10}$ aryl and heteroaryl groups are optionally substituted with one or two substituents selected from F, Cl, Br, CH$_3$, C$_2$H$_5$, NO$_2$, OCH$_3$, OC$_2$H$_5$, CF$_3$, and C$_2$F$_5$ or optionally carry an annelated methanediyl-bisoxy group or ethane-1,2-diylbisoxy group, and wherein a 5-membered cycloalkyl ring optionally has a N or O ring member, and a 6- or 7-membered cycloalkyl ring optionally has one or two ring members selected from N and O, wherein ring nitrogens are optionally substituted with $C_{1-3}$ alkyl or $C_{1-3}$ alkanoyl, $R^5$ and $R^{5'}$, independently of one another, mean hydrogen, $C_{1-6}$ alkyl, $C_{2-6}$alkenyl, $C_{2-6}$alkinyl, (wherein in each case a carbon atom is optionally replaced by O, S, SO, SO$_2$, NH, N $C_{1-3}$ alkyl or N $C_{1-3}$ alkanoyl), $C_{3-7}$ cycloalkyl-$C_{0-3}$ alkyl, (wherein a 5-membered cycloalkyl ring optionally has a N or O ring member, and a 6- or 7-membered cycloalkyl ring optionally has one or two ring members selected from N and O, and wherein ring nitrogens are optionally substituted with $C_{1-3}$ alkyl or $C_{1-3}$ alkanoyl), $C_{6-10}$ aryl or 5- to 10-membered heteroaryl with 1-4 heteroatoms selected from N, S, and O atoms, wherein the mentioned alkyl, alkenyl and alkinyl groups are optionally substituted with one of the previously mentioned cycloalkyls, aryls or heteroaryls, wherein all previously mentioned alkyl and cycloalkyl radicals are optionally substituted with up to two substituents selected from CF$_3$, C$_2$F$_5$, OH, OC$_{1-3}$ alkyl, NH$_2$, NHC$_{1-3}$ alkyl, NHC$_{1-3}$ alkanoyl, N(C$_{1-3}$ alkyl)$_2$, N(C$_{1-3}$ alkyl)(C$_{1-3}$ alkanoyl), COOH, CONH$_2$, and COOC$_{1-3}$ alkyl, and all previously mentioned aryl and heteroaryl groups are optionally substituted with one or two substituents selected from F, Cl, Br, CH$_3$, C$_2$H$_5$, NO$_2$, OCH$_3$, OC$_2$H$_5$, CF$_3$, and C$_2$F$_5$ or optionally carry an annelated methanediylbisoxy or ethane-1 ,2-diylbisoxy group, or $R^5$ and $R^{5'}$ together with the nitrogen atom form a 5-to 7-membered heterocyclic group, which optionally contains another oxygen, nitrogen or sulfur atom and is optionally substituted with $C_{1-4}$ alkyl, $C_{1-4}$ alkoxy-$C_{0-2}$ alkyl, $C_{1-4}$ alkoxy-carbonyl, aminocarbonyl or phenyl, A means $C_{1-10}$ alkanediyl, $C_{2-10}$ alkenediyl, $C_{2-10}$ alkinediyl, ($C_{0-5}$ alkanediyl-$C_{3-7}$ cycloalkanediyl-$C_{0-5}$ alkanediyl), ($C_{0-5}$ alkanediylarylene-$C_{0-5}$ alkanediyl), or $C_{0-5}$ alkanediyl-heteroarylene-$C_{0-5}$ alkanediyl), wherein the aryl and heteroaryl groups are optionally substituted with one or two substituents selected from F, Cl, Br, $CH_3$, $C_2H_5$, $NO_2$, $OCH_3$, $OC_2H_5$, $CF_3$, and $C_2F_5$, wherein a 5-membered cycloalkyl ring optionally has a N or O ring member and a 6- or 7-membered cycloalkyl ring optionally has one or two ring members selected from N and O, wherein ring nitrogens are optionally substituted with $C_{1-3}$ alkyl or $C_{1-3}$ alkanoyl, wherein in an aliphatic group one or two carbon atoms are each optionally replaced by O, NH, $NR^4$, $NCOR^4$, or $NSO_2R^4$, and wherein alkyl or cycloalkyl groups are optionally substituted with up to two substituents selected from F, OH, $OR^4$, $OCOR^{4,}$ =$O$, $NH_2$, $NR^4R^{4'}$, $NHCOR^4$, $NHCOOR^4$, $NHCONHR^4$, $NHSO_2R^4SH$, and $SR^4$, B means hydrogen, OH, $OCOR^5$, $OCONHR^5$, $OCOOR^5$, $COR^5$, $C(NOH)R^5$, $C(NOR^5)R^{5'}$, $C(NO(COR^5))R^{5'}$, COOH, $COOR^5$, $CONH_2$, $CONHNH_2$, $CONHR^5$, $CONR^5R^{5'}$, CONHOH, $CONHOR^5$, $SO_3H$, $SO_2NH_2$, $SO_2NHR^5$, $SO_2NR^5R^{5'}$, $PO_3H$, $PO(OH)(OR^5)$, $PO(OR^5)(OR^{5'})$, $PO(OH)(NHR^5)$, $PO(NHR^5)(NH R^{5'})$, or tetrazolyl, each bonded to a carbon atom of group A, or the entire group Y-A-B is $N(SO_2R^4)(SO_2R^{4'})$ or $NHSO_2R^4$, X means a bond, $CH_2$, $(CH_2)_2$, $CH(CH_3)$, $(CH_2)_3$, $CH(CH_2CH_3)$, $CH(CH_3)CH_2$, or $CH_2CH(CH_3)$, and Y means a bond, O, S, SO, $SO_2$, NH, $NR^4$, $NCOR^4$, or $NSO_2R^4$.

14. A method according to claim 13, wherein $R^1$ means a monocyclic or bicyclic aryl group or a monocyclic or bicyclic 5- to 10-membered heteroaryl group with 1-2 heteroatoms selected from N, S and O atoms, wherein said aryl or heteroaryl group is optionally substituted with up to three substituents, independently of one another, selected from of F, Cl, Br, XOH, $XOR^4$, $XOCOR^4$, $XOCONHR^4$, $XOCOOR^4$, $XCOR^4$, XCN, XCOOH, $XCOOR^4$, $XCONH_2$, $XCONR^4R^{4'}$, $XCONHR^4$, XCONHOH, $XCONHOR^4$, $XCOSR^4$, $XSR^4$, $NO_2$, $XNHR^4$, $XNR^4R^{4'}$, and $R^4$, wherein two substituents at $R^1$, if they are in ortho-position to one another, are optionally linked to one another to jointly form methanediylbisoxy, ethane-1,2-diylbisoxy, propane-1,3-diyl, or butane-1,4-diyl.

15. A method according to claim 13, wherein $R^2$ means a monocyclic or bicyclic 5- to 10-membered heteroaryl group with 1-2 heteroatoms selected from N, S and O atoms, wherein the heteroaryl group is optionally substituted with up to three, independently of one another, selected from of F, Cl, Br, XOH, $XOR^4$, $XOCOR^4$, $XOCONHR^4$, $XOCOOR^4$, $XCOR^4$, $XC(NOH)R^4$, $XC(NOR^4)R^{4'}$, $XC(NO(COR^4))R^{4'}$, XCN, XCOOH, $XCOOR^4$, $XCONH_2$, $XCONR^4R^{4'}$, $XCONHR^4$, XCONHOH, $XCONHOR^4$, $XCOSR^4$, $XSR^4$, $XSOR^4$, $XSO_2R^4$, $SO_2NH_2$, $SO_2NHR^4$, $SO_2NR^4R^{4'}$, $NO_2$, $XNH_2$, $XNHR^4$, $XNR^{4R4'}$, $XNHSO_2R^4$, $XN(SO_2R^4)(SO_2R^{4'})$, $XNR^4SO_2R^{4'}$, $XNHCOR^4$, $XNHCOOR^4$, $XNHCONHR^4$, and $R^4$, wherein two substituents at $R^2$, if they are in ortho-position to one another, are optionally linked to one another to jointly form methanediylbisoxy, ethane-1,2-diylbisoxy, propane-1,3-diyl, or butane-1,4-diyl.

16. A method according to claim 13, wherein $R^3$ stands for one or two substituents, independently of one another, selected from which are hydrogen, F, Cl, Br, XOH, $XOR^4$, $XOCOR^4$, $XOCONHR^4$, $XOCOOR^4$, $XCOR^4$, $XC(NOH)R^4$, $XC(NOR^4)R^{4'}$, $XC(NO(COR^4))R^{4'}$, XCN, $XSR^4$, $XSOR^4$, $XSO_2R^4$, $SO_2NH_2$, $SO_2NHR^4$, $SO_2NR^4R^{4'}$, $NO_2$, $XNH_2$, $XNHR^4$, $XNR^4R^{4'}$, $XNHSO_2R^4$, $XNR^4SO_2R^{4'}$, $XN(SO_2R^4)(SO_2R^{4'})$, $XNHCOR^4$, $XNHCOOR^4$, $XNHCONHR^4$, and $R^4$, wherein two substituents at $R^3$, if they are in ortho-position to one another, are optionally linked to one another to jointly form methanediylbisoxy, ethane-1,2-diylbisoxy, propane-1,3-diyl, or butane-1,4-diyl.

17. A method according to claim 13, wherein $R^4$ and $R^{4'}$, independently of one another, mean $CF_3$, $C_2F_5$, $C_{1-4}$ alkyl, $C_{2-4}$ alkenyl, $C_{2-4}$ alkinyl, $C_{3-6}$ cycloalkyl, ($C_{1-3}$ alkyl-$C_{3-6}$ cycloalkyl), $C_{1-3}$ alkylaryl, $C_{1-3}$ alkylheteroaryl, monocyclic aryl or 5- to 6-membered heteroaryl with 1-2 heteroatoms selected from N, S and O atoms, wherein the aryl and heteroaryl groups are optionally substituted with one or two substituents selected from of F, Cl, Br, $CH_3$, $C_2H_5$, $NO_2$, $OCH_3$, $OC_2H_5$, $CF_3$, and $C_2F_5$ or optionally carry an annelated methanediylbisoxy or ethane-1,2-diylbisoxy group, and wherein a 5-membered cycloalkyl ring optionally has a N or O ring member, and a 6-membered cycloalkyl ring optionally has one or two ring members selected from N and O, wherein ring nitrogens are optionally substituted with $C_{1-3}$ alkyl or $C_{1-3}$ alkanoyl.

18. A method according to claim 13, wherein $R^5$ and $R^{5'}$, independently of one another, are optionally $C_{1-6}$ alkyl (wherein a carbon atom is optionally replaced by O, NH, $NC_{1-3}$ alkyl, or $NC_{1-3}$ alkanoyl), or $C_{3-7}$ cycloalkyl-$C_{0-3}$ alkyl (wherein a 5- membered cycloalkyl ring optionally has a N or O ring member, and a 6- or 7-membered cycloalkyl ring optionally has one or two ring members selected from N and O, wherein ring nitrogens are optionally substituted with $C_{1-3}$alkyl or $C_{1-3}$ alkanoyl), wherein the mentioned $C_{1-6}$ alkyl is optionally substituted with one of the previously mentioned cycloalkyls or a 5- to 6-membered heteroaromatic compound with 1-2 heteroatoms selected from N, S and O atoms, and wherein all previously mentioned alkyl and cycloalkyl groups are optionally substituted with up to two substituents selected from of $CF_3$, OH, and $OC_{1-3}$ alkyl, and the previously mentioned heteroaryl groups are optionally substituted with one or two of F, Cl, $CF_3$, $CH_3$, $C_2H_5$, $OCH_3$, and/or $OC_2H_5$, or $R^5$ and $R^{5'}$ together with the nitrogen atom form a 5- to 7-membered heterocyclic group, which optionally contains another oxygen, nitrogen or sulfur atom and is optionally substituted with $C_{1-4}$ alkyl, $C_{1-4}$ alkoxy-$C_{0-2}$ alkyl, $C_{1-4}$ alkoxy-carbonyl, aminocarbonyl or phenyl.

19. A method according to claim 13, wherein

A means $C_{1-10}$ alkanediyl, $C_{2-10}$ alkenediyl, $C_{2-10}$ alkinediyl, ($C_{0-5}$ alkanediyl-$C_{3-7}$ cycloalkanediyl-$C_{0-5}$ alkanediyl), or ($C_{0-5}$ alkanediyl-heteroarylene-$C_{0-5}$ alkanediyl), wherein when a heteroaryl group is present it is optionally substituted with one or two substituents selected from of F, Cl, Br, $CH_3$, $C_2H_5$, $NO_2$, $OCH_3$, $OC_2H_5$, $CF_3$, and $C_2F_5$, and wherein a 5-membered cycloalkyl ring optionally has a N or O ring member, and a 6- or 7-membered cycloalkyl ring optionally has one or two ring members selected from N and O, wherein ring nitrogens are optionally substituted with $C_{1-3}$ alkyl or $C_{1-3}$ alkanoyl, wherein in an aliphatic group one or two carbon atoms are optionally replaced by O, NH, $NC_{1-3}$ alkyl, $NC_{1-3}$ alkanoyl, and/or $NSO_2C_{1-3}$ alkyl, and wherein alkyl or cycloalkyl groups are optionally substituted with up to two F atoms or by one of OH, $OC_{1-3}$ alkyl, $OC_{1-3}$ alkanoyl, =O, $NH_2$, $NHC_{1-3}$ alkyl, $N(C_{1-3}$ alkyl$)_2$, $NHC_{1-3}$ alkanoyl, $N(C_{1-3}$ alkyl) $(C_{1-3}$ alkanoyl), $NHCOOC_{1-3}$ alkyl, $NHCONHC_{1-3}$ alkyl, $NHSO_{2C1-3}$ alkyl, SH or $SC_{1-3}$ alkyl.

20. A method according to claim 13, wherein B means hydrogen, OH, $OCOR^5$, $OCONHR^5$, $OCOOR^5$, COOH, $COOR^5$, $CONH_2$, $CONHR^5$, $CONR^5R^{5'}$, CONHOH, $CONHOR^5$, or tetrazolyl, in each case bonded to a carbon atom of group A.

21. A method according to claim 13, wherein X means a bond or $CH_2$.

22. A method according to claim 13, wherein Y means a bond, O, S, NH, $NR^4$, $NCOR^4$ or $NSO_2R^4$.

23. A method according to claim 1, wherein the compound administered is 6-[[1-phenyl-2-(benzothien-2-yl)-1H-benzimidazol-6-yl]oxy]hexanoic acid methyl ester.

24. A method according to claim 13, wherein the compound administered is 6-[[1-phenyl-2-(benzothien-2-yl)-1H-benzimidazol-6-yl]oxy]hexanoic acid methyl ester.

25. A method according to claim 23, wherein the patient suffers from Alzheimer's disease, AIDS dementia or stroke.

26. A method according to claim 24, wherein the patient suffers from Alzheimer's disease, AIDS dementia or stroke.

27. A method according to claim 1, wherein the patient suffers from AIDS dementia, amyotrophic lateral sclerosis, Creutzfeldt-Jacob disease, Down's syndrome, diffuse Lewy body's disease, Huntington's disease, leukoencephalopathy, multiple sclerosis, Parkinson's disease, Pick's disease, Alzheimer's disease, stroke, temporary lobe epilepsy or a tumor.

28. A method according to claim 13, wherein the patient suffers from AIDS dementia, amyotrophic lateral sclerosis, Creutzfeldt-Jacob disease, Down's syndrome, diffuse Lewy body's disease, Huntington's disease, leukoencephalopathy, multiple sclerosis, Parkinson's disease, Pick's disease, Alzheimer's disease, stroke, temporary lobe epilepsy or a tumor.

29. A method according to claim 1, wherein the patient suffers from Alzheimer's disease, AIDS dementia or stroke.

30. A method according to claim 13, wherein the patient suffers from Alzheimer's disease, AIDS dementia or stroke.

31. A method according to claim 1, wherein the inflammation is associated with microglia activation.

32. A method according to claim 13, wherein the inflammation is associated with microglia activation.

* * * * *

UNITED STATES PATENT AND TRADEMARK OFFICE
CERTIFICATE OF CORRECTION

PATENT NO. : 7,329,679 B2
APPLICATION NO. : 11/299135
DATED : February 12, 2008
INVENTOR(S) : Wolfgang Halfbrodt It is certified that error appears in the above-identified patent and that said Letters Patent is hereby corrected as shown below:

Claim 1, Column 99, line 64 reads "$_{OC_2H_5}$", should read -- $OC_2H_5$ --
Claim 1, Column 100, line 24 reads "COGH", should read -- COOH --
Claim 1, Column 100, line 52 reads "$PO^3H,.$", should read -- $PO_3H,.$ --
Claim 1, Column 101, line 1 reads "$PO^3H_2$", should read -- $PO_3H_2$ --
Claim 1, Column 101, line 8 reads "from of", should read -- from the group consisting of --
Claim 4, Column 101, line 53 reads "$XNHSO_{2r}{}^{4}$", should read -- $XNHSO_2R^4$ --
Claim 4, Column 101, line 53 reads "$XN(SOR^4)SOR^{4'}$" should read -- $XN(SO_2R^4)SO_2R^{4,}$ --
Claim 5, Column 101, line 67 reads "$_{OC_2}H^5$", should read -- $OC_2H^5$ --
Claim 13, Column 102, line 35 reads "$(C_{05}$", should read -- $C_{0-5}$ --
Claim 13, Column 103, line 57 reads "selected from of" should read -- selected from --
Claim 13, Column 103, line 66 reads "$^{XN(SO}{}_2R^{4}$" should read -- $XN(SO_2R^4)$ --
Claim 13, Column 105, line 22 reads "$^{=O,NH}{}_2$" should read -- $=ONH_2$ --
Claim 19, Column 107, line 16 reads "$NHSO_{2C1-3}$" should read -- $NHSOC_{1-3}$ --

Signed and Sealed this

Seventeenth Day of August, 2010

David J. Kappos
*Director of the United States Patent and Trademark Office*